US007856317B2

(12) United States Patent
Schilling

(10) Patent No.: US 7,856,317 B2
(45) Date of Patent: Dec. 21, 2010

(54) SYSTEMS AND METHODS FOR CONSTRUCTING GENOMIC-BASED PHENOTYPIC MODELS

(75) Inventor: Christophe H. Schilling, San Diego, CA (US)

(73) Assignee: Genomatica, Inc., San Diego, CA (US)

(*) Notice: Subject to any disclaimer, the term of this patent is extended or adjusted under 35 U.S.C. 154(b) by 27 days.

(21) Appl. No.: 10/173,547

(22) Filed: Jun. 14, 2002

(65) Prior Publication Data
US 2003/0233218 A1 Dec. 18, 2003

(51) Int. Cl.
*G01N 33/48* (2006.01)
(52) U.S. Cl. ....................................................... 702/19
(58) Field of Classification Search .................. 702/19, 702/27
See application file for complete search history.

(56) References Cited

U.S. PATENT DOCUMENTS

| | | | |
|---|---|---|---|
| 5,273,038 A | 12/1993 | Beavin et al. |
| 5,556,762 A | 9/1996 | Pinilla et al. |
| 5,639,949 A | 6/1997 | Ligon et al. |
| 5,689,633 A | 11/1997 | Cotner et al. |
| 5,914,891 A | 6/1999 | Arkin et al. |
| 5,930,154 A | 7/1999 | Thalhammer-Reyero |
| 5,947,899 A | 9/1999 | Scollan et al. |
| 6,132,969 A | 10/2000 | Stoughton et al. |
| 6,165,709 A | 12/2000 | Friend et al. |
| 6,200,803 B1 | 3/2001 | Roberts |
| 6,221,597 B1 | 4/2001 | Roberts |
| 6,302,302 B1 | 10/2001 | Albisetti |
| 6,326,140 B1 | 12/2001 | Rine et al. |
| 6,329,139 B1 | 12/2001 | Nova et al. |
| 6,351,712 B1 | 2/2002 | Stoughton et al. |
| 6,370,478 B1 | 4/2002 | Stoughton et al. |
| 6,379,964 B1 | 4/2002 | Del Cardayre |
| 6,500,710 B2 | 1/2005 | Thalhammer-Reyero |
| 6,983,227 B1 | 1/2006 | Thalhammer-Reyero |
| 6,902,692 B2 | 10/2006 | Palsson et al. |
| 7,127,379 B2 | 10/2006 | Palsson et al. |
| 2002/0012939 A1 | 1/2002 | Palsson et al. |
| 2002/0051998 A1 | 5/2002 | Schmidt et al. |
| 2002/0168654 A1 | 11/2002 | Maranas et al. |
| 2003/0059792 A1 | 3/2003 | Palsson et al. |
| 2003/0113761 A1 | 6/2003 | Tan et al. |
| 2003/0233218 A1 | 12/2003 | Schilling |
| 2008/0176327 A1 | 7/2008 | Palsson et al. |

FOREIGN PATENT DOCUMENTS

| WO | WO 92/09300 | 6/1992 |
|---|---|---|
| WO | WO 00/46405 | 8/2000 |
| WO | WO 01/36658 | 5/2001 |
| WO | WO 01/57775 | 8/2001 |
| WO | WO 02/055995 | 7/2002 |
| WO | WO 2002/061115 | 8/2002 |
| WO | WO 03/106998 | 12/2003 |

OTHER PUBLICATIONS

Ogata et al., Nucleic Acids Research, vol. 27, pp. 29-34, 1999.*
Goto et al., Bioinformatics, vol. 14, pp. 591-599, 1998.*
Goto et al., Nucleic Acids Research, vol. 27, pp. 377-379, 1999.*
Karp, P., Bioinformatics, vol. 16, pp. 269-285, 2000.*
Matrix, Dictionary.com, pp. 1-2, 2004.*
Schuster et al., Bioinformatics, vol. 18, No. 2, pp. 351-361, Feb. 1, 2002.*
Voet & Voet, Biochemstry, John Wiley & Sons, Inc., pp. 335-338, and 409-410, 1990.*
Dandekar et al. Biochem. J., vol. 343, pp. 115-124, 1999.*
Bansal, A. K., Bioinformatics and Bioengineering Conference, 2001, pp. 209-216, 2001.*
Covert et al., "Regulation of Gene Expression in Flux Balance Models of Metabolism," *J. Theor. Biol.*, 213:73-88 (2001).
Covert et al., "Metabolic modeling of microbial strains in silico," *Trends in Biochemical Sciences*, 26:179-186 (2001).
Dauner and Sauer, "Stoichiometric Growth Model for Riboflavin-Producing *Bacillus subtilis*," *Biotechnol. Bioeng.*, 76:132-143 (2001).
Dauner et al., "Metabolic Flux Analysis with a Comprehensive Isotopomer Model in *Bacillus subtilis*," *Biotechnol. Bioeng.*, 76:144-156 (2001).
Dauner et al., "*Bacillus subtilis* Metabolism and Energetics in Carbon-Limited and Excess-Carbon Chemostat Culture," *J. Bact.*, 183:7308-7317 (2001).
Edwards et al., "In silico predictions of *Escherichia coli* metabolic capabilities are consistent with experimental data," *Nature Biotech.*, 19:125-130 (2001).
Edwards et al., "Characterizing the Metabolic Phenotype: A Phenotype Phase Plane Analysis," *Biotech. Bioeng.*, 77:27-36 (2002).
Edwards and Palsson, "The *Escherichia coli* MG1655 in silico metabolic genotype: Its definition, characteristics, and capabilities," *Proc. Natl. Acad. Sci. USA*, 97:5528-5533 (2000).
Edwards and Palsson, "Systems Properties of the *Haemophilus influenzae* Rd Metabolic Genotype," *J. Biol. Chem.*, 274:17410-17416 (1999).

(Continued)

*Primary Examiner*—Jerry Lin
(74) *Attorney, Agent, or Firm*—McDermott Will & Emery LLP

(57) ABSTRACT

The invention provides a computer implemented process for constructing a scalable output network model of a bioparticle. The process includes computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components, and (c) transforming the data set into a mathematical description of reactant fluxes defining the network model of connectivity and flow, wherein the mathematical description defines a scalable output network model of a bioparticle.

23 Claims, 18 Drawing Sheets

OTHER PUBLICATIONS

Fell and Small, "Fat synthesis in adipose tissue An examination of stoichiometric constraints," *Biochem. J.*, 238:781-786 (1986).

Kunst et al., "The complete genome sequence of the Gram-positive bacterium *Bacillus subtilis*," *Nature*, 390:249-256 (1997).

Majewski and Domach, "Simple Constrained-Optimization View of Acetate Overflow in *E. coli*," *Biotech. Bioeng.*, 35:732-738 (1990).

Palsson, B., "The challenges of in silico biology," *Nat. Biotech*, 18:1147-1150 (2000).

Sauer and Bailey, "Estimation of P-to-O Ratio in *Bacillus subtilis* and Its Influence on Maximum Riboflavin Yield," *Biotechnol. Bioeng.*, 64:750-754 (1999).

Schilling et al., "Theory for the Systemic Definition of Metabolic Pathways and their use in Interpreting Metabolic Function from a Pathway-Oriented Perspective," *J. Theor. Biol.*, 203:229-248 (2000).

Schilling and Palsson, "Assessment of the Metabolic Capabilities *Haemophilus influenzae* Rd through a Genome-scale Pathway Analysis," *J. Theor. Biol.*, 203:249-283 (2000).

Schilling et al., "Combining Pathway Analysis with Flux Balance Analysis for the Comprehensive Study of Metabolic Systems," *Biotech. Bioeng.*, 71:286-306 (2000).

Schilling et al., "Toward Metabolic Phenomics: Analysis of Genomic Data Using Flux Balances," *Biotech. Prog.*, 15:288-295 (1999).

Schilling et al, "Metabolic Pathway Analysis: Basic Concepts and Scientific Applications in the Post-genomic Era," *Biotech. Prog.*, 15:296-303 (1999).

Schilling and Palsson, "The underlying pathway structure of biochemical reaction networks," *Proc. Natl. Acad. Sci. USA*, 95:4193-4198 (1998).

Thomas, R., "Logical Analysis of Systems Comprising Feedback Loops," *J. Theor. Biol.*, 73:631-656 (1978).

Thomas, R., "Boolean Formalization of Genetic Control Circuits," *J. Theor. Biol.*, 42:563-585 (1973).

Vanrolleghem et al., "Validation of a Metabolic Network for *Saccharomyces cerevisiae* Using Mixed Substrate Studies," *Biotech. Prog.*, 12:434-448 (1996).

Varma and Palsson, "Metabolic Flux Balancing: Basic Concepts, Scientific and Practical Use," *Biotech.*, 12:994-998 (1994).

Beckers et al., "Large-scare mutational analysis for the annotation of the mouse genome," *Curr. Opin. Chem. Biol.*, 6:17-23 (2001).

Hardison et al., "Globin gene server: a prototype e-mail database server featuring extensive multiple alignments and data compilation for electronic genetic analysis," *Genomics*, 21:344-353 (1994).

Jenssen et al., "A literature network of human genes for high-throughput analysis of gene expression," *Nat. Genetics*, 28:21-28 (2001).

Juty et al., "Simultaneous modeling of metabolic, genetic and product-interaction networks," *Briefings in Bioinformatics*, 2(3):223-232 (2001).

Moszer, I., "The complete genome of *Bacillus subtilis*: from sequence annotation to data management and analysis," *FEBS Letters*, 430:28-36 (1998).

Romero et al., "Nutrient-related analysis of pathway/genome databases" *Pacific Symposium on Biocomputing*, pp. 471-482 (2001).

Covert et al., "Metabolic modeling of microbial strains in silico," *TRENDS in Biochem. Sci.* 26(3):179-186 (2001).

Schilling et al., "Combining pathway analysis with flux balance analysis for the comprehensive study of metabolic systems," *Biotech Bioeng* 71(4):286-306 (2000).

Schilling et al., "Toward metabolic phenomics: analysis of genomic data using flux balances," *Biotechnol. Prog.* 15:288-295 (1999).

Adamowicz, et al., "Nutritional complementation of oxidative glucose metabolism in *Escherichia coli* via pyrroloquinoline quinone-dependent glucose dehydrogenase and the Entner-Doudoroff pathway," *Appl Environ Microbiol*, 57(7):2012-2015 (1991).

Alberty, "Calculation of Biochemical Net Reactions and Pathways by Using Matrix Operations," *Biophys J*, 71(1):507-515 (1996).

Alm, et al., "Genomic-sequence comparison of two unrelated isolates of the human gastric pathogen *Helicobacter pylori*," *Nature*, 397(6715):176-80 (1999).

Alon, et al., "Broad patterns of gene expression revealed by clustering analysis of tumor and normal colon tissues probed by oligonucleotide arrays," *Proc Natl Acad Sci U.S.A.*, 96(12):6745-6750 (1999).

Alter, et al., "Singular value decomposition for genome-wide expression data processing and modeling," *Proc Natl Acad Sci U.S.A.*, 97(18):10101-10106 (2000).

Altschul, et al., "Gapped BLAST and PSI-BLAST: A New Generation of Protein Database Search Programs," *Nucl Acids Res*, 25(17):3389-3402 (1997).

Alves, et al., "Systemic properties of ensembles of metabolic networks: application of graphical and statistical methods to simple unbranched pathways," *Bioinformatics*, 16(6):534-547 (2000).

Andre, "An overview of membrane transport proteins in *Saccharomyces cerevisiae*," *Yeast*, 11(16):1575-1611 (1995).

Anonymous, "The yeast genome directory" *Nature*, 387(6632 Suppl):5 (1997).

Appel, et al., "A new generation of information retrieval tools for biologists: the example of the ExPASy WWW server," *Trends Biochem Sci*, 19(6):258-260 (1994).

Arigoni, et al., "A Genome-Based Approach for the Identification of Essential Bacterial Genes," *Nature Biotechnology*, 16(9):851-856 (1998).

Attanoos, et al., "Ileostomy polyps, adenomas, and adenocarcinomas," *Gut*, 37(6):840-844 (1995).

Baba, et al., "Construction of *Escherichia coli* K-12 in-frame, single-gene knockout mutants: the Keio collection," *Mol Syst Biol*, 2:1-11 (2006).

Bailey, "Complex Biology With No Parameters," *Nat Biotechnol*, 19(6):503-504 (2001).

Bailey, TL and Elkan, C, "Fitting a mixture model by expectation maximization to discover motifs in biopolymers," *Proc Int Conf Intell Syst Mol Biol*, 2:28-36 (1994).

Bailey, TL and Gribskov, M, "Combining evidence using p-values: application to sequence homology searches," *Bioinformatics*, 14(1):48-54 (1998).

Bairoch, A, and Apweiler, R, "The SWISS-PROT Protein Sequence database and its supplement TrEMBL in 2000," *Nucleic Acids Res*, 28(1):45-48 (2000).

Ball, et al., "Integrating functional genomic information into the Saccharomyces genome database," *Nucleic Acids Res*, 28(1):77-80 (2000).

Baltz, et al., "DNA Sequence Sampling of the Streptococcus Pneumonia Genome to Identify Novel Tragets for Antibiotic Development," *Microbial Drug Resistance*, 4(1):1-9 (1998).

Ban, et al., "Thymine and uracil catabolism in *Escherichia coli*," *J Gen Microbiol*, 73(2):267-272 (1972).

Bard, et al., "Sterol mutants of *Saccharomyces cerevisiae*: chromatographic analyses," *Lipids*, 12(8):645-654 (1977).

Baxevanis, "The Molecular Biology Database Collection: 2002 update," *Nucleic Acids Res*, 30:1-12 (2002).

Beard, et al., "Energy Balance for Analysis of Complex Metabolic Networks," *Biophys J*, 83(1):79-86 (2002).

Bell, et al., "Composition and functional analysis of the *Saccharomyces cerevisiae* trehalose synthase complex," *J Biol Chem.*, 273(50):33311-33319 (1998).

Benson, et al., "GenBank," *Nucleic Acids Res*, 28(1):15-18 (2000).

Berry, "Improving production of aromatic compounds in *Escherichia coli* by metabolic engineering," *Trends Biotechnol*, 14(7):250-256 (1996).

Bialy, "Living on the Edges," *Nat Biotechnol*, 19(2):111-112 (2001).

Bianchi, P, and Zanella, A, *Blood Cells, Molecules, and Diseases*, 15:47-53 (2000).

Biaudet, et al., "Micado—A network-oriented database for microbial genomes," *Comput Appl Biosci*, 13(4):431-438 (1997).

Birkholz, "Fumarate reductase of *Helicobacter pylori*—an immunogenic protein," *J Med Microbiol*, 41(1):56-62 (1994).

Birner, et al., "Roles of phosphatidylethanolamine and of its several biosynthetic pathways in *Saccharomyces cerevisiae*," *Mol Biol Cell*, 12(4):997-1007 (2001).

Blackstock, WP and Weir, MP, "Proteomics: quantitative and physical mapping of cellular proteins," *Trends Biotechnol*, 17(3):121-127 (1999).

Blattner, et al., "The Complete Genome Sequence of *Escherichia coli* K-12," *Science*, 277(5331):1453-1474 (1997).

BMES/EMBS Conference, Proceedings of the First Joint, vol. 2, p. 1217 (1999).

Bochner, "New technologies to assess genotype-phenotype relationships," *Nat Rev Genet*, 4(4):309-314 (2003).

Boles, E, et al., "Identification and characterization of MAE 1, the *Saccharomyces cerevisiae* structural gene encoding mitochondrial malic enzyme," *J Bacteriol.*, 180(11):2875-2882 (1998).

Boles, et al., "A family of hexosephosphate mutases in *Saccharomyces cerevisia*," *Eur J Biochem*, 220(1):83-96 (1994).

Boles, et al., "Characterization of a glucose-repressed pyruvate kinase (Pyk2p) in *Saccharomyces cerevisiae* that is catalytically insensitive to fructose-1,6-bisphosphate," *J Bacteriol*, 179(9):2987-2993 (1997).

Bonarius, et al., "Flux Analysis of Underdetermined Metabolic Networks: The Quest for the Missing Constraints," *Trends Biotechnol*, 15(8):308-314 (1997).

Bonarius, et al., "Metabolic flux analysis of hybridoma cells in different culture media using mass balances," *Biotechnol Bioeng*, 50(3):299-318 (1996).

Bono, et al., "Reconstruction of amino acid biosynthesis pathways from the complete genome sequence," *Genome Research*, 8(3):203-210 (1998).

Bottomley, et al., "Cloning, sequencing, expression, purification and preliminary characterization of a type II dehydroquinase from *Helicobacter pylori*," *Biochem. J*, 319(Pt 2):559-565 (1996).

Bourot, S and Karst, F, "Isolation and characterization of the *Saccharomyces cerevisiae* SUT1 gene involved in sterol uptake," *Gene*, 165(1):97-102 (1995).

Burgard, AP and Maranas, CD, "Probing the Performance Limits of the *Escherichia coli* Metabolic Network Subject to Gene Additions or Deletions," *Biotechnol Bioeng*, 74(5):364-375 (2001).

Burgard, AP and Maranas, CD, "Review of the Enzymes and Metabolic Pathways (EMP) Database," *Metab Eng*, 3(3):193-194(2) (2001).

Burgard, et al., "Minimal reaction sets for *Escherichia coli* metabolism under different growth requirements and uptake environments," *Biotechnol Prog*, 17(5):791-797 (2001).

Burgard, et al., "Optknock: a bilevel programming framework for identifying gene knockout strategies for microbial strain optimization," *Biotechnol Bioeng*, 84(6):647-657 (2003).

Burns, "Acetyl-CoA carboxylase activity in *Helicobacter pylori* and the requirement of increased CO2 for growth," *Microbiology*, 141(Pt 12):3113-3118 (1995).

Chadha, et al., "Hybrid process for ethanol production from rice straw," Acta Microbiol Immunol Hung, 42(1):71-75 (1995).

Chalker, et al., "Systematic identification of selective essential genes in *Helicobacter pylori* by genome prioritization and allelic replacement mutagenesis," *J Bacteriol*, 183(4):1259-1268 (2001).

Chen, et al., "Characterization of the respiratory chain of *Helicobacter pylori*, " *FEMS Immunol Med Microbiol*, 24(2):169-174 (1999).

Cherry, et al., "SGD: Saccharomyces Genome Database," *Nucleic Acids Res*, 26(1):73-79 (1998).

Ciriacy, M and Breitenbach, I, "Physiological effects of seven different blocks in glycolysis in *Saccharomyces cerevisiae*," *J Bacteriol*, 139(1):152-160 (1979).

Clarke, "Complete set of steady states for the general stoichiometric dynamical system," *J Chem Phys*, 75(10):4970-4979 (1981).

Clifton, D and Fraenkel, DG, "Mutant studies of yeast phosphofructokinase.," *Biochemistry*, 21(8):1935-1942 (1982).

Clifton, et al., "Glycolysis mutants in *Saccharomyces cerevisiae*.," *Genetics*, 88(1):1-11 (1978).

Compan, I and Touati, D, et al., "Anaerobic activation of arcA transcription in *Escherichia coli* : roles of Fnr and ArcA," *Mol Microbiol*, 11(5):955-964 (1994).

Costanzo, et al., "YPD, PombePD and WormPD: model organism volumes of the BioKnowledge library, an integrated resource for protein information" *Nucleic Acids Res*, 29(1):75-9 (2001).

Cotter, et al., "Aerobic regulation of cytochrome d oxidase (cydAB) operon expression in *Escherichia coli* : roles of Fnr and ArcA in repression and activation," *Mol Microbol*, 25(3):605-615 (1997).

Covert and Palsson, "Constraints-based models: regulation of gene expression reduces the steady-state solution space," *J Theor Biol*, 221:309-325 (2003).

Covert and Palsson, "Transcriptional regulation in constraints-based metabolic models of *Escherichia coli*," *J Biol Chem*, 277(31):28058-28064 (2002).

Cupp, JR and McAlister-Henn, L, "Cloning and Characterization of the gene encoding the IDH1 subunit of Nad(+)-dependent isocitrate dehydrogenase from *Saccharomyces cerevisiae*," *J Biol Chem*, 267(23):16417-16423 (1992).

D'Haeseleer, et al., "Genetic network inference: from co-expression clustering to reverse engineering," *Bioinformatics*, 16(8):707-726 (2000).

Danchin, "Comparison Between the *Escherichia coli* and *Bacillus subtilis* Genomes Suggests That a Major Function of Polynucleotide Phosphorylase is to Synthesize CDP," *DNA Research*, 4(1):9-18 (1997).

Dantigny, et al., "A new control strategy for yeast production based on the L/A* approach," *Appl Microbiol Biotechnol*, 36:352-357 (1991).

Datsenko, KA and Wanner, BL, "One-step inactivation of chromosomal genes in *Escherichia coli* K-12 using PCR products," *Proc Natl Acad Sci U.S.A.*, 97(12):6640-6645 (2000).

Daum, et al., "Biochemistry, cell biology and molecular biology of lipids of *Saccharomyces cerevisiae*," *Yeast*, 14(16):1471-1510 (1998).

Daum, et al., "Systematic analysis of yeast strains with possible defects in lipid metabolism," *Yeast*, 15(7):601-614 (1999).

de Jong, H., "Modeling and simulation of genetic regulatory systems: a literature review," *J Comput Biol*, 9(1):67-103 (2002).

De Reuse, et al., "The *Helicobacter pylori* ureC gene codes for a phosphoglucosamine mutase," *J Bacteriol*, 179(11):3488-3493 (1997).

Delgado and Liao, "Identifying Rate-Controlling Enzymes in Metabolic Pathways without Kinetic Parameters," *Biotechnol Prog*, 7:15-20 (1991).

Demain, et al., "Cellulase, clostridia, and ethanol," *Microbiol Mol Biol Rev*, 69(1):124-154 (2005).

Department of Energy, *Breaking the Biological Barriers to Cellulosic Ethanol* (2006).

DeRisi, et al.,"Exploring the Metabolic and Genetic Control of Gene Expression on a Genomic Scale," *Science*, 278(5338):680-686 (1997).

Devine, KM, "The *Bacillus subtilis* Genome Project: Aims and Progress," *Trends Biotechnol*, 13(6):210-216 (1995).

Dickson, "Sphingolipid function in *Saccoaromyces cerevisiae*: somparison to mammals," *Annu Rev Biochem*, 67:27-48 (1998).

Dickson, et al., "Serine palmitoyltransferase," *Methods Enzymol*, 311:3-9 (2000).

DiRusso, CC and Black, PN, "Long-chain fatty acid transport in bacteria and yeast. Paradigms for defining the mechanism underlying this protein-mediated process," *Mol Cell Biochem*, 192(1-2):41-52 (1999).

Edwards, JS and Palsson, BO, "How Will Bioinformatics Influence Metabolic Engineering," *Biotechnol Bioeng*, 58(2-3):162-169 (1998).

Edwards, JS and Palsson, BO, "Robustness analysis of the *Escherichia coli* metabolic network," *Biotechnol Prog*, 16(6):927-939 (2000).

Edwards, JS, and Palsson, BO, "Metabolic flux balance analysis and the in silico analysis of *Escherichia colia* K-12 gene deletions," *BMC Bioinformatics*, 1:1-10 (2000).

Edwards, et al., "Genomically Based Comparative Flux Balance Analysis of *Escherichia coli* and *Haemophilus Influenza*," Abstract of Papers, American Chemical Society, 213 (1-3): BIOT 50. San Francisco (13-17, 1997).

Eisen, et al., "Cluster analysis and display of genome-wide expression patterns," *Proc Natl Acad Sci U.S.A.*, 95:14863-14868 (1998).

Eisenberg, et al., "Protein Function in the Post-Genomic Era," *Nature*, 405(6788):823-826 (2000).

Ermolaeva, et al., "Prediction of Operons in Microbial Genomes," *Nucl Acids Research*, 29(5):1216-1221 (2001).

Everett, et al., "Pendred Syndrome is Caused by Mutations in a Putative Sulphate Transporter Gene (PDS)," *Nat Genet*, 17:411-422 (1997).

Fiehn, "Metabolomics—the link between genotypes and phenotypes," *Plant Mol Biol*, 48 (1-2):155-171 (2002).

Finel, "Does NADH play a central role in energy metabolism in *Helicobacter pylori*?," *Trends Biochem Sci*, 23(11):412-413 (1998).

Fiorelli, et al., "Chronic non-spherocytic haemolytic disorders associated with glucose-6-phosphate dehydrogenase variants," *Bailliere's Clinical Haematology*, 13:39-55 (2000).

Flikweert, et al., "Pyruvate decarboxylase: an indispensable enzyme for growth of *Saccharomyces cerevisiae* on glucose.," *Yeast*, 12(3):247-257 (1996).

Forst, "Network genomics—A Novel approach for the analysis of biological systems in the post-genomic era," *Molecular Biology Reports*, 29(3):265-280 (2002).

Forster, et al., "Large-scale evaluation of in silico gene deletions in *Saccharomyces cerevisiae*," *Omics*, 7(2)193-202 (2003).

Fraenkel, "The accumulation of glucose 6-phosphate from glucose and its effect in an *Escherichia coli* mutant lacking phosphoglucose isomerase and glucose 6-phosphate dehydrogenase," *J Biol Chem*, 243(24):6451-6457 (1968).

Fraser, et al., "Microbial genome sequencing," *Nature*, 406:799-803 (2000).

Fromont-Racine, et al., "Toward a functional analysis of the yeast genome through exhaustive two-hybrid screens," *Nat Genet*, 16(3):277-282 (1997).

Fukuchi, et al., "Isolation, overexpression and disruption of a *Saccharomyces cerevisiae* YNK gene encoding nucleoside diphosphate kinase," *Genes*, 129(1):141-146 (1993).

Gaasterland, T. and Selkov, E., "Reconstruction of Metabolic Networks Using Incomplete Information," *Proc Int Conf Intell Syst Mol Biol*, 3:127-135 (1995).

Galperin, MY and Brenner, SE, "Using Metabolic Pathway Databases for Functional Annotation," *Trends Genet*, 14(8):332-333 (1998).

Gancedo, C and Delgado, MA, "Isolation and characterization of a mutant from *Saccharomyces cerevisiae* lacking fructose 1,6-bisphosphatase," *Eur J Biochem*, 139:651-655 (1984).

Gangloff, et al., "Molecular cloning of the yeast mitochondrial aconitase gene (ACO1) and evidence of a synergistic regulation of expression by glucose plus glutamate.," *Mol. Cell Biol*, 10(7):3551-3561 (1990).

Glasner, et al., "ASAP, a systematic annotation package for community analysis of genomes," *Nucleic Acids Res*, 31(1):147-151 (2003).

Goffeau, A, "Four years of post-genomic life with 6000 yeast genes," *FEBS Lett*, 480(1):37-41 (2000).

Goryanin, et al., "Mathematical simulation and analysis of cellular metabolism and regulation," *Bioinformatics*, 15(9):749-758 (1999).

Grewal, et al., "Computer Modelling of the Interaction Between Human Choriogonadotropin and Its Receptor," *Protein Engineering*, 7(2):205-211 (1994).

Griffin, et al., "Complementary profiling of gene expression at the transcriptome and proteome levels in *Saccharomyces cerevisiae*," *Mol Cell Proteomics*, 1:323-333 (2002).

Grundy, et al., "Regulation of the *Bacillus subtilis* acetate kinase gene by CcpA." *J Bacteriol*, 175(22):7348-7355 (1993).

Guelzim, et al., "Topological and causal structure of the yeast transcriptional regulatory network," *Nat Genet*, 31(1):60-63 (2002).

Guetsova, et al., "The isolation and characterization of *Saccharomyces cerevisiae* mutants that constitutively express purine biosynthetic genes," *Genetics*, 147(2):383-397 (1997).

Hartig, et al., "Differentially regulated malate synthase genes participate in carbon and nitrogen metabolism of *S. cerevisiae*.," *Nucleic Acids Res*, 20(21):5677-5686 (1992).

Hasty, et al., "Computational Studies of Gene Regulatory Networks: *In Numero* Molecular Biology," *Nat Rev Genet*, 2(4):268-279 (2001).

Hata, et al., "Characterization of a *Saccharomyces cerevisiae* mutant, N22, defective in ergosterol synthesis and preparation of [28-14C]ergosta-5,7-dien-3 beta-ol with the mutant," *J Biochem*, 94(2):501-510 (1983).

Hatzimanikatis, et al., "Analysis and Design of Metabolic Reaction Networks Via Mixed-Interger linear Optimization," *AIChE Journal*, 42(5):1277-1292 (1996).

Hazell, et al., "How *Helicobacter pylori* works: an overview of the metabolism of *Helicobacter pylori*," *Helicobacter*, 2(1):1-12 (1997).

Heijnen, et al., "Application of balancing methods in modeling the penicillin fermentation," *Biotechnol. Bioeng*, 21:2175-2201 (1979).

Heinisch, et al., "Investigation of two yeast genes encoding putative isoenzymes of phosphoglycerate mutase.," *Yeast*, 14(3):203-213 (1998).

Heinrich, et al., "Metabolic regulation and mathematical models," *Prog Biophys Mol Biol*, 32(1):1-82 (1977).

Heinrich, et al., "Stoichiometric Analysis," *The Regulation of Cellular Systems*, xix:75-111 and 372, Chapman & Hall, New York (1996).

Henriksen, et al., "Growth energetics and metabolism fluxes in continuous cultures of *Penicillium chrysogenum*," *J of Biotechnol*, 45(2):149-164 (1996).

Heyer, et al., "Exploring expression data: identification and analysis of coexpressed genes," *Genome Res*, 9(11):1106-1115 (1999).

Holter, et al., "Dynamic modeling of gene expression data," *Proc Natl Acad Sci U.S.A.*, 98(4):1693-1698 (2001).

Holter, et al., "Fundamental patterns underlying gene expression profiles: simplicity from complexity," *Proc Natl Acad Sci U.S.A.*, 97:8409-9414 (2000).

Houghten, "Generation and use of synthetic peptide combinatorial libraries for basic research and drug discovery," *Nature*, 354(6348):84-86 (1991).

Hughes, et al., "Functional discovery via a compendium of expression profiles," *Cell*, 102(1):109-126 (2000).

Hughes, et al., "*Helicobacter pylori* porCDAB and oorDABC genes encode distinct pyruvate: flavodoxin and 2-oxoglutarate:acceptor oxidoreductases which mediate electron transport to NADP," *J Bacteriol*, 180(5):1119-1128 (1998).

Ideker, et al., "Integrated Genomic and Proteomic Analyses of a Systematically Perturbed Metabolic Network," *Science*, 292(5518):929-934 (2001).

Ince, JE and Knowles, CJ, "Ethylene formation by cell-free extracts of *Escherichia coli*," *Arch Microbiol*, 146(2):151-158 (1986).

Ishii, et al., "DBTBS: a database of *Bacillus subtilis* promoters and transcription factors," *Nucleic Acids Res*, 29(1):278-280 (2001).

Iyer, et al., "Genomic binding sites of the yeast cell-cycle transcription factors SBF and MBF," *Nature*, 409(6819):533-538 (2001).

Jamshidi, et al., "Dynamic simulation of the human red blood cell metabolic network," *Bioinformatics*, 17(3):286-287 (2001).

Jamshidi, et al., "In silico model-driven assessment of the effects of single nucleotide polymorphins (SNPs) on human red blood cell-metabolism," *Genome Research*, 12(11):1687-1692 (2002).

Jenkins, LS and Nunn, WD, "Genetic and molecular characterization of the genes involved in short-chain fatty acid degradation in *Escherichia coli*: the ato system," *J Bacteriol*, 169(1):42-52 (1987).

Jorgensen, et al., "Metabolic flux distributions in *Penicillium chrysogenum* during fed-batch cultivations." *Biotechnol Bioeng*, 46(2):117-131 (1995).

Joshi, A and Palsson, BO, "Metabolic dynamics in the human red cell. Part I—A comprehensive kinetic model," *J Theor Biol*, 141(4):515-528 (1989).

Kanehisa, M and Goto, S, "Kyoto Encyclopedia of Genes and Genomes database (KEGG)," *Nucleic Acids Res*, 28(1):27-30 (2000).

Karp, "Metabolic Databases," *Trends Biochem Sci*, Elsevier Publication, Cambridge, 23(3):114-116 (1998).

Karp, et al., "Eco Cyc: encyclopedia of *Escherichia coli* genes and metabolism," *Nucleic Acids Res*, 27(1):55-58 (1999).

Karp, et al., "EcoCyc: Encyclopedia of *Escherichia coli* Genes and Metabolism," *Nucleic Acids Research*, 25(1):43-50 (1997).

Karp, et al., "HinCyc: A knowledge base of the complete genome and metabolic pathways of *H. influenzae*," *Proc Int Conf Intell Syst Mol Biol*, 4:116-124 (1996).

Karp, et al., "Integrated pathway-genome databases and their role in drug discovery.," *Trends Biotechnol*, 17(7):275-281 (1999).

Karp, et al., "The EcoCyc and MetaCyc databases," *Nucleic Acids Resarch*, 28(1):56-59 (2000).

Kather, et al., "Another unusual type of citric acid cycle enzyme in *Helicobacter pylori*: the malate:quinone oxidoreductase," *J Bacteriol*, 182(11):3204-3209 (2000).

Keating, et al., "An ethanologenic yeast exhibiting unusual metabolism in the fermentation of lignocellulosic hexose sugars," *J Ind Microbiol Biotechnol*, 31(5):235-244 (2004).

Kim, et al., "*Saccharomyces cerevisiae* contains two functional citrate synthase genes.," *Mol Cell Biol*, 6(6):1936-1942 (1986).

Kirkman, et al., "Red cell NADP+ and NADPH in glucose-6-phosphate dehydrogenase deficiency," *Journal of Clinical Investigation*, 55(4):875-878 (1975).

Kremling, et al., "The organization of metabolic reaction networks. III. Application for diauxic growth on glucose and lactose," *Metab Eng*, 3(4):362-379 (2001).

Lacroute, "Regulation of pyrimidine biosynthesis in *Saccharomyces cerevisiae*" *J Bacteriol*, 95(3):824-832 (1968).

Latif, F and Rajoka, MI, "Production of ethanol and xylitol from corn cobs by yeasts," *Bioresour Technol*, 77(1):57-63 (2001).

Lendenmann, U and Egli, T, "Is *Escherichia coli* growing in glucose-limited chemostat culture able to utilize other sugars without lag?," *Microbiology*, 141(Pt 1):71-78 (1995).

Leyva-Vasquez, MA and Setlow, P, "Cloning and nucleotide sequences of the genes encoding triose phosphate isomerase, phosphoglycerate mutase, and enolase from *Bacillus subtilis*," *J Bacteriol*, 176(13):3903-3910 (1994).

Li, C and Wong, WH, "Model-based analysis of oligonucleotide arrays: expression index computation and outlier detection," *Proc Natl Acad Sci U.S.A.*, 98(1):31-36 (2001).

Liao, et al., "Pathway Analysis, Engineering, and Physiological Considerations for Redirecting Central Metabolism," *Biotechnol Bioeng*, 52(1):129-140 (1996).

Liao, JC and Oh, MK, "Toward predicting metabolic fluxes in metabolically engineered strains," *Metab Eng*,1(3):214-223 (1999).

Link, et al., "Methods for generating precise deletions and insertions in the genome of wild-type *Escherichia coli*: Application to open reading frame characterization," *J Bacteriol*, 179(20):6228-6237 (1997).

Loftus, et al., "Isolation, characterization, and disruption of the yeast gene encoding cytosolic NADP-specific isocitrate dehydrogenase," *Biochemistry*, 33(32):9661-9667 (1994).

Lopez, et al., "The yeast inositol monophosphatase is a lithium- and sodium-sensitive enzyme encoded by a non-essential gene pair," *Mol Microbiol*, 31(4):1255-1264 (1999).

Maier, et al., "Hydrogen uptake hydrogenase in *Helicobacter pylori*," *FEMS Microbiol Lett*, 141(1):71-76 (1996).

Marcelli, et al., "The respiratory chain of *Helicobacter pylori*: identification of cytochromes and the effects of oxygen on cytochrome and menaquinone levels," *FEMS Microbiol Lett*, 138(1):59-64 (1996).

McAdams, HH and Arkin, A, "Simulation of Prokaryotic Genetic Circuits," *Annual Review of Biophysics and Biomolecular Structure*, 27:199-224 (1998).

McAlister-Henn L and Thompson, LM "Isolation and epxression of the gene encoding yeast mitochondrial malate dehydrogenase.," *J Bacteriol*, 169(11):5157-5166 (1987).

McGee; D.J., "*Helicobacter pylori* rocF is required for arginase activity and acid protection in vitro but is not essential for colonization of mice or for urease activity," *J Bacteriol*, 181(23):7314-7322 (1998).

Meldrum, "Automation for genomics, part one: preparation for sequencing," *Genome Res*, 10(8):1081-1092 (2000).

Mendes, P and Kell, D, "Non-linear optimization of biochemical pathways: Applications to metabolic engineering and parameter estimation," *Bioinformatics*, 14(10):869-883 (1998).

Mendz, et al., "Characterisation of glucose transport in *Helicobacter pylori*," *Biochim Biophys Acta*, 1244(2-3):269-276 (1995).

Mendz, et al., "Characterization of fumarate transport in *Helicobacter pylori*," *J Membr Biol*, 165(1):65-76 (1998).

Mendz, et al., "De novo synthesis of pyrimidine nucleotides by *Helicobacter pylori*,"*J Appl Bacteriol*, 77(1):1-8 (1994).

Mendz, et al., "In situ characterization of *Helicobacter pylori* arginase," *Biochim Biophys Acta*, 1388(2):465-477 (1998).

Mendz, et al., "Purine metabolism and the microaerophily of *Helicobacter pylori*," *Arch Microbiol*, 168(6):448-456 (1997).

Mendz, et al., "The Entner-Doudoroff pathway in *Helicobacter pylori*," *Arch Biochem Biophys*, 312(2):349-356 (1994).

Mendz, GL and Hazell SL, "Aminoacid utilization by *Helicobacter pylori*," *Int J Biochem Cell Biol*, 27(10):1085-1093 (1995).

Mendz, GL and Hazell, SL, "Glucose phosphorylation in *Helicobacter pylori*," *Arch Biochem Biophys*, 300(1):522-525 (1993).

Mendz, GL, et al., "Pyruvate metabolism in *Helicobacter pylori*," *Arch Microbiol*, 162(3):187-192 (1994).

Mewes, et al., "MIPS: A database for genomes and protein sequences," *Nucleic Acids Research*, 30(1):31-34 (2002).

Mitchell, "The GLN1 locus of *Saccharomyces cerevisiae* encodes glutamine synthetase," *Genetics*, 111(2):243-258 (1985).

Moszer, et al., "SubtiList: the reference database for the *Bacillus subtilis* genome," *Nucleic Acids Res*, 30(1):62-65 (2002).

Mulquiney, PJ and Kuchel, PW, "Model of 2,3-bisphosphoglycerate metabolism in the human erythrocyte based on detailed enzyme kinetic equations: computer simulation and metabolic control analysis," *Biochem J*, 342(Pt 3):597-604 (1999).

Murray, M and Greenberg, ML, "Expression of yeast INM1 encoding inositol monophosphatase is regulated by inositol, carbon source and growth stage and is decreased by lithium and valproate," *Mol Microbiol*, 36(3):651-661 (2000).

Nedenskov, "Nutritional requirements for growth of *Helicobacter pylori*," *Appl Environ Microbiol*, 60(9):3450-3453 (1994).

Nissen, et al., "Expression of a cytoplasmic transhydrogenase in *Saccharomyces cerevisiae* results in formation of 2-oxoglutarate due to depletion of the NADPH pool," *Yeast*, 18(1):19-32 (2001).

Nissen, et al., "Flux distributions in anaerobic, glucose-limited continuous cultures of *Saccharomyces cerevisiae*," *Microbiology*, 143(Pt 1):203-218 (1997).

Ogasawara, "Systematic function analysis of *Bacillus subtilis* genes," *Res Microbiol*, 151(2):129-134 (2000).

Oh, MK and Liao, JC, "Gene expression profiling by DNA microarrays and metabolic fluxes in *Escherichia coli*," *Biotech Prog*, 16:278-286 (2000).

Olsson, et al., "Separate and simultaneous enzymatic hydrolysis and fermentation of wheat hemicellulose with recombinant xylose utilizing *Saccharomyces cerevisiae*," *Appl Biochem Biotechnol*, 129-132:117-129 (2006).

Otto, et al., "A mathematical model for the influence of fructose 6-phosphate, ATP, potassium, ammonium and magnesium on the phosphofructokinase from rat erythrocytes," *Eur J Biochem*, 49(1):169-178 (1974).

Ouzounis, CA and Karp, PD, "Global Properties of the Metabolic Map of *Escherichia coli*," *Genome Res*, 10(4):568-576 (2000).

Overbeek, et al., "WIT: Integrated System for High-Throughput Genome Sequence Analysis and Metabolic Reconstruction" *Nucleic Acids Res*, 28(1):123-125 (2000).

Overkamp, et al., "In vivo analysis of the mechanisms for oxidation of cytosolic NADH by *Saccharomyces cerevisiae* mitochondria," *J Bacteriol*, 182(10):2823-2830 (2000).

Ozcan, S., Freidel, K., Leuker, A. & Ciriacy, M., "Glucose uptake and catabolite repression in dominant HTR1 mutants of *Saccharomyces cerevisiae.*," *J Bacteriol*, 175(17):5520-5528 (1993).

Pallotta, et al., "*Saccharomyces cerevisiae* mitochondria can synthesise FMN and FAD from externally added riboflavin and export them to the extramitochondrial phase," *FEBS Lett*, 428(3):245-249 (1998).

Palmieri, et al., "Identification and functions of new transporters in yeast mitochondria," *Biochim Biophys Acta*, 1459(2-3):363-369 (2000).

Palmieri, et al., "Identification of the yeast ACR1 gene product as a succinate-fumarate transporter essential for growth on thanol or acetate," *FEBS Lett*, 417(1):114-118 (1997).

Palmieri, et al., "Identification of the yeast mitochondrial transporter for oxaloacetate and sulfate," *J Biol Chem*, 274(32):22184-22190 (1999).

Palmieri, et al., "Yeast mitochondrial carriers: bacterial expression, biochemical identification and metabolic significance," *J Bioenerg Biomembr*, 32(1):67-77 (2000).

Palsson, "What Lies Beyond Bioinformatics," *Nat Biotechnol*, 15:3-4 (1997).
Papin, et al., "The genome-scale metabolic extreme pathway structure in Haemophilus influenzae shows significant network redundancy," *J Theor Biol*, 215(1):67-82 (2002).
Parks, "Metabolism of sterols in yeast," *CRC Crit Rev Microbiol*, 6(4):301-341 (1978).
Parks, et al., "Use of sterol mutants as probes for sterol functions in the yeast, *Saccharomyces cerevisiae*," *Crit Rev Biochem Mol Biol*, 34(6):399-404 (1999).
Paulsen, et al., "Unified inventory of established and putative transporters encoded within the complete genome of *Saccharomyces cerevisiae*," *FEBS Lett*, 430(1-2):116-125 (1998).
Pearson, et al., "Comparison of DNA Sequences With Protein Sequences," *Genomics*, 46(1):24-36 (1997).
Pennisi, "Laboratory Workhouse Decoded," *Science*, 277(5331):1432-1434 (1997).
Persson, et al., "Phosphate permeases of *Saccharomyces cerevisiae*: structure, function and regulation," *Biochim Biophys Acta*, 1422(3):255-272 (1999).
Peterson, et al., "The Comprehensive Microbial Resource," *Nucleic Acids Res*, 29(1):123-125 (2001).
Pharkya, et al., "Exploring the overproduction of amino acids using the bilevel optimization framework OptKnock," *Biotechnol Bioeng*, 84(7):887-899 (2003).
Phelps, et al., "Metabolomics and microarrays for improved understanding of phenotypic characteristics controlled by both genomics and environmental constraints," *Curr Opin Biotechnol*, 13(1):20-24 (2002).
Pitson, et al., "The tricarboxylic acid cycle of *Helicobacter pylori*," *Eur J Biochem*, 260(1):258-267 (1999).
Pramanik, J and Keasling, J, "Stoichiometric Model of *Escherichia coli* Metabolism: Incorporation of Growth-Rate Dependent Biomass Composition and Mechanistic Energy Requirements," *Biotechnol Bioeng*, 56(4):398-421 (1997).
Price, et al., "Determination of redundancy and systems properties of the metabolic network of *Helicobacter pylori* using genome-scale extreme pathway analysis," *Genome Res*, 12(5):760-769 (2002).
Price, et al., "Genome-scale models of microbial cells: evaluating the consequences of constraints," *Nat Rev Microbiol*, 2(11):886-897 (2004).
Price, et al., "Network-based analysis of metabolic regulation in the human red blood cell," *J Theor Biol*, 225(2):185-194 (2003).
Przybyla-Zawislak, et al., "Genes of succinyl-CoA ligase from *Saccharomyces cerevisiae*," *Eur J Biochem*, 258(2):736-743 (1998).
Qian, et al., "Ethanol production from dilute-Acid softwood hydrolysate by co-culture," *Appl Biochem Biotechnol*, 134(3):273-284 (2006).
Reed, et al., "An expanded genome-scale model of *Escherichia coli* K-12 (iJR904 GSM/GPR)," *Genome Biol*, 4(9):R54 (2003).
Reed, JL and Palsson, BO, "Thirteen years of building constraint-based in silico models of *Escherichia coli*" *J Bacteriol*, 185(9):2692-2699 (2003).
Regenberg, et al., "Substrate specificity and gene expression of the amino-acid permeases in *Saccharomyces cerevisiae*," *Curr Genet*, 36(6):317-328 (1999).
Remize, et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl Environ Microbiol*, 66(8):3151-3159 (2000).
Repetto, B and Tzagoloff, A, "In vivo assembly of yeast mitochondrial alpha-ketoglutarate dehydrogenase complex," *Mol Cell Biol*, 11(8):3931-3939 (1991).
Reynolds, DJ and Penn, CW, "Characteristics of *Helicobacter pylori* growth in a defined medium and determination of its amino acid requirements," *Microbiolog*, 140(Pt 10):2649-2656 (1994).
Rhee, et al., "Activation of gene expression by a ligand-induced conformational change of a protein-DNA complex," *J Biol Chem*, 273(18):11257-11266 (1998).
Saier, MH, "Genome sequencing and informatics: new tools for biochemical discoveries," *Plant Physiol*, 117(4):1129-1133 (1998).

Salgado, et al., "RegulonDB (version 3.2): transcriptional regulation and operon organization in *Escherichia coli* K-12," *Nucleic Acids Res*, 29(1):72-74 (2001).
Salmon, et al., "Global gene expression profiling in *Escherichia coli* K12. The effects of oxygen availability and FNR," *J Biol Chem*, 278(32):29837-29855 (2003).
Sauer, et al., "Metabolic Capacity of *Bacillus subtilis* for the Production of Purine Nucleosides, Riboflavin, and Folic Acid," *Biotechnol Bioeng*, 59(2):227-238 (1998).
Sauer, et al., "Metabolic flux ratio analysis of genetic and environmental modulations of *Escherichia coli* central carbon metabolism," *J Bacteriol*, 181(21):6679-6688 (1999).
Sauer, Uwe, "Evolutionary Engineering of Industrially Important Microbial Phenotypes," *Adv in Biochem Eng Biotechnol*, 73:129-169 (2001).
Savageau, "Biochemical systems analysis. I. Some mathematical properties of the rate law for the component enzymatic reactions," *J Theor Biol*, 25(3):365-369 (1969).
Schaaff-Gerstenschlager, I and Zimmermann, FK, "Pentose-phosphate pathway in *Saccharomyces cerevisiae*: analysis of deletion mutants for transketolase, transaldolase, and glucose 6-phosphate dehydrogenase," *Curr Genet*, 24(5):373-376 (1993).
Schaff, et al., "The Virtual cell" *Proceedings of the Pacific Symposium on Biocomputing*, 4:228-239 (1999).
Schilling, "On Systems Biology and the Pathway Analysis of Metabolic Networks," Department of Bioengineering, University of California, San Diego: La Jolla (2000).
Schilling, et al., "Genome-scale metabolic model of *Helicobacter pylori* 26695," *J Bacteriol*, 184(16):4582-4593 (2002).
Schneider, et al., "The *Escherichia coli* gabDTPC operon: specific gamma-aminobutyrate catabolism and nonspecific induction," *J Bacteriol*, 184(24):6976-6986 (2002).
Schuster, et al., "A general definition of metabolic pathways useful for systematic organization and analysis of complex metabolic networks," *Nature Biotechnol*, 18(3):326-332 (2000).
Schuster, et al., "Detection of elementary flix models in biochemical networks: a promising tool for pathway analysis and metabolic engineering," *Trends Biotechnol*, 17(2):53-60 (1999).
Schuster, S and Hilgetag, C, "On elementary flux modes in biochemical reaction systems at steady state," *J Biol Syst*, 2(2):165-182 (1994).
Schwikowski, et al., "A network of protein-protein interactions in yeast," *Nature Biotechnol*, 18(12):1257-1261 (2000).
Scott, et al., "The Pendred Syndrome Gene Encodes a Chloride-Iodide Transport Protein," *Nat Genet*, 21(4):440-443 (1999).
Selkov, et al., "Functional Analysis of Gapped Microbial Genomes: Amino Acid Metabolism of *Thiobacillus ferroxidans*," *Proc Natl Acad Sci U.S.A.*, 97(7):3509-3514 (2000).
Selkov, et al., "MPW: the metabolic pathways database," *Nucleic Acids Res*, 26(1):43-45 (1998).
Selkov, et al., "The metabolic pathway collection from EMP: the enzymes and metabolic pathways database," *Nucleic Acids Res*, 24(1):26-28 (1996).
Shen-Orr, et al., "Network motifs in the transcriptional regulation network of *Escherichia coli*," *Nat Genet*, 31(1):64-68 (2002).
Silve, et al., The immunosuppressant SR 31747 blocks cell proliferation by inhibiting a steriod isomerase in *Saccharomyces cerevisiae*, *Mol Cell Biol*, 16(6):2719-2727 (1996).
Skouloubris, et al., "The *Helicobacter pylori* UreI protein is not involved in urease activity but is essential for bacterial survival in vivo," *Infect Immun*, 66(9):4517-4521 (1998).
Smith, et al., "Functional analysis of the genes of yeast chromosome V by genetic footprinting.," *Science*, 274(5295):2069-2074 (1996).
Sorlie, et al., "Gene expression patterns of breast carcinomas distinguish tumor subclasses with clinical implications," *Proc Natl Acad Sci U.S.A.*, 98(19):10869-10874 (2001).
Stark, et al., "Amino acid utilisation and deamination of glutamine and asparagine by *Helicobacter pylori*," *J Med Microbiol*, 46(9):793-800 (1997).
Stephanopoulos, "Metabolic engineering," *Curr Opin Biotechnol*, 5(2):196-200 (1994).
Summers, et al., "*Saccharomyces cerevisiae* cho2 mutants are deficient in phospholipid methylation and cross-pathway regulation of inositol synthesis" *Genetics*, 120(4):909-922 (1988).

Swartz, "A PURE approach to constructive biology.," *Nat Biotechnol*, 19(8):732-733 (2001).

Syvanen, "Accessing genetic variation: Genotyping single nucleotide polymorphisms.," *Nat Rev Genet*, 2(12):930-942 (2001).

Szambelan, et al., "Use of *Zymomonas mobilis* and *Saccharomyces cerevisiae* mixed with *Kluyveromyces fragilis* for improved ethanol production from Jerusalem artichoke tubers," *Biotechnol Lett*, 26(10):845-848 (2004).

Tamayo, et al., "Interpreting patterns of gene expression with self-organizing maps: methods and application to hematopoietic differentiation," *Proc Natl Acad Sci U.S.A.*, 96(6):2907-2912 (1999).

Taniguchi, M and Tanaka, T, "Clarification of interactions among microorganisms and development of co-culture system for production of useful substances," *Adv Biochem Eng Biotechnol*, 90:35-62 (2004).

Tao, et al., "Engineering a homo-ethanol pathway in *Escherichia coli*: increased glycolytic flux and levels of expression of glycolytic genes during xylose fermentation," *J Bacteriol*, 183(10):2979-2988 (2001).

ter Linde, et al., "Genome-wide transcriptional analysis of aerobic and anaerobic chemostat cultures of *Saccharomyces cerevisiae*," *J Bacteriol*, 181(24):7409-7413 (1999).

Thomas, D and Surdin-Kerjan, Y, "Metabolism of sulfur amino acids in *Saccharomyces cerevisiae*," *Microbiol Mol Biol Rev*, 61(4):503-532 (1997).

Tomb, et al., "The complete genome sequence of the gastric pathogen *Helicobacter pylori*," *Nature*, 388(6642):539-547 (1997).

Tomita, et al., "E-Cell: Software Environment for Whole-Cell Simulation," *Bioinformatics*, 15(1):72-84 (1999).

Trotter, et al., "A genetic screen for aminophospholipid transport mutants identifies the phosphatidylinositol 4-kinase, STT4p, as an essential component in phosphatidylserine metabolism," *J Biol Chem*, 273(21):13189-13196 (1998).

Uetz, et al., "A comprehensive analysis of protein—protein interactions in *Saccharomyces cerevisiae*," *Nature*, 403(6770):623-627 (2000).

Van den Berg, MA and Steensma, HY, "ACS2, a *Saccharomyces cerevisiae* gene encoding acetyl-coenzyme A synthetase, essential for growth on glucose," *Eur J Biochem*, 231(3):704-713 (1995).

van Dijken, et al., "Alcoholic fermentation by 'non-fermentative' yeasts," *Yeast*, 2(2):123-127 (1986).

van Dijken, et al., "Kinetics of growth and sugar consumption in yeasts," *Antonie Van Leeuwenhoek*, 63(3-4):343-352 (1993).

Varma, A and Palsson, BO, "Metabolic capabilities of *Escherichia coli*. II: Optimal Growth Patterns.," *J Theor Biol*, 165:503-522 (1993).

Varma, A and Palsson, BO, "Metabolic capabilities of *Escherichia coli*: I. Synthesis of Biosynthetic Precursors and Cofactors," *J Theor Biol*, 165:477-502 (1993).

Varma, A and Palsson, BO, "Parametric sensitivity of stoichiometric flux balance models applied to wild-type *Escherichia coli* metabolism," *Biotechnol Bioeng*, 45(1):69-79 (1995).

Varma, A and Palsson, BO, "Predictions for Oxygen Supply Control to Enhance Population Stability of Engineered Production Strains," *Biotechnol Bioeng*, 43(4):275-285 (1994).

Varma, A and Palsson, BO, "Stoichiometric flux balance models quantitatively predict growth and metabolic by-product secretion in wild-type *Escherichia coli* W3110," *Appl Environ Microbiol*, 60(10):3724-3731 (1994).

Varma, et al., "Biochemical Production Capabilities of *Escherichia coli*," *Biotechnol Bioeng*, 42(1):59-73 (1993).

Varma, et al., "Stoichiometric Interpretation of *Escherichia coli* Glucose Catabolism Under Various Oxygenation Rates.," *Appl Environ Microbiol*, 59(8):2465-2473 (1993).

Varner, J and Ramkrishna, D, "Mathematical Models of Metabolic Pathways," *Curr Opin Biotechnol*, 10(2):146-150 (1999).

Velculescu, et al., "Analysing uncharted transcriptomes with SAGE," *Trends Genet*, 16(10):423-425 (2000).

Verduyn, "Physiology of yeasts in relation to biomass yields," *Antonie Van Leeuwenhoek*, 60(3-4):325-353 (1991).

Verduyn, et al., "A theoretical evaluation of growth yields of yeasts," *Antonie Van Leeuwenhoek*, 59(1):49-63 (1991).

Verduyn, et al., "Energetics of *Saccharomyces cerevisiae* in anaerobic glucose-limited chemostat cultures," *J Gen Microbiol*, 136:405-412 (1990).

Vissing, et al., "Paradoxically Enhanced Glucose Production During Exercise in Humans with Blocked Glycolysis Caused by Muscle Phosphofructokinase Deficiency," *Neurology*, 47(3):766-771 (1996).

Wang, et al., "Computer-aided baker's yeast fermentations," *Biotechnol and Bioeng*, 19(1):69-86 (1977).

Wang, et al., "Computer control of bakers' yeast production," *Biotechnol and Bioeng*, 21:975-995 (1979).

Wen, et al., "Large-scale temporal gene expression mapping of central nervous system development," *Proc Natl Acad Sci U.S.A.*, 95(1):334-339 (1998).

Wiback, SJ and Palsson, BO, "Extreme pathway analysis of human red blood cell metabolism," *Biophys J*, 83:808-818 (2002).

Wieczorke, et al., "Concurrent knock-out of at least 20 transporter genes is required to block uptake of hexoses in *Saccharomyces cerevisiae*," *FEBS Lett*, 464(3):123-128 (1999).

Wingender, et al., "The TRANSFAC system on gene expression regulation," *Nucleic Acids Res*, 29(1):281-283 (2001).

Wong, P., et al., "Mathematical Model of the Lac Operon: Inducer Exclusion, Catabolite Repression, and Diauxic Growth on Glucose and Lactose," *Biotechnol Prog*, 13(2):132-143 (1997).

Xie, L and Wang, D, "Integrated Approaches to the Design of Media and Feeding Strategies for Fed-Batch Cultures of Animal Cells," *Trends Biotechnol*, 15(3):109-113.

Yamada, et al., "Effects of common polymorphisms on the properties of recombinant human methylenetetrahydrofolate reductase," *Proc Natl Acad Sci U.S.A.*, 98(26):14853-14858 (2001).

Yeung, et al., "Reverse engineering gene networks using singular value decomposition and robust regression," *Proc Natl Acad Sci U.S.A.*, 99(9):6163-6168 (2002).

Yeung, et al., *Bioinformatics*, "Model-based clustering and data transformations for gene expression data," 17(10):977-87 (2001).

Yoshida, et al., "Combined transcriptome and proteome analysis as a powerful approach to study genes under glucose repression in *Bacillus subtilis*," *Nucleic Acids Res*, 29(3):683-692 (2001).

Zanella, A and Bianchi, P, "Red cell pyruvate kinase deficiency: from genetics to clinical manifestations," *Bailliere's Best Pract Res Clin Haematol* 13(1):57-81 (2000).

Zhu, J and Zhang, MO, "SCPD: a promoter database of the yeast *Saccharomyces cerevisiae*," *Bioinformatics*, 15(7-8):607-611 (1999).

Zweytick, et al., "Biochemical characterization and subcellular localization of the sterol C-24(28) reductase, erg4p, from the yeast *Saccharomyces cerevisiae*," *FEBS Lett*, 470(1):83-87 (2000).

URL Genome.jp Website, KEGG *Bacillus subtillis*, 1-7 (2005).

Savinell and Palsson, "Network Analysis of Intermediary Metabolism using Linear Optimization. II. Interpretation of Hybridoma Cell Metabolism," *J. Theor. Biol.* 154:455-473 (1992).

Savinell and Palsson, "Network Analysis of Intermediary Metabolism using Linear Optimization. I. Development of Mathematical Formalism," *J. Theor. Biol.* 154:421-454 (1992).

Xie and Wang, "Energy Metabolism and ATP Balance in Animal Cell Cultivation Using a Stoichiometrically Based Reaction Network," *Biotech. Bioeng.* 52:591-601 (1996).

Xie and Wang, "Material Balance Studies on Animal Cell Metabolism Using a Stoichiometrically Based Reaction Network," *Biotech. Bioeng.* 52:579-590 (1996).

Benjamini and Hochberg, "Controlling the false Discovery Rate: a Practical and Powerful Approach to Multiple Testing," *J Roy Stat Soc Ser B (Methodological )*, 57:289-300 (1995).

Chadha, et al., "Simultaneous saccharification and fermentation of rice straw into ethanol," *Acta Microbiol Immunol Hung.*, 42(1):71-75 (1995).

Christensen, B and Nielsen, J, "Metabolic network analysis. A powerful tool in metabolic engineering," *Advances in Biochemical Engineering/Biotechnology*, 66:209-231 (2000).

Clarke, *Stability of Complex Reaction Networks. Advances in Chemical Physics*, 43:1-125 (1980).

Cover, TL and Blaser, MJ, "*Helicobacter pylori* infection, a paradigm for chronic mucosal inflammation: pathogenesis and implications for eradication and prevention," *Adv Intern Med*, 41:85-117 (1996).

Dooley, et al., "An all D-amino acid opiod peptide with central analgesic activity from a combinatorial library," *Science*, 266(5193):2019-2022 (1994).

Fleischmann, "Whole-genome random sequencing and assembly of *Haemophilus influenzae* Rd," *Science*, 269(5223):496-512 (1995).

Ge, et al., "Cloning and functional characterization of *Helicobacter pylori* fumarate reductase operon comprising three structural genes coding for subunits C, A and B," *Gene*, 204(1-2):227-234 (1997).

Kelly, "The physiology and metabolism of the human gastric pathogen *Helicobacter pylori*," *Adv Microb Physiol*, 40:137-189 (1998).

Mahadevan, R and Schilling, CH, "The effects of alternate optimal solutions in constraint-based genome-scale metabolic models," *Metab Eng*, 5(4):264-276 (2003).

Marshall, B.J and Warren, J.R., "Unidentified curved bacilli in the stomach of patients with gastritis and peptic ulceration," *Lancet*, 1(8390):1311-1315 (1984).

McAdams, HH and Shapiro, L, "Circuit simulation of genetic networks." *Science*, 269(5224):650-656 (1995).

Mendz, et al., "Fumarate reductase: a target for therapeutic intervention against *Helicobacter pylori*," *Arch Biochem Biophys*, 321(1):153-159 (1995).

Mendz, et al., "Glucose utilization and lactate production by *Helicobacter pylori*," *J Gen Microbiol*, 139(12):3023-3028 (1993).

Mendz, GL and Hazell, SL, "Fumarate catabolism in *Helicobacter pylori*," *Biochem Mol Biol Int*, 31(2):325-332 (1993).

Mendz, GL, et al., "Salvage synthesis of purine nucleotides by *Helicobacter pylori*," *J Appl Bacteriol*, 77(6):674-681 (1994).

Patel, BN and West, TP, ",Degradation of the pyrimidine bases uracil and thymine by *Escherichia coli* B" *Microbios*, 49(199):107-113 (1987).

Ren, et al., "Genome-wide location and function of DNA binding proteins,"*Science*, 290(5500):2306-2309 (2000).

Schena, et al., "Quantitative monitoring of gene expression patterns with a complementary DNA microarray," *Science*, 270(5235):467-470 (1995).

Sedivy, JM and Fraenkel, DG, "Fructose bisphosphatase of *Saccharomyces cerevisiae*. Cloning, disruption and regulation of the FBP1 structural gene.," *J Mol Biol*, 186(2):307-319 (1985).

Selkov, et al., "A reconstruction of the metabolism of *Methanococcus jannaschii* from sequence data.," *Gene*, 197(1-2):GC11-26 (1997).

Sherlock, et al., "Analysis of large-scale gene expression data," *Curr Opin Immunol*, 12:201-205 (2000).

Shipston, N. And Bunch, AW, "The physiology of L-methionine catabolism to the secondary metabolite ethylene by *Escherichia coli,* "*J Gen Microbiol*, 135(6), 1489-1497 (1989).

Stephanopoulos, "Metabolic Engineering," *Biotechnol Bioeng*, 58(2-3):119-120 (1998).

Tanaka, KR and Zerez, CR, "Red cell enzymopathies of the glycolytic pathway," *Semin Hematol*, 27(2):165-185 (1990).

Venter, et al., "Shotgun sequencing of the human genome," *Science*, 280(5369):1540-1542 (1998).

Waterston, R and Sulston, JE, "The Human Genome Project: reaching the finish line," *Science*, 282(5386):53-54 (1998).

Wills, C and Melham, T, "Pyruvate carboxylase deficiency in yeast: a mutant affecting the interaction between the glyoxylate and Krebs cycles.," *Arch Biochem Biophys*, 236(2):782-791 (1985).

Winzeler, et al., "Functional characterization of the *S. cerevisiae* genome by gene deletion and parallel analysis," *Science*, 285(5429):901-906 (1999).

Zeng, et al., "Use of respiratory quotient as a control parameter for optimum oxygen supply and scale-up of 2,3-butanediol production under microaerobic conditions," *Biotechnol Bioeng*, 44(9):1107-1114 (1994).

Zigova, "Effect of RQ and pre-seed conditions on biomass and galactosyl transferase production during fed-batch culture of *S. cerevisiae* BT150", *J. Biotechnol.* 80(1):55-62 (2000).

Akutsu, "Genetic Network Interference Algorithm," Mathematical Science (Sur-Kagaku) *Science* 37(6):40-46 (1999).

Aristidou and Penttila "Metabolic engineering applications to renewable resource utilization," *Curr. Opin. Biotech.* 11(2)187-198 (2000).

Beard, et al., "Energy Balance for Analysis of Complex Metabolic Networks," *Biophys. J.* 83(1):79-86 (2002).

Callis, "Regulation of Protein Degradation," *Plant Cell* 7:845-857 (1995).

Carrier and Keasling, "Investigating Autocatalytic Gene Expression Systems through Mechanistic Modeling," *J. Theor. Bio.l* 201(1):25-36 (1999).

Chartrain, et al., "Metabolic engineering and directed evotion for the production of pharmaceuticals," *Curr. Opin. Biotech.* 11(2):209-214 (2000).

Dafoe, et al., "In Silico Knowledge Discovery Biomedical databases," *Proceedings of the SPIE Fifth Workshop on Neural Networks*, San Francisco, Nov. 7-10, 1993.

DeRisi, et al., "Use of cDNA microarray to analyse gene expression patters in human cancer," *Nat. Gene.* 14:457-460 (1996).

Duarte, et al., "Reconstruction and validation of *Saccharomyces cerevisiae* iND750, a fully compartmentalized genome-scale metabolic model," *Genome Res*.14(7):1298-1309 (2004).

Feist and Palsson, "The growing scope of applications of genome-scale metabolic reconstructions using *Escherichia coli,*" *Nat. Biotech.* 26(6):659-667 (2008).

Fotheringham, "Engineering biosynthetic pathways: new routes to chiral amino acids," *Curr. Opin. Chem. Biology.* 4(1):120-124 (2000).

Gombert and Nielsen, "Mathematical modeling of metabolism," *Curr. Opin. Biotech.* 11(2):180-186 (2000).

Guardia, et al., "Cybernetic modeling and regulation of metabolic pathways in multiple steady states of hybridoma cells," *Biotech. Prog.* 16(5):847-853 (2000).

Kaufman, et al., "Towards a logical analysis of the immune response," *J Theor. Biology* 114(4):527-561 (1985).

Kunst and Devine "The project of sequencing the entire *Bacillus substilis* genome," *Res. Microbiol.* 142:905-912 (1991).

Lee, et al., "Incorporating qualitative knowledge in enzyme kinetic models using fuzzy logic," *Biotech. Bioeng.* 62(6):722-729 (1999).

Lynd, et al., "Biocommodity Engineering," *Biotech. Prog.* 15:777-793 (1999).

McAdams and Shapiro, "Circuit simulation of genetic networks," *Science* 269:651-656 (1995).

McAdams and Arkin "Stochastic mechanisms in gene expression," *Proc. Natl. Acad. Sci. U.S.A.* 94(3):814-819 (1997).

McAdams and Arkin, "It's a noisy business! Genetic regulation at the nanomolar scale," *Trends Genet.* 15(2):65-69 (1999).

Ostergaard, et al., "Increasing galactose consumption by *Saccharomyces cerevisiae* through metabolic engineering of the GAL gene regulatory network," *Nat. Biotech.* 18:1283-1286 (2000).

Pieper and Reineke, "Engineering bacteria for bioremediation," *Curr. Opin. Biotech.* 11(3):262-270 (2000).

Raclot et al., "Selective release of human adipocyte fatty acids according to molecular structure," *Biochem. J.* 324 (Pt3):911-915 (1997).

Rao, C and Arkin, A, "Control motifs for intracellular regulatory networks," *Annu. Rev. Biomed. Eng.* 3:391-419 (2001).

Savageau, "Development of fractal kinetic theory for enzyme-catalysed reactions and implications for the design of biochemical pathways," *Biosystems* 47(1-2):9-36 (1998).

Somogyi and Sniegoski, "Modeling the complexity of genetic networks: understanding the multigenic and pleitropic regulation," *Complexity* 1(6):45-63 (1996).

Tandeitnik, et al., "Modeling of biological neurons by artificial neural networks," *Nineteenth Convention of Electrical and Electronics Engineers in Israel, Jerusalem, Israel, New York, NY, USA*, pp. 239-242 (1996).

Thieffry and Thomas, "Dynamical behavior of biological regulatory networks II. Immunity control in *Bacteriophage lambda*," *Bull. Math Biol.* 57(2):277-297 (1995).

Varner, "Large-scale prediction of phenotype: concept," *Biotech. Bioeng.* 69(6):664-678 (2000).

Vaseghi, et al., "In vivo Dynamics of the pentose phosphate pathway in *Saccharomyces cerevisiae*," *Metab. Eng.* 1:128-140 (1999).

Vo, et al., "Reconstruction and functional characterization of the human mitochondrial metabolic network abased on proteomic and biochemical data," *J. Biol. Chem.* 279(38):39532-39540 (2004).

URL www.i-sis.org.uk/WITBRL.php; Hoppert, M. (2004).

Five pages from URL: web.archive.org/web/20050731094028/ http://www.chem.qmw.ac.uk/iubmb/enzyme/ Enzyme Nomenclature database maintained by G. P. Moss of Queen Mary and Wesffield Colege in the United Kingdom; Date Obtained May 15, 2009.

Three pages from URL: web.archive.org/web/19981206132808/ http://ecocyc.panbio.com/ecocyc/ecocyc.html; Ecocyc; obtained on Sep. 18, 2009.

URL web.archive.org/web/20041208001518/http://www.enzobio.com/lifesci_index.htm, Enzo BioArray Terminal Labeling Kit protocol. (As printed on Sep, 18, 2009).

URL genetics.wisc.edu/, *E. coli* Genome Project at the University of Wisconsin. As printed on Sep. 18, 2009).

URL web.archive.org/web/20071228124426rn_1/www.genome.ad.jp/kegg/, Kyoto Encyclopedia of Genes and Genomes database (KEGG). (As printed on Sep. 18, 2009).

URL genome.tugraz.at/Software/Genesis/Description.html, "Genesis" software. (As printed on Sep. 18, 2009).

Six pages from URL: web.archive.org/web/2005025215224/ genome-www.stanford.edu/~sherlock/cluster.html, "XCluster" software: obtained on Sep. 18, 2009.

Home page from URL: web.archive.org/web/20050201083239/ igweb.integratedgenomics.com/MPW/, Metabolic pathways database (MPW), obtained Sep. 18, 2009.

URL integratedgenomics.com, ERGO from Integrated Genomics. (As printed on Sep. 18, 2009).

Three pages from URL: web.archive.org/web/2007001095540/ http://mips.gsf.de/proj/yeast/pathways on Jun. 6, 2008. MIPS, website:Comprehensive Yeast Genome Database—Pathways; Date Obtained Sep. 18, 2009.

Two pages from URL: www.ncbi.nlm.nih.gov/sites/ entrz?db=genome obtained on Jun. 15, 2009.

URL ncbi.nlm.nih.gov/projects/LocusLink/, LocusLink database maintained by the NCBI. (As printed on Sep. 18, 2009).

URL ncbi.nlm.nih.gov/Taxonomy/taxonomyhome.html/. (As printed on Sep. 18, 2009).

URL nslij-genetics.org/search_omim.html, Online Mendelian Inheritance in Man database, Center for Medical Genetics, Johns Hopkins University (Baltimore, MD) and National Center for Biotechnology Information, National Library of Medicine (Bethesda, MD). (As printed on Sep. 18, 2009).

URL qiagen.com, Qiagen RNeasy Mini Kit. (As p rinted on Sep. 18, 2009).

URL rana.lbl.gov/EisenSoftware.htm, "Cluster" software. (As printed on Sep. 18, 2009).

Home page from URL: web.archive.org/web/20070228190312/ http://systemsbiology.ucsd.edu, obtained on Sep. 18, 2009.

Two pages from URL: web.archive.org/web/20060712190022/ http://www.tigr.org/. The Institute for Genome Research, J. Craig Venter Institute; obtained on Sep. 18, 2009.

Home page from URL: web.archive.org/web/20021126044821/ http://tula.cifn.unam.mx:8850/regulondb/regulon_intro.frameset; obtained on Sep. 18, 2009.

Home pagefrom URL: web.archive.org/web/20041125063300/ http://wit.acs.anl.org; What is There (WIT), Obtained Nov. 23, 2008.

URL workbench.sdsc.edu/ Biology Workbench. (As printed on Sep. 18, 2009).

\* cited by examiner

Associated Object Model

The following classes participate in the creation of Gene-Protein Associations:
- Peptide
- PeptideProteinAssociation
- Protein The following classes participate in the creation of Protein-Reaction Associations:
- Protein
- ProteinReactionAssociation
- ModelReaction

Associated Database schema

SYSTEMS AND METHODS FOR CONSTRUCTING GENOMIC-BASED PHENOTYPIC MODELS

BACKGROUND OF THE INVENTION

This invention relates generally to simulation modeling and, more specifically, to computational methods for simulating and predicting the activity of biochemical and biological network models.

Therapeutic agents, including drugs and gene-based agents, are being rapidly developed by the pharmaceutical industry with the goal of preventing or treating human disease. Dietary supplements, including herbal products, vitamins and amino acids, are also being developed and marketed by the nutraceutical industry. Because of the complexity of biochemical reaction networks, even relatively minor perturbations caused by a therapeutic agent or a dietary component on the abundance or activity of a particular target, such as a metabolite, gene or protein, can affect hundreds of biochemical reactions. These perturbations can lead to desirable therapeutic effects, such as cell stasis or cell death in the case of cancer cells or other pathologically hyperproliferative cells. However, these perturbations can also lead to undesirable side effects, such as production of toxic byproducts.

Traditionally the identification of drugs and nutraceuticals has relied upon early stage screening and testing in which the effects of candidate drugs on individual genes or gene products are observed. This approach, although helpful for identifying a particular gene or gene product as a target for a particular disease, is often incapable of identifying the effects that the candidate drug or the drug inhibited target will have on other molecular components of the cell or organism. It is often not until late stage testing with human subjects that unwanted or even dangerous side effects are observed. Failure to select a candidate drug in early stage testing that is without side effects can result in harm to individuals participating in clinical trials and significant delays in curing individuals suffering from disease due to pursuing the wrong drug.

In order to design effective methods of repairing, engineering or disabling cellular activities, it is essential to understand cellular behavior from an integrated perspective. Methods have recently been developed to reconstruct biological reaction networks that occur within organisms, with the goal of being able to model them and then use simulation to predict and analyze organismal behavior. One of the most powerful current approaches to modeling complex biological reaction networks involves constraints-based modeling. This approach provides a mathematically defined solution space wherein all possible behaviors of the reconstructed biological reaction network must lie. The solution space can then be explored to determine the range of capabilities and preferred behavior of the biological system under various conditions.

A combination of many high throughput technologies is now providing information on a scale that includes entire genomes, the complete set of gene products encoded by the genomes, and molecular functions that occur in a cell or organism. The ability to create genome scale constraints-based models requires that vast amounts of biological information be assimilated. Although genome scale models have been produced for a variety of organisms and have been shown to accurately predict a number of cell functions, it is currently difficult and time consuming to build new models and many organisms for which genome scale information is available currently lack genome scale models. Furthermore, it is currently difficult to view the content of models and to cross-reference the information in the models with the information available in biological databases and with other models. Thus, for many models, errors go unnoticed or are difficult to correct once the model is built.

Thus, there exists a need for constraints-based models for the increasing number and variety of organisms for which genomes are being sequenced. A need also exists for methods to efficiently build and modify existing constraints-based models. The present invention satisfies these needs and provides related advantages as well.

SUMMARY OF THE INVENTION

The invention provides a computer implemented process for constructing a scalable output network model of a bioparticle. The process includes computer implemented steps of: (a) accessing a database of network gene components comprising an annotated network set of open reading frames (ORFs) of a bioparticle genome; (b) forming a data structure associating the network gene components with network reaction components, the data structure establishing a data set specifying a network model of connectivity and flow of the network reaction components, and (c) transforming the data set into a mathematical description of reactant fluxes defining the network model of connectivity and flow, wherein the mathematical description defines a scalable output network model of a bioparticle.

The invention further provides a computer implemented process for constructing a scalable phenotypic output network model. The process includes the computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components; (c) modifying the data set to enumerate a biochemical demand on the specified network model, and (d) transforming the modified data set into a mathematical description of reactant fluxes defining the network model of connectivity and flow, wherein the enumerated biochemical demand corresponds to an aggregate reactant demand flux defining a phenotypic output of the network model of a bioparticle.

Also provided is a computer implemented process for self-optimizing a network model of a bioparticle. The process includes the computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components; (c) transforming the data set into a mathematical description of reactant fluxes defining the network model of connectivity and flow; (d) determining the competence of the connectivity and flow within the network model, the competence indicating underinclusion or overinclusion of network reaction component content of the network model, and (e) identifying an ameliorating network reaction component capable of augmenting the competence of the network model, incorporation of the ameliorating network reaction component into the data structure producing a modified data structure specifying in an optimized network model of the bioparticle.

The invention also provides a computer implemented process for constructing a data structure specifying a network model of a bioparticle. The process includes the computer implemented steps: (a) accessing a database of network gene components including an annotated network set of open reading frames (ORFs) of a bioparticle genome; (b) selecting an ORF from the annotated network set encoding a gene product having a network reaction function; (c) determining the occurrence of a constituent gene product for the selected encoded gene product; (d) determining the occurrence of an additional gene product participating in the network reaction; (e) forming a data structure from the selected and determined gene products, the data structure associating the network gene components and network reaction components comprising cognate ORFs, encoded gene products, network reactions and reaction constituents, and (f) repeating steps (a)-(e) selecting another ORF from the annotated network set until substantially all of the network gene components of the annotated network set have been surveyed for encoding a gene product having a network reaction function to produce a data structure establishing a data set specifying a network model of connectivity and flow. The invention further provides computer systems having executable instructions for carrying out these computer implemented processes.

A system for constructing a scalable output network model of a bioparticle, including: (a) an input data set of network gene components including an annotated network set of open reading frames (ORFs) of a bioparticle genome; (b) executable instructions forming a data structure associating the network gene components with network reaction components, the data structure establishing a data set specifying a network model of connectivity and flow of the network reaction components; (c) executable instructions determining the occurrence of a reaction component satisfying a macro requirement deficiency in structural architecture of the network model, inclusion of an identified reaction component satisfying the macro requirement deficiency in the data structure supplementing the connectivity and flow of the network model; (d) a heuristic logic decision algorithm determining confidence of the network reaction components within the data structure, and (e) executable instructions mathematically describing from the data set reactant fluxes defining the network model of connectivity and flow, wherein the mathematical description defines a scalable output network model of a bioparticle. A system for constructing a scalable phenotypic output network model of a bioparticle, including: (a) an input data set of network gene components including an annotated network set of open reading frames (ORFs) of a bioparticle genome; (b) executable instructions forming a data structure associating the network gene components with network reaction components, the data structure establishing a data set specifying a network model of connectivity and flow of the network reaction components; (c) executable instructions modifying the data set to enumerate a biochemical demand on the specified network model, and (d) executable instructions mathematically describing from the modified data set reactant fluxes defining the network model of connectivity and flow, wherein the enumerated biochemical demand corresponds to an aggregate reactant demand flux defining a phenotypic output of the network model of said bioparticle. A system for constructing a self-optimizing network model of a bioparticle, including: an input data set of network gene components including an annotated network set of open reading frames (ORFs) of a bioparticle genome; executable instructions forming a data structure associating said network gene components with network reaction components, said data structure establishing a data set specifying a network model of connectivity and flow of said network reaction components; executable instructions mathematically describing from said data set reactant fluxes defining said network model of connectivity and flow; executable instructions computing competence of said connectivity and flow within said network model, said competence indicating underinclusion or overinclusion of network reaction component content of said network model, and executable instructions augmenting said competence of said connectivity and flow within said network model, said executable instructions specifying inclusion or exclusion of an ameliorating network reaction component, wherein incorporation of said ameliorating network reaction component into said data structure produces a modified data structure specifying an optimized network model of said bioparticle.

DETAILED DESCRIPTION OF THE INVENTION

Figure 1:
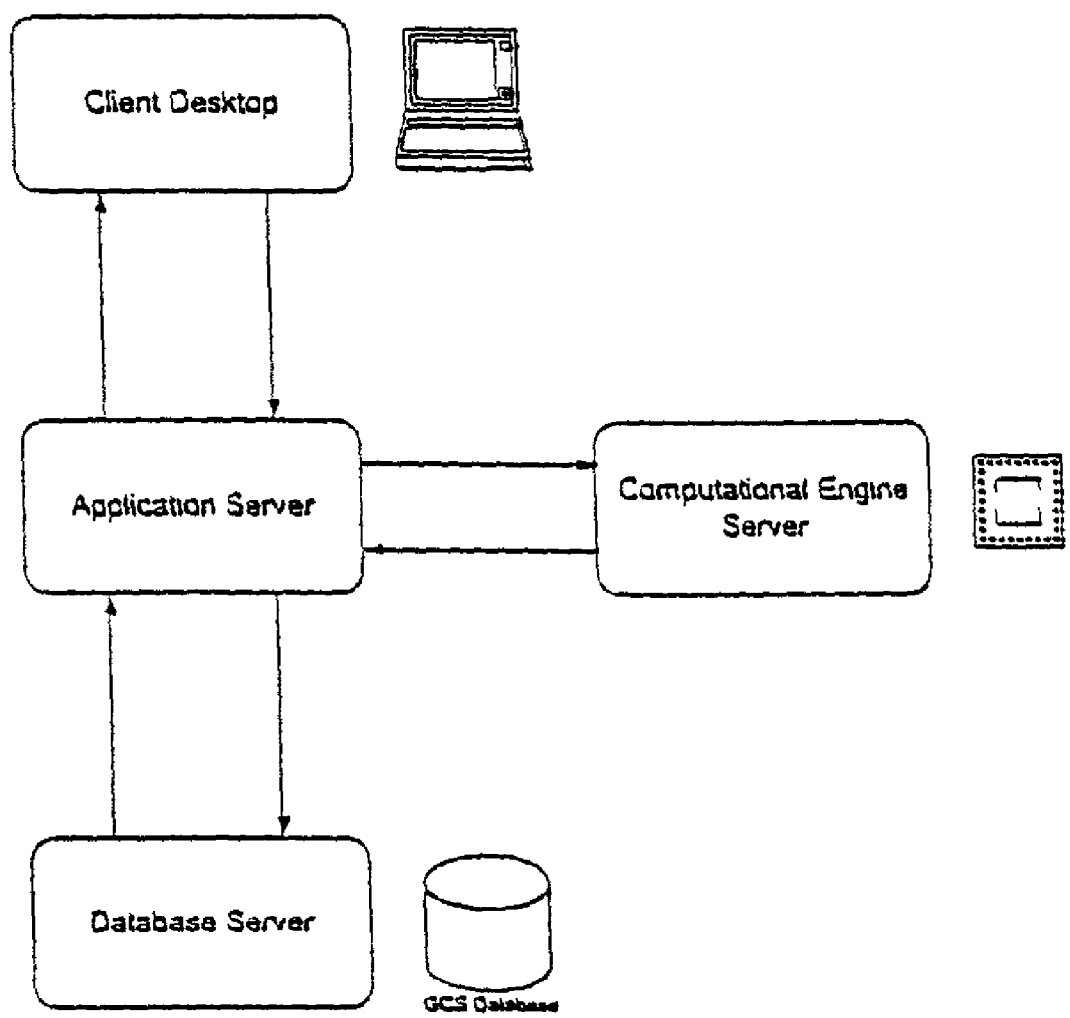
FIG. 1 shows an exemplary system architecture for a computer system of the invention.

Computer systems and computer implemented processes for constructing and using a network model of a bioparticle are described. In the following description, for the purposes of explanation, specific details are set forth in order to provide a thorough understanding of the present invention. Those skilled in the art will understand that the present invention can be practiced without these specific details and can be applied to any of a variety of related systems. For example, although the methods are described in the context of metabolic reactions it is understood that similar models can be made and used for simulation of other network systems such as biological regulatory systems, biological signal transduction systems and non-biological reaction systems.

In one embodiment, a network model of the invention can be used in silico to simulate the flux of mass, energy or charge through the chemical reactions of a biological system to define a solution space that contains any and all possible functionalities of the chemical reactions in the system, thereby determining a range of allowed activities for the biological system. Such an approach is referred to as constraints-based modeling because the solution space is defined by constraints such as the known stoichiometry of the included reactions as well as reaction thermodynamic and capacity constraints associated with maximum fluxes through reactions. Using a network model of the invention, the space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities.

In another embodiment, the constraints-based method is flux balance analysis. Flux balance analysis is based on flux balancing in a steady state condition and can be performed as described in Varma and Palsson, *Biotech. Bioeng.* 12:994-998 (1994). Flux balance approaches can be applied to reaction networks to simulate or predict systemic properties of adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *E. coli* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

Once the solution space has been defined, it can be analyzed to determine possible solutions under various conditions. This is an approach that is consistent with biological realities. Biological systems have built in flexibility and can, therefore, reach the same result in many different ways. These systems are designed through evolutionary mechanisms that have been restricted by fundamental constraints that all living systems must face. The constraints-based modeling strategy embraces these general realities.

For a reaction network that is defined for a particular organism through the use of genome sequence and biochemical and physiological data, the solution space describes the functional capabilities of the organism as described, for example, in WO 00/46405. Genome scale models have been created for a number of organisms including *Escherichia coli* (Edwards et al., *Proc. Natl. Acad. Sci. USA* 97:5528-5533 (2000)), *Haemophilus influenzae* (Edwards et al., *J. Biol. Chem.* 274: 17410-17416 (1999)), *Bacillus subtilis* and *Helicobacter pylori*.

The ability to continuously impose further restrictions on a network model via the tightening of constraints results in a reduction in the size of the solution space, thereby enhancing the precision with which physiological performance or phenotype can be predicted. This approach provides a basis for understanding and ultimately predicting the structure and function of a biological system through the model building and implementation process as set forth below.

As used herein, the term "scalable" is intended to mean that the content size of a network model of the invention can increase without substantial diminution in model performance where performance is a measure of model predictability. In general, the performance of a network model will increase proportionally to the accuracy of content elements included in the model. Although the number of calculations can increase with increase in content size, the predictability for obtaining a particular solution for a scalable network model of the invention will not be substantially diminished due to changes in content size alone. Network model content that can be increased includes, for example, data elements specifying gene component and network reaction components. The scalable network models of the invention also includes, for example, increasing network model content from a simple system of gene and network reaction components to complex, multisystem gene and network reaction components, to network gene and reaction components specifying complex cell and multicellular systems without substantial diminution in model performance. A specific example of maintaining network model performance while increasing model content would be increasing the model content of a gene to that specifying substantially all biochemical reactions derived from a cellular genome. Therefore, the term includes the ability of a network model to expand the number of ORFS, reactions, reactants and fluxes without requiring manipulations to the model programming, design or software architecture.

As used herein, the term "bioparticle" is intended to mean a biological entity that contains a nucleic acid genome that encodes constituent parts of the entity. The nucleic acid genome can be, for example, DNA or RNA and can be derived from a naturally occurring biological entity, a non-naturally occurring biological entity or designed de novo. A biological entity included in the term can be, for example, a virus or a cell, such as a procaryotic cell or eucaryotic cell or other naturally occurring or non-naturally occurring biological entities. A cell can be derived from a unicellular organism or from a multicellular organism.

As used herein, the term "phenotype," when used in reference to a network model, is intended to mean the detectable characteristics resulting from the interaction of a model genotype and a model environment. A detectible characteristic refers to a computed individual or integrated function of one or more network model components. Network models of the invention simulate, in silico, an organism or a functional set of interactive components of an organism. A model genotype contains those network gene components included in a network model specifying an in silico organism. A model environment includes, for example, a specified external condition exposed to an in silico organism. Therefore, a phenotype of a network model is a detectable result of the functional interactions of gene products encoded in the model genotype, and related reaction components, and the environmental conditions which influence the activity and interactions of network model components. A "phenotypic output" as it is used herein, refers to the measure of a characteristic resulting from simulation of a network model, or from simulation of a particular solution to a network model. A phenotypic output can be, for example, a solution space of a network model where the model environment consists all possibilities, a feasible solution where the model environment consists of constrained fluxes of external components, or a particular solution where the model environment consists of defined components.

As used herein, the term "network" is intended to mean a system of interconnected or interrelated components. The interconnections and interrelations can be, for example, either physical or functional relationships of system components. Therefore, the term refers to an aggregation or assemblage of system components and the relative relationships that define inclusion of components within such a system. One example of a network can be a computational representation of genes, gene products, reactants, functions and physicochemical characteristics, for example, that constitute an in silico organism of the invention. Another example of a network can be a computational representation of a genes, gene products, reactants, functions and physicochemical characteristics, for example, that constitute a biochemical network or a biochemical pathway of an in silico organism. Such biochemical networks can include, for example, central metabolism, peripheral metabolism, protein biosynthesis, carbohydrate biosynthesis, lipid biosynthesis and signal transduction. Biochemical pathways can include, for example, glycolysis, the citric acid (TCA) cycle, amino acid biosynthesis, nucleoside and nucleotide biosynthesis, a signal transduction event, and the like. Numerous other examples of reactions or events that combine into networks and pathways to produce a common function are well known to those skilled in the art and are included within the meaning of the term. Such networks and pathways can be found described in, for example, Stryer, L., *Biochemistry*, W. H. Freeman and Company, New York, 4th Edition (1995); Alberts et al., *Molecular Biology of The Cell*, Garland Publishing, Inc., New York, 2nd Edition (1989); Kuby, *Immunology*, 3rd Edition, W. H. Freeman & Co., New York (1997), Kornberg and Baker, *DNA Replication*, W. H. Freeman and Company, New York, 2nd Edition (1992), all of which are incorporated herein by reference. Therefore, regardless of the label used or the number of constituent elements, a network refers to a collection of components that exhibit a logical physical or functional relationship whose concerted interaction are employed for at least one common purpose.

As used herein, the term "component" or "network component" is intended to mean a data element, data set or electronic representation of a chemical or biochemical molecular entity in a network model of the invention. The term is intended to refer to the input and output representations as well as to the code and electronic representations within a computer program or processor. Therefore, representations of components of a system and their interrelationships will depict a network model of the invention. A variety of formats well known to those skilled in the art can be used to represent any or all types of chemical and biochemical components within a network model. The term can include, for example, a gene component, a reaction component or a non-gene component.

As used herein, the term "gene component" is intended to mean a data element, data set or electronic representation of a nucleic acid that encodes a gene product, or functional fragment thereof. A gene component can be represented in a network model by, for example, nucleotide sequence, nucleic acid structure, name, symbol, with reference to its encoded gene product, activity or combination thereof. The term is intended to refer to input and output representations, such as text and visual graphics, as well as to programming code or electronic representations within a computer processor. Therefore, a "network gene component" as used herein, refers to a gene component which is part of a network model of the invention.

As used herein, the term "reaction component" is intended to mean a data element, data set or electronic representation of a component of a network, or functional fragment thereof. A network reaction component can be, for example, a gene product, a macromolecule or a molecule. Specific examples of network reaction components include enzymes, substrates, products, cofactors, DNA, RNA, polypeptide, lipid, carbohydrate, amino acids, nucleotides, nucleotide triphosphates, fatty acids, sugars, steroids, metabolites, catabolites, ions, metals, and the like. Such gene products participate or function in a wide variety of chemical or biochemical reactions well known to those skilled in the art, including for example, chemical reactions, binding reactions and signal transduction reactions. A reaction component can be represented in a network model by, for example, primary structure such as amino acid or other monomer sequence of a polymer, secondary structure, tertiary structure, name, symbol, with reference to its encoding gene, reactants, activity or combination thereof. The term is intended to refer to input and output representations, such as text and visual graphics, as well as to code or electronic representations within a computer processor. Therefore, a "network reaction component" as used herein, refers to a reaction component which is part of a network model of the invention.

As used herein, the term "network set" when used in reference to network gene components is intended to mean a group of network gene components encoding gene products that complete a concerted function of a network. Therefore, a network set is at least a subset of components that constitute a network model of the invention. A network set also can contain all components constituting a network model of the invention. So long as a set of components can complete a concerted function of a network, a network set can include, for example, biochemical networks, biochemical pathways and other biochemical systems well known in to those skilled in the art. A network set is "annotated" when it is derived from a gene sequence record that specifies a function or attribute of the recorded gene or a gene product encoded therefrom. Because gene records will have at least one function or attribute associated with them, essentially all gene sequences that have been recorded in a tangible medium or archived are included within the meaning of the term annotated. A function can include, for example, an activity of an encoded gene product such as the conversion of substrate to product or the transition from an inactive state to an active state in the presence of a stimulus. An attribute can be, for example, a nucleotide sequence, a name, a nucleotide or amino acid composition, a molecular weight, a size or a structure. Specific examples of annotated network sets include a genome as well as those biochemical networks and biochemical pathways exemplified previously with reference to networks of the invention. Sources of annotated network sets include, for example, Genbank; Unigene; Subtilist (*Bacillus subtilis*); YPD (*Saccharomyces cerevisiae*); Wormbase (*Caenorhabditis elegans*); ensembl (Human, mouse); PKR (kinases); GPCRDB (G-proteins); EcoCyc, KEGG, WIT, BRENDA (metabolism); Regulon DB, Transfac (regulation); and AFCS, TRANSPATH (signal transduction). These and other databases from which annotated network sets can be obtained are well known in the art as described, for example, in Baxevanis, *Nucleic Acids Res.* 30:1-12 (2002).

As used herein, the term "data structure" is intended to mean an organization of information, such as a physical or logical relationship among data elements, designed to support specific data manipulation functions, such as an algorithm. The term can include, for example, a list or other collection type of data elements that can be added, subtracted, combined or otherwise manipulated. Exemplarily, types of data structures include a list, linked-list, doubly linked-list, table, matrix, queue, stack, heap, dictionary and tree. Such organizational structures can include, for example, data elements representing all categories and subcategories of network components. The term also can include organizational structures of information that relate or correlate, for example, data elements from a plurality of data structures or other forms of data management structures. A specific example of information organized by a data structure of the invention is the association of a plurality of reactions with corresponding reactants and stoichiometry for a network model. Other information that can be organized by a data structure of the invention includes, for example, a representation or relationship of a substrate or product of a chemical reaction, a chemical reaction relating one or more substrates to one or more products, a constraint placed on a reaction, or a stoichiometric coefficient.

As used herein, the term "data set" is intended to mean a collection of data elements. A specific example of a data set is a file. Hierarchical forms and organizations of data sets are also included within the meaning of the term. Data element refers to a unit of data or a computational representations thereof. Generally, data elements and data sets are processed or interpreted to take on meaning. Data representations can include, for example, numbers, characters, images, or other method of recording well known in the art, in a form that can be input into a computer, stored and processed there, or transmitted on some digital channel. Therefore, data elements can be represented, for example, in machine language, assembly language or user language.

As used herein, the term "connectivity" is intended to mean the pattern, interactions and routes of linkage between network components. Such linkages serve to place network components in a physical or functional relationship that specifies a unity of common plan or purpose of such components. Therefore, the term connectivity refers to the aggregation and assemblage of network components joined through physical or functional interaction or interdependence. For example, a chemical reaction that converts compound A to compound B links these compounds by physical interconversion function within a network model. Similarly, where an enzyme uses compound B as a substrate to produce product P, the enzyme and its chemical reaction is functionally linked by interdependence to the above chemical reaction that produces compound B. A specific example of a complex system of connectivity constitutes some or substantially all of the biochemical reactions, interactions and interdependencies of a bioparticle.

As used herein, the term "flux" or "reactant flux" is intended to refer to the flow, transfer or conversion of a network component through a reaction or network. A reaction included in the term can be any conversion that consumes a substrate or forms a product including, for example, changes in chemical composition such as those that occur due to an enzymatic process, changes in location such as those that occur due to a transport reaction that moves a reactant from one cellular compartment to another or a binding reaction. The term includes directionality and can be represented by a variety of means and formats known to those skilled in the art. For example, conversion of substrate to product can be represented as a positive flux of product, corresponding to its formation; or as a negative flux of substrate, corresponding to its disappearance. Positive fluxes also can be characterized to have a forward direction whereas negative fluxes can be characterized as a backward direction. Fluxes also can be represented by, for example, a reaction showing directionality. The term "flux" when used in reference to a pathway or flux pathway is intended to include combinations and permutations of individual fluxes, such as the flow or transfer of network components through a series multiple reactions. Exemplarily combinations and permutations of individual fluxes include a flow, transfer or conversion of network components in or through a biochemical pathway or a biochemical network. Descriptions or representations of a flux or a flux pathway can be either qualitative or quantitative.

As used herein, the term "aggregate reactant flux" or "aggregate reactant demand flux" is intended to mean the combined flow, transfer or conversion of network components through reactions of two or more reaction pathways into a single category for model representation or analysis. Combination of reaction pathways can occur, for example, at the terminal output of a reaction pathway or at any point along the pathway or transfer of reactants or products. Therefore, an aggregate flux can be a portion or subset of a reaction pathway. Aggregate fluxes can be used to define a variety of external inputs and outputs to a system as well as to define internal inputs and outputs that are secondary to the primary network of a particular model. Therefore, the term also is intended to include both internal system fluxes and external fluxes. For example, an internal aggregate flux can be a representation of all amino acid biosynthesis as a single reaction flux. An external aggregate flux can be, for example, a representation of the import into the system of all carbon sources used or by-products generated in an in silico network model of the invention. Aggregate fluxes also can be implemented in a network model to define the activity of one or more biochemical demands.

As used herein, the term "biochemical demand" is intended to mean a flux, a flux pathway or an aggregate flux that represents a biochemical requirement. Such requirements can include, for example, network components used for growth or other cellular or physiological processes, metabolism, catabolism, energy production, redox equivalent production, biomass production, development, or consumption of carbon nitrogen, sulfur, phosphate, hydrogen or oxygen. Examples of a particular network components used for such requirements include, for example, the production of biomass precursors, production of a protein, production of an amino acid, production of a purine, production of a pyrimidine, production of a lipid, production of a fatty acid, production of a cofactor, production of a cell wall component or transport of a metabolite. Other biochemical demands and their corresponding network components well known to those skilled in the art also included within the meaning of the term.

As used herein, the term "macro requirement deficiency" is intended to mean the absence of flux or inappropriate flux directionality from one component of a network model to another interrelated network component. Absence of flux includes, for example, an undesirable buildup of a reaction product, lack of a substrate required for a reaction to occur, or a gap in a reaction network wherein a metabolite can be produced but not consumed or where a metabolite can be consumed but not produced. Absence or inappropriate flux also can include, for example, singleton network components that exist in the system model in isolation and multiple, adjacent network components that have irreversible thermodynamic assignments. A specific example of a singleton network component is a reaction within a biochemical pathway existing in a network model without a flux of reactants to and from the reaction. A specific example of multiple, adjacent irreversible components is where two or more connected reactions have irreversible kinetic parameters.

As used herein, the term "elemental balancing" refers to conservation of chemical elements during chemical transformation of one network component into another. The term therefore includes the stoichiometry of a chemical reaction as well as accounting for other chemical inputs and outputs of a chemical reaction. A specific example of elemental balancing includes ensuring that the total number of oxygen atoms, for example, in all reactants used in a transformation equals the number of oxygen atoms in all the reactants formed by the transformation. Similarly, for all other atoms constituting the substrates or input reactants in a transformation, the number of each type of atom consumed will equal the number of the same type of atom formed if that reaction is elementally balanced. In the case of multiple transformations, such as those constituting a reaction network, the multiple transformations will be elementally balanced when, for each atom, the net number of the same type of atom consumed by the multiple transformations, taken as a whole, is equal to the net number of the same type of atom formed by the multiple transformations, taken as a whole. Elemental balancing includes, for example, all elements within the Periodic Table such as carbon, hydrogen, phosphorus, nitrogen, zinc, magnesium and the like. The term "charge balancing" refers to the similar process of accounting for equivalent input and output of all electrical charges on a reactant participating in one or more chemical reactions.

The invention provides a computer implemented process for constructing a scalable output network model of a bioparticle. The process includes the computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components, and (c) transforming the data set into a mathematical description of reactant fluxes defining the network model of connectivity and flow, wherein the mathematical description defines a scalable output network model of a bioparticle.

A computer implemented process of the invention can be carried out on a computer system that provides a means to construct, access, modify or utilize a network model of the invention as well as the information associated with the network model. A computer system can have any of a variety of known architectures including, for example, single tier or multi-tier architectures. An exemplary architecture for a computer system of the invention is the multi-tier or multi-server application shown in FIG. 1 and consisting of an application server 1 that communicates with a client work station 2, computational server 3, and database server 4. Two-way communication can occur between the servers such that the application server 1 receives input from the other servers and sends output information to the other servers. A user can interact with the system through a client workstation 2 which communicates with the application server, for example, by sending a query or command and by receiving the results of a computer implemented process of the invention.

An application server 1 can extract data from the database server 4 or can launch simulations calculated on the computational server 3, for example, in response to a query or command received from the client workstation. Examples of databases that can be accessed by the database server include a compound database, gene database, reaction database, bioparticle database or a reference database, each of which is described in further detail below. Simulations that can be accessed by a computational server 3 can include, for example, a single optimization analysis, deletion analysis, robustness analysis, phase plane analysis or time-course analysis each of which is set forth in further detail below.

A multi-server architecture allows for the ability to manage information by storing the information on separate servers that can reside in the same location or can be globally distributed as in an application service provider (ASP) distribution model. The architecture can include any of a number of compatible network systems known in the art such as a local area network (LAN) or a wide area network (WAN). Client-server environments, database servers and networks that can be used in the invention are well known in the art. For example, the database server can run on an operating system such as UNIX, where the operating system is running a relational database management system, a World Wide Web application or a World Wide Web server.

Instructions or software code to implement a process of the invention can be written in any known computer language including, for example, an object oriented language such as Java or C++, a visual programming language such as Visual Basic or Visual C++, or other languages such as C, FORTRAN or COBOL and compiled using any well-known compatible compiler.

The software of the invention can be run from instructions stored or active in a memory, such as random access memory, on a host computer system. Similarly, information utilized in model construction and use, such as network components and network models, is stored in a memory on a host computer system such as a read only memory. A memory or computer readable medium can be a hard disk, floppy disc, compact disc, magneto-optical disc, Random Access Memory, Read Only Memory or Flash Memory. A computer system that contains the memory or computer readable medium used in the invention can be a single computer or multiple computers distributed in a network.

A database or data structure of the invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, "Learning XML" O'Reilly and Associates, Sebastopol, Calif. (2001).

The system architecture of FIG. 1 is exemplary. Those skilled in the art will recognize that a process of the invention can be implemented on any of a variety of compatible architectures. For example, the functions carried out by the servers can be consolidated into fewer servers or, alternatively, different functions or modules, such as those set forth below, can be tiered into a greater number of servers if desired. Although a single client desktop 2 is shown in FIG. 1, it will be understood that the system can be readily modified to a multi-user distributed application to support collaborative network model construction or simulation, for example, by including multiple client desk tops that access an application server 1.

A computer implemented process of the invention performs specified manipulations of data or information in response to a command or set of commands given by a user. A computer implemented process of the invention can be carried out by a computer system that provides an interface for a user to interact with the process by means of at least one use-case. A user is someone or something that interacts with a computer system from outside of the system. A use-case is a sequence of actions that a system performs, usually in response to a user command or input, that yields an observable output or result that is of value to a particular user. Accordingly, a computer system of the invention can include any of the hardware components and compatible software set forth above such that the system contains executable instructions to carry out the computer implemented processes and use-cases set forth below.

A use-case can be used to access or utilize a browser. A browser is understood to be a program which gives some means of viewing the contents of a data element in one or more database and of navigating from one data element to another. A data element can contain information about a compound, reaction, or organism and can be viewed, for example, by hypertext links accessed by the browser.

Figure 2:
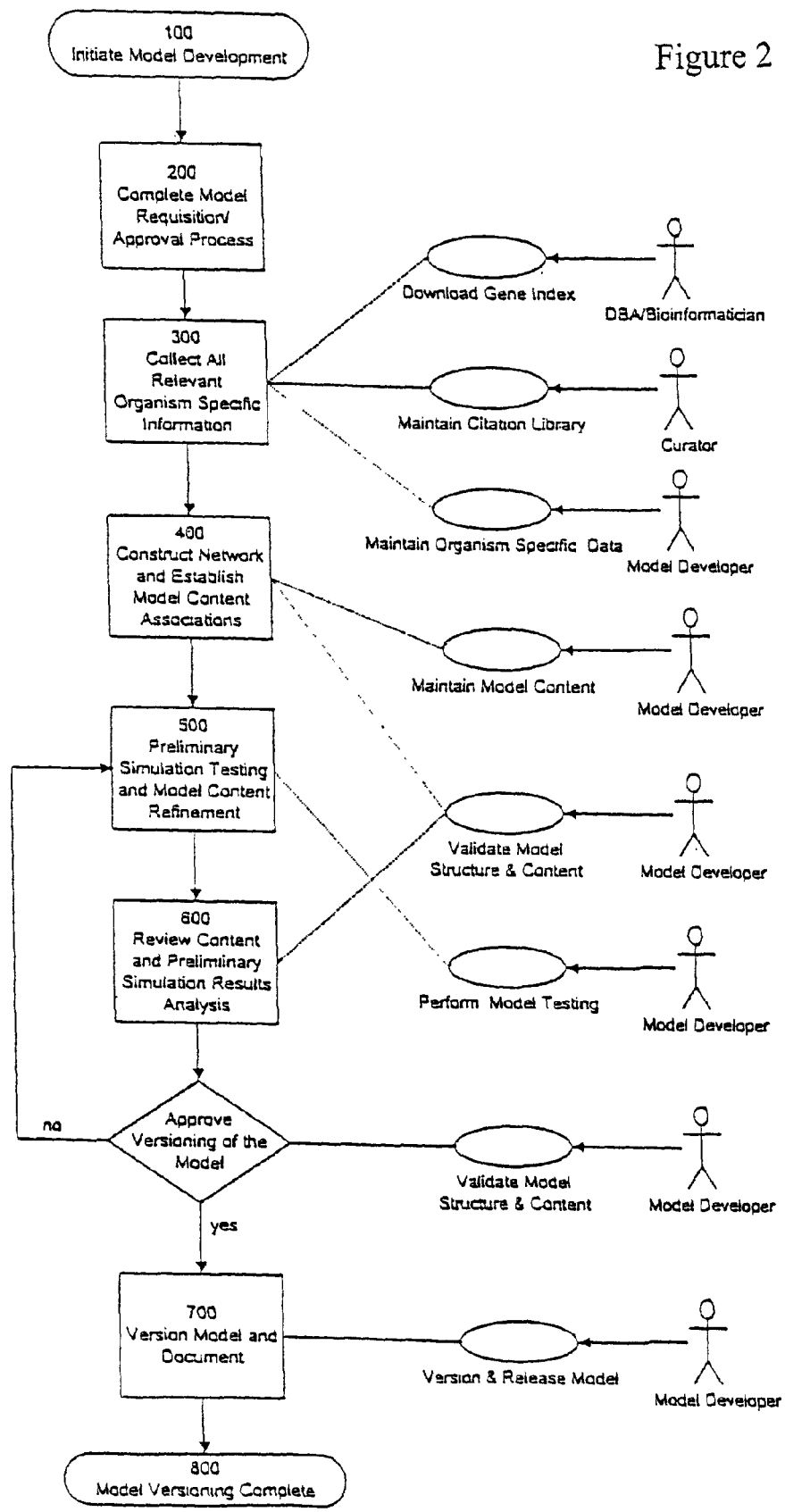
FIG. 2 shows an overview of an exemplary model construction process.

An overview of an exemplary model construction process is provided in FIG. 2. Model construction is initiated 100 by selecting a bioparticle such as an organism, cell or virus or a biological system for which an in silico model is to be constructed. Although model construction will be described below with reference to a bioparticle for purposes of clarity, it will be understood that these steps can be carried out for a biological system within a bioparticle or encompassing more than one bioparticle. A bioparticle can be selected based on any of a variety of factors including, for example, the identification that it is a pathogen and the desire to create an in silico model for determination of effective therapeutic approaches to preventing pathogenecity, the identification that it is useful in an industrial process and the desire to create an in silico model for determination of optimal growth or production properties, or the identification that it is involved in a disease and the desire to create an in silico model for identification of therapeutic targets for treatment of the disease. Any virus, prokaryote, bacteria, archaea or eukaryote for which sequence and or biochemical information is available can be modeled according to the invention. Specific examples of bioparticles that can be simulated by the models and methods of the invention include *Arabidopsis thaliana, Bacillus subtilis, Bos taurus, caenorhabditis elegans, Chlamydomonas reihardtii, Danio rerio, Dictyostelium discoideum, Drosophila melanogaster, Escherichia coli*, hepatitis C virus, *Haemophilus influenzae, Helicobacter pylori, Homo sapiens, Mus musculus, Mycoplasma pneumoniae, Oryza sativa, Plasmodium falciparum, Pnemocystis carinii, Rattus norvegicus, Saccharomyces cerevisiae, Schizosaccharomyces pombe, Takifugu rubripes, Xenopus laevis* or *Zea mays*, and the like.

The construction process can include a step 200 of model requisition. At this step, preliminary evaluation can be made to determine whether to proceed with creating a new model, or to use an existing model, if present, that can be modified. At this step or any time prior to or during the process, individuals can be designated to have access to the model or the databases associated with the model can be selected.

Access can be based on a particular set of rights provided to a user or set of users. For example, rights can include or exclude the ability to view all or part of the information stored in a database, the ability to edit all or part of the information stored in a database, the ability to copy all or part of the information stored in a database, the ability to delete all or part of the information stored in a database, the ability to use all or part of the use-cases included in a computer system, or a combination of these abilities. Limited access, for example, with respect to the right to edit stored information, can provide quality assurance and quality control of a database and the information stored therein. Security and limited access rights can be achieved using known computer security algorithms and hardware such as those available from the SANS (System administration, networking and security) Institute (available on the world wide web at sans.org) or Pentasafe (Houston Tex., available on the world wide web at pentasafe.com). One or more users can be allowed access at a status of curator thereby having full rights necessary to access and maintain algorithms, models or databases.

As shown in FIG. 2, the model construction process can include a step 300 of collecting relevant organism specific information. At this step, a user such as a model developer can create a file structure for the bioparticle under which information relevant to the bioparticle is indexed and stored. Information that can be stored at this step includes, for example, a general description of the bioparticle, an appropriate taxonomy identification for the bioparticle that allows cross reference to information in databases or scientific publications or links to the NCBI Taxonomy Database (available on the world wide web at ncbi.nlm.nih.gov/Taxonomy/taxonomyhome.html/).

At this step, a list of genes that encode gene products that perform reactions carried out by one or more bioparticles of interest, for example, can be created. Many of these reactions occur due to the activity of a biomolecule catalyst or transporter, which are created through transcription and translation of the open reading frames (ORF) or genes found within the genome of a bioparticle. For purposes of brevity, reactions that occur due to the activity of a gene product and for which a cognate ORF is associated are referred to as gene-encoded reactions. Other reactions occur either spontaneously, through non-enzymatic processes or through proteins for which an ORF has not been associated are referred to as non gene-encoded reactions. Management of the data, for example, using a universal data management module can be achieved as described in further detail below.

Every reaction whether or not it is gene-encoded contains one or many reactants, which are the chemical species or compounds involved in the reaction. These reactants can be designated as either substrates or products each with a discrete stoichiometric coefficient assigned to them to describe the chemical conversion taking place in the reaction. The reactants are further specified according to the cellular compartments in which they are present. For example, in a reaction database, a distinction is made between glucose in the extracellular compartment versus glucose in the cytosol. Additionally, reactants in the reaction database can be specified as primary or secondary metabolites to assist in visual representations of large networks of metabolic reactions.

Each reaction is also described by the direction in which it can proceed with the choices being either reversible or irreversible. If a reaction is reversible then it is possible for not only the substrates to be converted into products, but also for the products to be converted into the substrates. Whereas an irreversible reaction is constrained to proceed only in the direction that converts substrates into products.

At step 300 data elements specifying information regarding gene or genomic sequences, or attributes thereof, for a bioparticle can be obtained from an available source by, for example, downloading from a database into a gene index. The information included in this index can be downloaded from a public or private database or from an internal bioinformatics support service. Examples of databases from which gene or genome information can be downloaded include the databases described above and in Baxevanis, supra, 2002. Sequences and annotations for a bioparticle genome or for genome fragments such as genes can be imported and stored in a gene database. The gene index includes structural information such as nucleotide sequences and genome annotation. Genome annotation includes identification of the location of ORFs and identification of homologies to other known genes. This information can be used to determine the function of the associated gene product(s), which can then be linked to the appropriate reactions that are catalyzed by the gene product(s).

Although it is possible to access sequence data from outside databases during model construction and use, a gene index provides the advantage of direct access to data that may be dispersed in multiple non-associated databases and the advantage of uniform storage or handling of information for efficient cross-referencing and access. The system can include an algorithm and software code for importing genome sequences with or without supporting annotations into a gene index. Importation can be manually activated by a model developer or other user who identifies an updated genome dataset and has rights to edit a genome database or gene index. Alternatively, an algorithm and its implementing code can be included that automatically updates the information in a gene index by downloading information from an external database at a particular time interval or in response to a signal from the external database or its administrator that the data has been updated or modified.

Also at step 300 other relevant information such as that available from the scientific literature regarding the genetics, biochemistry, cell biology and physiology of a bioparticle of interest can be gathered. These sources of information can be indexed in a citation library. The information is gathered in preparation for the process of constructing a network model which is described in detail below. The citation library can be integrated into a computer system that is used to make and use a network model such that the information in the citation library can be accessed from cross-references or hypertext links to network model components such as genes, biomolecules, reactions and compounds.

Other network reaction components can also be stored in one or more data bases and accessed in a computer implemented process of the invention. For example, a compound database can be used to store information relevant to biological compounds and reactants including substrates and products of reactions can be identified from the compound data base. A database accessed in a process of the invention can be specific to a particular organism strain, organism, species, family, phylum or kingdom. Alternatively a data base can be a universal database that contains genes, reactions, compounds or other information that is not exclusive for any subset of biological organisms. Thus, a universal reaction database or universal compound database is provided and can be accessed in a process of the invention.

Referring again to FIG. 2, the process can include a step 400 of constructing a data structure of network reaction components. A computer implemented step can be invoked to form a data structure associating network gene components with network reaction components. Such associations establish a data set specifying a network model of connectivity between network reaction components. For example, an ORF of a bioparticle can be selected and its gene sequence or other attributes identified. Such ORF data elements, either individually or together, specify data elements or data sets of a network gene component. The gene component can be associated directly, or used to identify its encoded gene product as a corresponding network reaction component. Obtained or identified network reaction components and their associated attributes, such as the reactants, enzymes or proteins that carry out the reaction, or mRNA encoding the enzyme or protein, similarly constitute data elements or data sets that can be incorporated into a network model by association with gene components. All other associated relationships and attributes of identified gene and reaction components can similarly be incorporated into the network model by similar association. Such associations of gene and reaction components define the connectivity of gene product production and the connectivity and flow of reactions components of a network model of the invention.

As described further below, the process of association can be repeated for inclusion of additional network components until a sufficient number of components have been identified to specify a functional group of interconnected or interrelated network members. Component attributes such as activity, substrates, products, reactants and stoichiometry serve to automatically associate, by natural biochemical relationships, the individual network components into an interconnected functional model. The natural relationships formed can be modified, for example, by a developer or user of a network model of the invention. Therefore, the process of identifying, including and associating network components into a model of the invention serves to define the connectivity and flow of components and activity within the boundaries of the model itself.

Association of data elements or sets of network gene components with corresponding data elements or sets of network reaction components can be performed by any computational method well known to those skilled in the art. For example, the individual data elements that make up the resultant data set can be associated using relational tables. Alternatively, data elements can be associated using, for example, functions such as indexing, pointing, querying and the like. Similarly, combinations of these and other structures or functions can similarly be employed to associate network components included in a model of the invention. Further, the data elements can be partitioned within a database based on related characteristics or attributes or stored randomly. Alternatively, different databases can be used to store categorized or uncategorized data elements. Therefore, associations of network components can be accomplished by any electronic linkage, physical archival form or combinations thereof.

A data structure that is formed by the computer implemented process of the invention can be any physical or logical relationship among reaction components that supports flux balance analysis. Briefly, the data set consisting of associated data elements can be directly employed as a data structure of the invention. For example, the associated data set can be accessed by query and response from, for example, designated servers or specified server functions, and the associated data elements invoked as a single data structure during application of a network model of the invention. Alternatively, such associations can be further manipulated into secondary forms that can be accessed and utilized in the computer implemented methods of the invention. Such secondary forms can be created by, for example, further indexing, partitioning or the creation of subfiles and substructures of the data elements. For example, some or all of the associated data elements describing gene and reaction components can be consolidated into a single data set. Where less than all of the data elements describing network components of a model of the invention are consolidated, it can be beneficial to maintain the associations and relationships to the original data elements and data sets to provide a continuous link to all characteristics and attributes of any particular network component represented by a data element. Maintaining such links provides an advantage of invoking computational processes on data elements relevant to network model performance while allowing manipulation of input, optimization and output of all data elements of any network component or any specified subset thereof.

Figure 3:
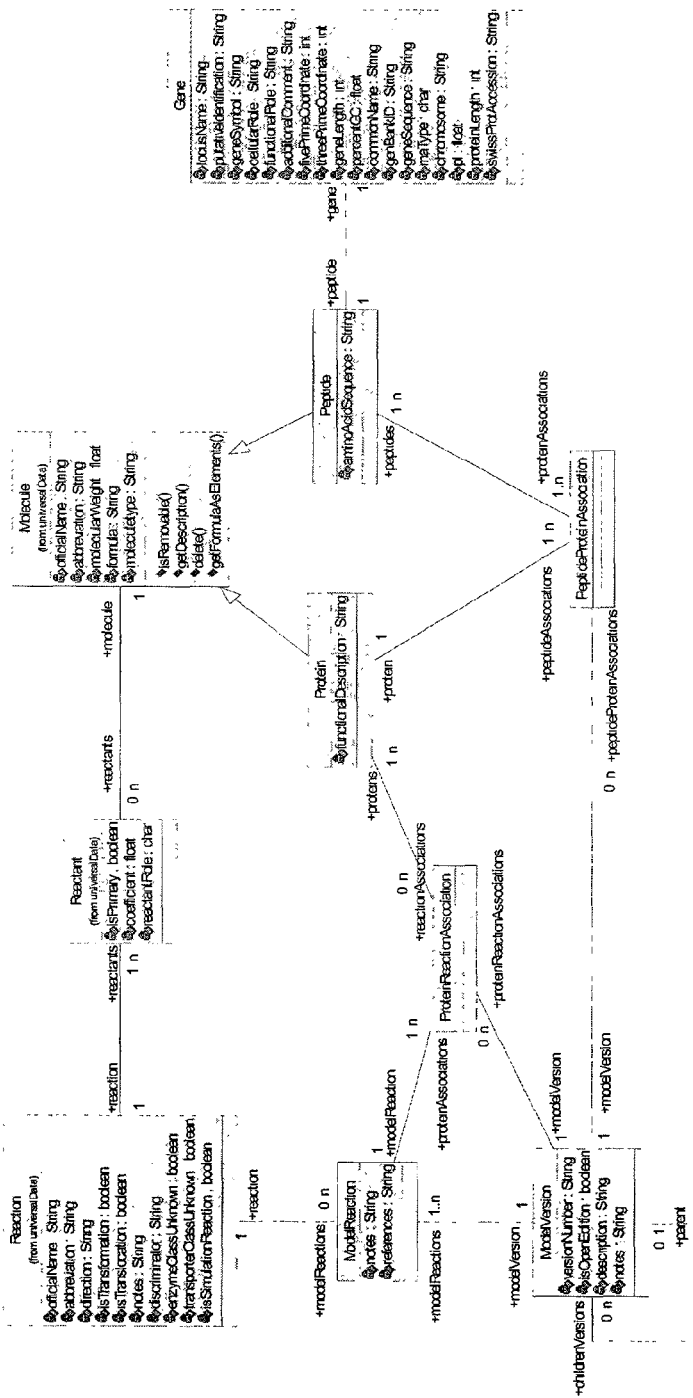
FIG. 3 shows an associated object model of a network model specifying the participating classes of network component data elements and associations in a biochemical network of a bioparticle.
Figure 4:
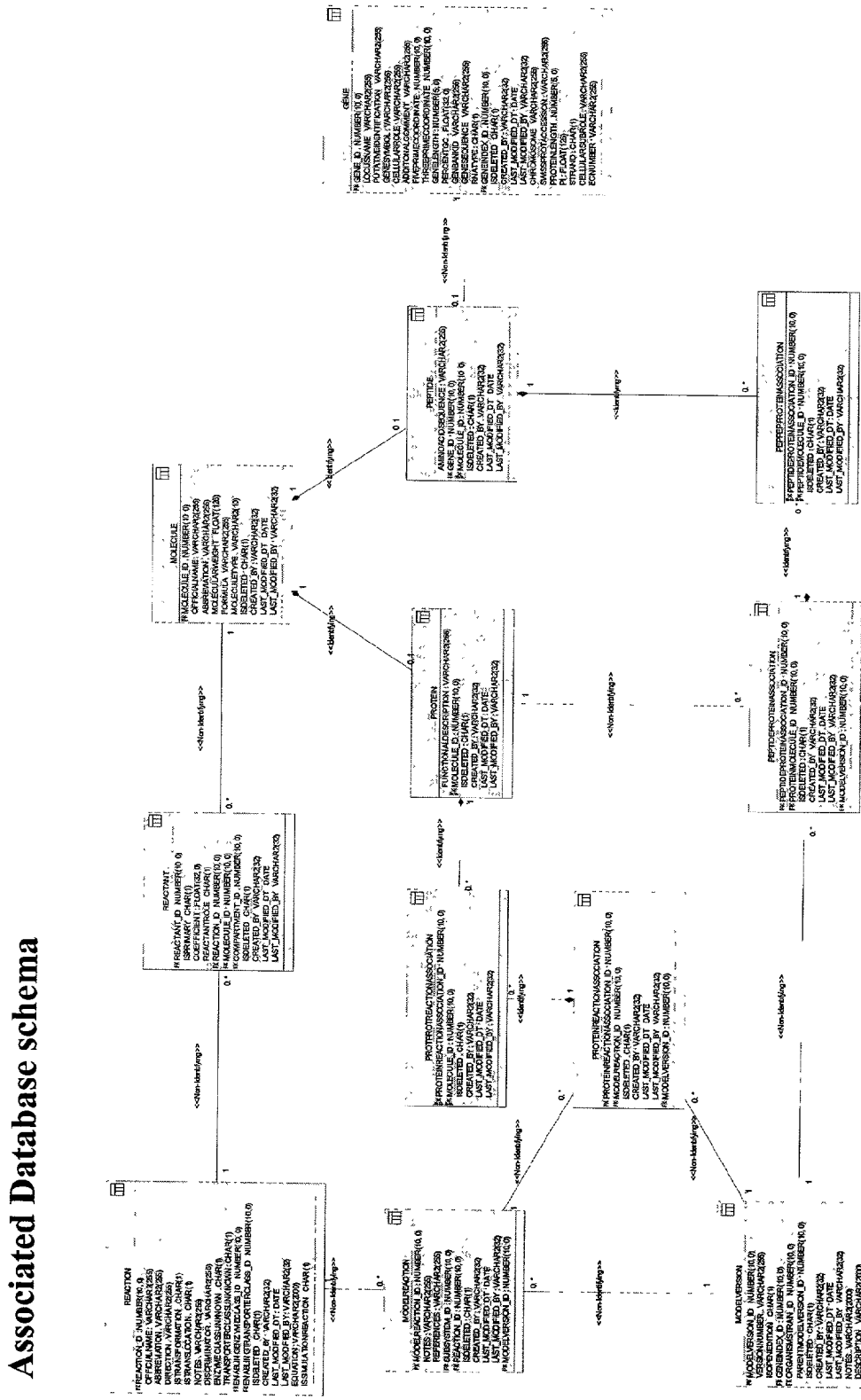
FIG. 4 shows an associated database schema of a network model specifying the participating tables of network component data elements and associations in a biochemical network of a bioparticle.

Specific examples of associations that can be constructed of network gene components and network reaction components by the computer implemented processes of the invention are described further below and in Example I. FIGS. 3 and 4 described therein set forth exemplary data elements specifying network components of a network model of the invention and their associations in both object model and database schema forms. FIG. 3 shows an associated object model specifying the participating classes of network component data elements and associations in a network model of a bioparticle. FIG. 4 shows an associated database schema specifying the participating tables of network component data elements and associations in a biochemical network of a bioparticle.

As shown in FIGS. 3 and 4, the network components can be organized into tables such as a table for reaction, reactant, molecule, protein, peptide, model reaction, model version or gene. Within each table is a collection of records for attributes of the network component. For each record the fields are populated by the information added during network model construction as described below.

A record can contain an attribute that is represented in any appropriate format known in the art including, for example, a string, integer, float, character or boolean expression. String records are used for records that will have fields representing descriptions such as those for official name, abbreviation, direction, notes and discriminator in the table for the reaction network component. Boolean records are used to represent attributes for which one of two values is descriptive including, for example, whether a reaction is a transformation, translocation, unknown enzyme class, unknown transporter class or simulation reaction in the table for the reaction network component. Integer records can be used to denote numerical values such as the 5' coordinate, 3' coordinate, gene length and protein length occurring in the gene table. Examples of records that are represented as a float are molecular weight in the molecule table and coefficient including, for example, kinetic constants or binding constants in the reactant table.

Exemplary associations between network components are indicated in FIG. 3 and FIG. 4. The associations can be utilized during various stages of model construction. For example, for the construction of a gene-protein association the tables that participate include the Peptide table, PeptideProteinAssociation table, PepPepProteinAssociation table and Protein table as shown in FIG. 4. The classes that participate in creation of a gene-protein association include Peptide, PeptideProteinAssociation and Protein. As another example of constructing an association using the tables and classes shown in FIGS. 3 and 4, a protein-reaction association is constructed using the Protein class, ProteinReactionAssociation class and ModelReaction class and using a Protein table, ProteinReactionAssociation table, ProtProtReactionAssociation table and ModelReaction table.

Although the invention has been exemplified above with respect to a relational database, one of skill in the art will appreciate that the concepts presented herein may be applied outside of the relational database system of operation. In particular, the concepts are applicable in any database environment including for example an object-oriented database, hierarchical database or network database.

A data set specifying network component associations can be transformed into a mathematical description of the network system being constructed. For example, in the specific case of modeling biochemical networks of a bioparticle, biochemical reactions of the network model can be transformed into a set of linear algebraic equations and inequalities. An inequality sets a constraint on a reaction that specifies an upper or lower boundary for the reaction. A boundary can specify a minimum or maximum flow of mass, electrons or energy through a reaction or can specify directionality of a reaction. A boundary can be a constant value such as zero, infinity, or a numerical value such as an integer. Alternatively, a boundary can be a variable boundary value.

The set of equations and inequalities constitutes a mathematical description of the referenced network model. A data structure of mathematical equations can be further represented as a stoichiometric matrix S, with S being an m×n matrix where m corresponds to the number of reactants or metabolites and n corresponds to the number of reactions taking place in the network. Each column in the matrix corresponds to a particular reaction n, each row corresponds to a particular reactant m, and each $S_{mn}$ element corresponds to the stoichiometric coefficient of the reactant m in the reaction denoted n.

A stoichiometric matrix provides a convenient format for representing and analyzing a network model because it can be readily manipulated and used to compute network properties, for example, by using linear programming or general convex analysis. A network model data structure can take on a variety of formats well known to those skilled in the art so long as it is capable of relating components and reactions in the manner exemplified above for a stoichiometric matrix and in a manner that can be manipulated to determine an activity of one or more reactions using methods such as those exemplified below. Other examples of network model data structures that are useful in the invention include a connected graph, list of chemical reactions or a table of reaction equations. Such a table of chemical reactions can further be annotated with kinetic information about the chemical reactions and transformations. Kinetic information can be accessed and used to apply differential equations to a network model of the invention or the reaction components therein to integrate over time.

Figure 5:
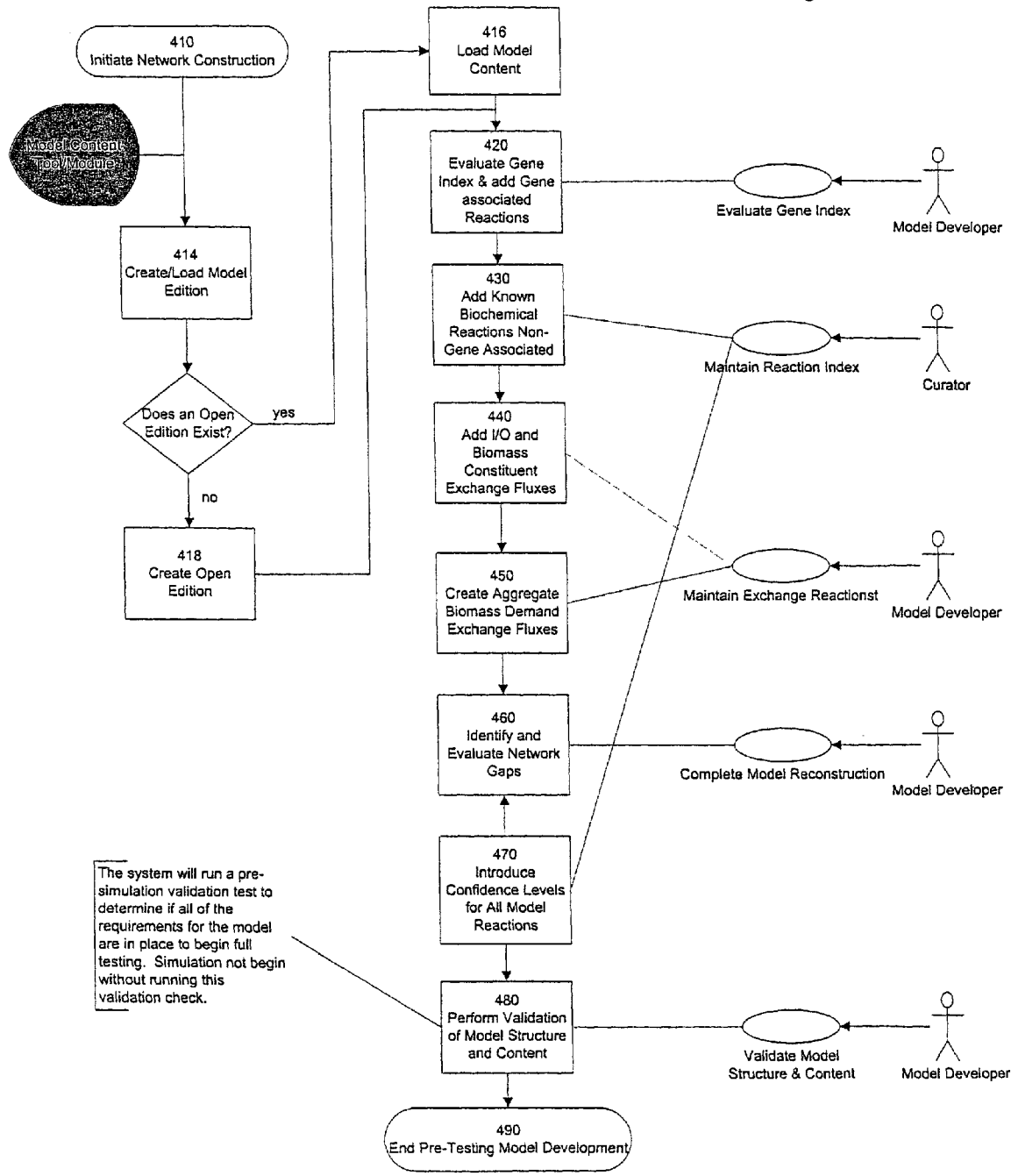
FIG. 5 shows an exemplary process of constructing a data structure of network reaction components.

An exemplary process for implementing step 400 is shown in FIG. 5. The process is initiated at step 410 and proceeds to step 414 where a model is created or loaded. If an open edition of a desired network model is not present or accessible in the computer system, the process can proceed to step 418 in which an open edition is created and can then proceed to step 420. An open edition of a network model is one that is being generated or under construction. After sufficient improvement to the model content and preliminary testing the model can be saved as a versioned model to capture the current content of the model as a basis for future simulation studies.

A versioned model is saved such that a copy of the versioned model is archived and the content of the archived model is secured or not substantively modified. If at step 414 an open edition is present and accessible, then the network model can be loaded into, for example, a computer processor or memory at step 416 and the process can proceed to step 420. It will be understood that a versioned model can also be loaded at step 416, for example, in order to create an updated or modified version of the model so long as at least one copy of the versioned model is archived and the model once opened at step 416 is stored as an open model until being saved as a new version.

Figure 6:
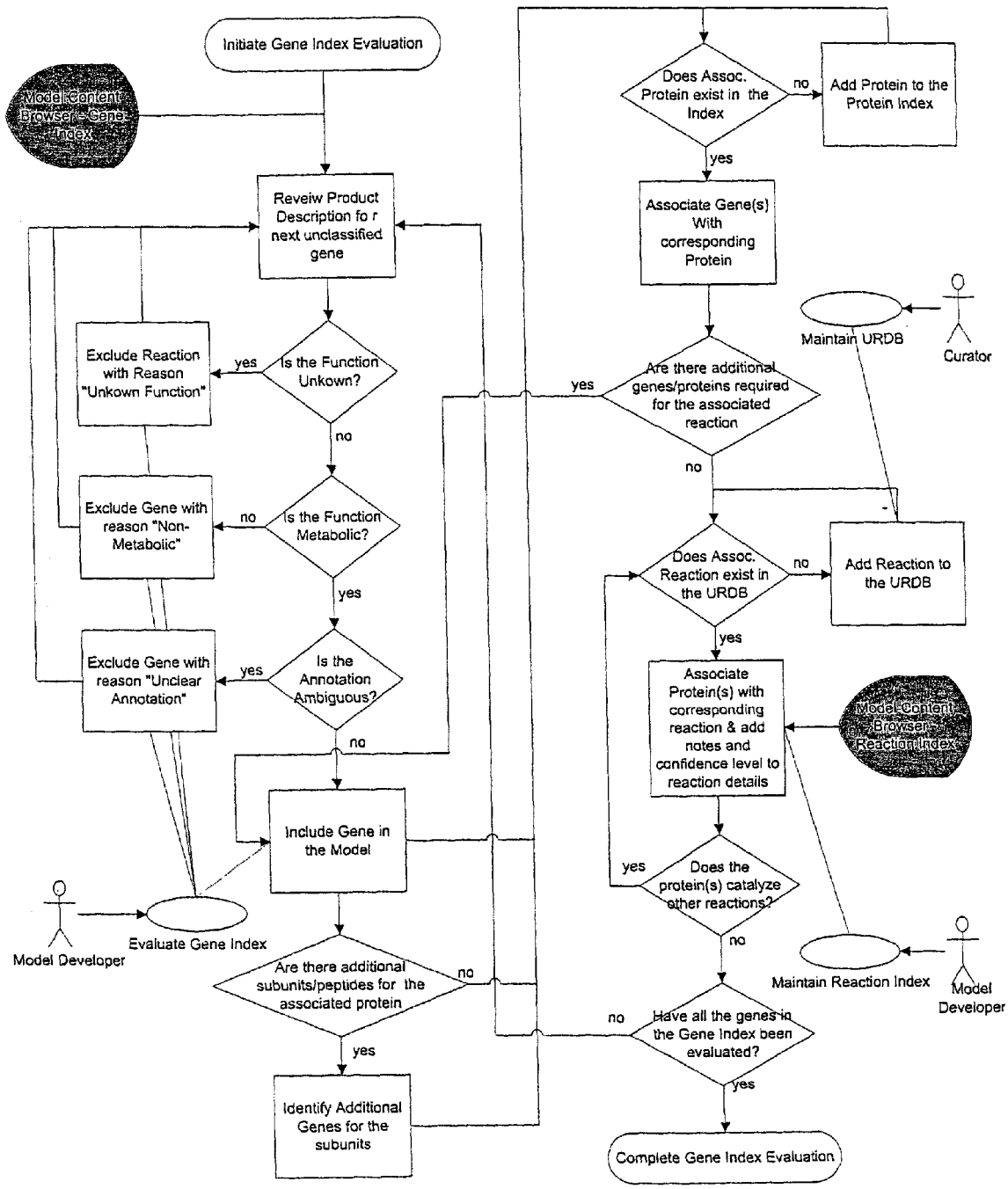
FIG. 6 shows an exemplary process of evaluating a gene index and creating reaction associations.

At step 420 gene associated reaction components are added to a data structure of network reaction components. An exemplary process for implementing step 420 is shown in FIG. 6. As the data structure is being built, appropriate associations for each reaction to one or more related proteins and one or more related genes is assigned. These associations capture the relationships between the genes and proteins as well as between proteins and reactions. In some cases one gene codes for one protein which then catalyzes one reaction. However, often there are multiple genes which are required to create a protein and often there are multiple reactions that can be carried out by one protein or multiple proteins that can carry out the same reaction. These associations can be captured by boolean logic operators such as "AND" or "OR". These associations can also be captured in an association diagram as set forth below in the context of a model construction module.

The representation of these associations in a network model of the invention provides the advantage of readily visualizing and determining the implications of adding or eliminating model content at the genetic, protein or reaction level in the context of making a network model or running a simulation with a network model. In general, each of the genes in the gene index is evaluated for inclusion in or exclusion from a network model. If a gene is excluded, a reason can be provided in the annotations associated with the network model.

The associations of network gene and reaction components can be implemented in a variety of different procedures. For example, the associations can be made in a sequential manner, or alternatively, in bulk, parallel or series. Additionally, a number of intermediate steps or groupings in the associations also can be performed to facilitate or organize the resultant data structure. A specific example of the process of step 420 is where the implementing instructions invoke the selection or identification of a network reaction component based on an identified gene component.

Identified gene components can be obtained, for example, from accessing a source of open reading frames (ORF). The source can be derived from a variety of different resources and will depend on the network model intended to be constructed. For example, where a network model representing a biochemical pathway or a bioparticle function is to be constructed, a source of ORF data representing the activities of the pathway or the bioparticle function can be used. Specific examples include a gene database for the glycolysis pathway or a gene database for cellular metabolism. Similarly, where a network model representing the functions and activities of a bioparticle or subsystems thereof, a genomic database representing a substantially complete catalog of the bioparticle encoded genes can be used.

One advantage of using an annotated network set of ORFs in constructing a network model of the invention is that it serves as an internal check on both the incorporation of network reaction components and on the completeness of the resultant model. For example, proceeding through a closed or finite list of gene components to be incorporated into a network model serves to internally constrain the number of possible associations as well as identify aberrantly included or aberrantly associated network components. Therefore, construction of a network model from an annotated network set of ORFs provides both an upper and a lower limit for the components to be associated in the resulting data structure. Accordingly, model construction can proceed in a finite space of components and associations.

Such a closed list of network gene components can be, for example, small such as would be for a pathway or bioparticle function. A closed list also can be, for example, large such as a bioparticle or organism genome. It is not necessary that an annotated network set be specified in a single list or file, or stored as a unique data entity. Instead, an annotated network set can be, for example, a subset of a larger database. Therefore, all that is required is the delineation of those ORFs included in an annotated network set from those excluded from the set.

Regardless of the actual size of an annotated network set of ORFs, such a gene component set provides a genetic catalog or checklist for which the computer implemented process can proceed through and ensure that the listed gene components have been accounted for by, for example, either inclusion or exclusion from the network model being constructed. Additionally, the genetic catalog also can be used to invoke additional queries that call or proceed through routines relating to the identification and association of interactive and interrelated gene and reaction components. Invoking such routines or other analyses provides for a more complete or thorough representation of the authentic system is reproduced in the constructed network model.

For example, starting with a single ORF, the process of the invention can generate queries for identifying the corresponding encoded gene product and attributes as well as any associated subunit components, their cognate ORFs and additional reaction constituents such as substrates, products and cofactors. From that initial ORF and its identified gene products, cognate gene and gene product components, additional queries can be further invoked that expand on these associations by identifying network components related to the component being analyzed. Such expanded relationships can be, for example, the search and identification of network components upstream or downstream from the analyzed activity or physical interaction or of components and activities that are required to produce or deplete reaction constituents for the analyzed activity.

Higher levels of expansion based on the initially selected ORF and its associated gene product can additionally be invoked depending on the need of the user or until queries and searches are exhausted. The computer implemented process can then proceed, for example, to the next ORF within the annotated network set to invoke the above queries and routines for identification of further reaction components and association into a network model data structure. Repeating this process of selecting an ORF, identifying its corresponding reaction component, querying and identifying interactive and interrelated gene, cognate gene and reaction components as well as reaction constituents until each member within the annotated set is analyzed will yield a comprehensive group of network components that can be included by association into the network model being constructed.

An additional advantage of model construction from an annotated network set of ORFs is that it provides or allows for the creation of data structure associating gene components with reaction components that will capture the inherent complexity of biochemical systems or living bioparticles. More-over, such complexity can be reproduced in a network model with minimal knowledge or empirical determinations of the complete interactions or interrelationships of the system. Capturing and reproducing the natural complexity of biological and biochemical systems allows for a more accurate reproduction of the natural system in the resultant network model.

For example, there can be instances where a particular biochemical function is redundantly encoded in a bioparticle's or organism's genome. Redundancy can therefore result in different gene products exhibiting similar function being represented in the repertoire of gene products. However, inclusion in a model of only a single gene product or activity can produce inaccurate or incomplete predictions because modification or perturbation of that single gene product or activity will not account for the substitutability of similar functions being present in the natural bioparticle or organism. A specific example augmenting the predictability of a network model by capturing the natural complexity of a biochemical system through inclusion of associations between network gene and reaction components is described below in Example I. Thus, entirely different phenotypes can be observed depending on whether component redundancy is accounted for in a model. Other examples benefitting model reproduction and predictability of the authentic system by the inclusion of gene component associations include, for example, characterization of epistatic effects, evaluation of regulation at the gene, protein and reaction levels, comparative evaluation of the activity of isozymes or determination of the completeness with which the subunits of a multimeric protein are present in a network model.

Referring again to FIG. 6, and with reference to the initial process of selecting and associating gene and reaction components within a data structure, the computer implemented process of the invention gathers information related to the selected ORF in an initial screening or triage step. This initial step focuses on identifying and including network components specific for the model desired to be constructed. The information can be gathered by, for example, querying the user, a database or a server and obtaining replies that yield in the alternative a decision to either include or exclude the selected gene component in the data structure. For example, positive answers to whether the gene function is known, it is within the scope of the model being constructed or to nonambiguous annotation or gene attribute information allow for inclusion of the selected gene component into the developing model. In this regard, a gene component can have a known function and clear annotation of attributes but be outside the scope of the model and be excluded such as when a metabolic model is being constructed but the selected ORF encodes a nucleic acid binding protein or vice versa.

Once a network gene component is determined to be included within a model being constructed, the process queries the user or a data source for identification of its encoded gene product. Alternatively, the process can electronically translate the gene component nucleic acid sequence data and include that information directly, or search a gene product data base to obtain the encoded amino acid sequence as well as other attributes. As a maintenance procedure of the system, those gene products not represented in the corresponding database can be deposited in the system at this point or marked for later deposit during routine maintenance procedures. Following identification or generation of the corresponding gene product information, the resulting gene and reaction components are associated into a data structure. Generally, such association can be accomplished by employing relational databases and tables. However, and as described previously, essentially any means known to those skilled in the art can be used to form such associations.

Once a network reaction component is associated with a gene component, the process can further implement the selection of a new ORF from the annotated network set of ORFs and proceed with identification of its encoded gene product and related attributes. The initial selection queries for determining inclusion or exclusion is performed as described above. Further, the selection of subsequent ORFs and their encoded gene products can be performed, for example, sequentially, in parallel or in series with the previous or subsequent ORF selections and processing. The newly identified network reaction components can again be subsequently incorporated into the network model by association with its corresponding gene component. Additionally, the functional and characteristic attributes of the reaction components also can be incorporated into the data structure of the network model being constructed.

As described previously, once a network reaction component is associated with a gene component, the process can proceed further to extract or query data repositories or the user for related gene and reaction components as well as associate attributes of the identified network reaction components. Such related components include identifying and associating, for example, functional activities such as biochemical reactions, binding properties and other functional attributes; reaction constituents such as reactants, products and cofactors; constituent gene products such as subunits and regulators, as well as the various network gene and reaction components for such additionally identified network components. The implementation of these routines also is shown in FIG. 6. Finally, for each identified reaction component, the process of the invention additionally queries whether the gene product catalyzes or participates in other reactions or processes. This step serves to expand the model construction process at each component to higher levels of component search, identification and association.

Therefore, for each ORF included in the model construction as a gene component, the computer implemented process of the invention proceeds through routine 420 one or more times until responses to the decision points are negative or exhausted or until the productivity of the output is outweighed by burden on computer or user resources. The repetition of routine 420 begins at the square box in FIG. 6 denoting inclusion of a gene in the model. Upon termination of routine 420 for a particular included gene component, the process of the invention can continue through the annotated network set of ORFs by selecting another ORF and subjecting it to the preliminary decision points for inclusion into the developing model. Once included as a gene component, routine 420 is again implemented to identify and associate its encoded gene product as a reaction component, cognate gene components, gene product subunits, reaction constituents, additional gene products participating in the identified activity and the like. The complete routine 420 process can be, for example, repeated one or more times until the constituent ORFs of annotated network set, or a functional subset thereof, are processed and analyzed in similar fashion.

Therefore, the invention provides a data structure that can be formed in a process of the invention by the steps of (a) selecting an ORF from the annotated network set encoding a gene product having a network reaction function; (b) forming a data structure including the selected gene product, the data structure associating network gene components and network reaction components including cognate ORFs, encoded gene products, network reactions and reaction constituents, and (c) repeating steps (a) and (b) selecting another ORF from the annotated network set until substantially all of the network gene components of the annotated network set have been surveyed for encoding a gene product having a network reaction function to produce a data structure establishing a data set specifying a network model of connectivity and flow. The process can further include the steps of (a) determining the occurrence of a constituent gene product for the selected encoded gene product; (b) determining the occurrence of an additional gene product participating in the network reaction; (c) determining the occurrence of an alternative network reaction exhibited by a surveyed gene product; and (d) incorporating identified constituent gene products, participating gene products or alternative network reaction into the data structure.

A process of the invention can further include a step of elemental balancing at least one network reaction. Similarly, a process of the invention can include a step of charge balancing at least one network reaction. Such balancing takes into account conservation of mass, elements and charge as they occur in a biological system. Upon entry of a reaction by a user, a routine can be implemented to compare the substrates and products of a reaction to determine if mass is balanced such that the number of each atom type that enters a reaction in the substrates, matches the number that exits the reaction in the products. A similar comparison of the charge on substrates and products can be used to automatically determine if charge is balanced in a reaction that has been entered into the network model. If charge and mass are balanced the process is allowed to proceed to the next step in the construction process. However, if imbalance is found the system can send an appropriate message to the user indicating that the reaction is not balanced. The message can further indicate the nature of the imbalance and suggest reaction constituents to add or remove in order to satisfy mass or charge balance.

By monitoring the balance of charge, elements and mass on the reaction network the system makes resources available to a user that allow the user to interactively construct a network model that reflects the flux of mass and charge in a biochemical reaction network or biological system. Although mass, elements and charge balancing is not necessary for all applications of the network models of the invention, establishing this balance can account for phenotypes or system behaviors that occur in response to the net consumption or production of charge or a particular element. For example, the production of protons can affect cellular processes by altering pH, changing membrane potential, or contributing to processes that are energetically effected by proton influx/efflux such as metabolite transport and ATP levels.

The process of constructing a data structure of network reaction components can include a step 430 of incorporating a network reaction that is not gene-encoded and corresponding reaction constituents into a data structure of network reaction components as shown in FIG. 5. While many of the reactions of a bioparticle are associated with genes, there can also be a number of reactions included in a model for which there are no known genetic associations. A non gene-encoded reaction can be identified, for example, from the biochemical literature or identified during the course of model construction based on the need for a reaction to satisfy a macro requirement deficiency. Knowledge of a gene or biomolecule that is associated with a reaction in a network model of the invention is not required for simulation using the model. However, such information provides advantages for efficient model building and for evaluating the results of a simulation.

At step 430 reactions that occur spontaneously, that are not protein-enabled or that have not been associated with a particular gene product or open reading frame can be added to a data structure of network reaction components. Alternatively, a reaction can be added absent biological evidence indicating the occurrence of the reaction in a system being modeled, for example, based on results of a simulation and the identification of the need to satisfy a macro requirement deficiency by adding the reaction.

One or more non gene-encoded reactions can be added to a network model during the course of model construction. Such a reaction can be associated with other reaction components such as reaction constituents and, where known, a cognate protein. The process can be carried out in the context of the model content browser. The computer implemented process is initiated when a determination is made to add a non gene-encoded reaction to a reaction index. The determination can be made by querying a user and obtaining a reply that yields an alternative decision that the reaction does or does not exist in a reaction database. If the reaction occurs in a reaction database to which the user has been given access, the reaction can be selected by the user and the system will automatically include the reaction in the reaction index. Alternatively, if the reaction does not exist in the reaction database, the user can be queried to enter the reaction and its corresponding reaction constituents into the reaction index.

A reaction that is added to a reaction index can be added to a reaction database. The system can be configured to automatically add the reaction to the reaction database. Alternatively, the reaction can be displayed to a curator who responds to a query regarding whether or not the reaction is to be added to the reaction database. If the curator responds in the affirmative, the computer implemented process can add the reaction to the reaction database. Alternatively, a negative response by the curator will prevent addition of the reaction to the reaction database at that time. The process can proceed to query the user to edit reaction details such as the confidence level or to add a reference citation.

The reactions in a data structure of network reaction components can be assigned to subsystems if desired. The use of subsystems provides advantages for a number of analysis methods such as pathway analysis and can make the management of model content more efficient. The model developer can specify the name of a subsystem and then assign reactions to the subsystem. This assignment allows a user to search for reactions in a particular subsystem which may be useful in performing various types of analyses. Furthermore, assignments of subsystems can be indicated on reaction maps, thereby facilitating evaluation of simulation results.

The reactions included in a data structure of network reaction components can be obtained from a reaction database using use-cases that are, for example, set forth below. Alternatively, reactions can be newly added, for example, by obtaining compounds from a compound database and building a reaction using methods similar to those set forth above for creating a reaction database. Reactions added at this stage of model construction can be subsequently added to a reaction database.

The reactions added in steps 420 and 430 are intra-system reactions. Intra-system reactions are the chemically and electrically balanced interconversions of chemical species and biochemical processes, which serve to replenish or drain the relative amounts of certain metabolites. These intra-system reactions can be classified, for example, as either being transformations or translocations. A transformation is a reaction that contains distinct sets of compounds as substrates and products, while a translocation contains reactants located in different compartments. Thus, a reaction that transports a metabolite from the extracellular environment to the cytosol, without changing its chemical composition is classified as a translocation, while a reaction such as the phosphotransferase system (PTS) which takes extracellular glucose and converts it into cytosolic glucose-6-phosphate is a translocation and a transformation.

Referring again to FIG. 5, the process of constructing a data structure of network reaction components can include a step 440 of incorporating an exchange reaction for an external reaction component and corresponding reaction constituents into a data structure. Exchange reactions are the reactions that will allow compounds to be introduced and removed from the network for the purposes of simulation. Exchange reactions can be created based on empirically observed phenotype or behavior of a biological system.

The metabolic or other biochemical demands placed on a biological system can be readily determined from the dry weight composition of a cell which is available in the published literature or which can be determined experimentally. The uptake rates and maintenance requirements for an organism can be determined by experiments in which the uptake rate is determined by measuring the depletion of the substrate from the growth medium. The measurement of the biomass at each point can also be determined, in order to determine the uptake rate per unit biomass. The maintenance requirements can be determined from a chemostat experiment. For example, the glucose uptake rate can be plotted versus the growth rate, and the y-intercept interpreted as the non-growth associated maintenance requirements. The growth associated maintenance requirements are determined by fitting the model results to the experimentally determined points in the growth rate versus glucose uptake rate plot. A data set of the invention can be modified to enumerate these experimentally determined demands using exchange reactions.

Exchange reactions are those which constitute sources and sinks, allowing the passage of metabolites or other network components into and out of a compartment or across a hypothetical system boundary. These reactions are included in a model for simulation purposes and represent the metabolic demands placed on an organism. While they may be chemically balanced in certain cases, they are typically not balanced and often have only a single substrate or product. As a matter of convention the exchange reactions are further classified into demand exchange and input/output exchange reactions.

Step 440 of a computer implemented process of the invention can be carried out in an exchange reaction browser. The computer implemented process can include a routine where input/output exchange reactions are added for extracellular reactants. The extracellular reactants in the data structure can be automatically displayed on a graphical user interface based on their identification during steps 420 and 430. The process can proceed to query the user whether or not to add input/output exchange reactions for all reactants that are extracellular. If the user answers in the affirmative, the process proceeds to insert exchange reactions for all extracellular reactants. Alternatively, if the user answers in the negative, the user is given access to evaluate the extracellular reactants and is further queried as to whether each should have an input/output reaction added.

Thus, for each of the extracellular metabolites a user can specify or create a corresponding input or output exchange reaction. Generally, the system will represent these reactions as reversible with the metabolite indicated as a substrate, a stoichiometric coefficient of one and no products produced by the reaction. This particular convention is adopted to allow the reaction to take on a positive flux value for its activity level when the metabolite is being produced or drained out of the system and a negative flux value when the metabolite is being consumed or introduced into the system. These reactions can be further constrained during the course of a simulation to specify which metabolites are available to the cell and which can be secreted by the cell.

A demand exchange reaction can be introduced for any reactant in a network model of the invention. These reactions are introduced for biochemical demand constituents which are reactants that are required to be produced by the cell for the purposes of creating a new cell such as amino acids, nucleotides, phospholipids, and other biomass constituents, or metabolites that are to be produced for alternative purposes. A demand exchange reaction is generally specified as an irreversible reaction containing at least one substrate. These reactions are typically formulated to represent the production of an intracellular component by the metabolic network or the aggregate production of many reactants in balanced ratios such as in the representation of a reaction that leads to biomass formation, also referred to as growth.

At step 440, the computer implemented process can also include a routine where demand exchange reactions are added for biomass constituents. The process can proceed to query the user whether or not to add demand exchange reactions for all reactants that are biomass constituents. If the user answers in the affirmative, the process proceeds to insert demand exchange reactions for all biomass constituents. Alternatively, if the user answers in the negative, the user is given access to evaluate the biomass constituents and is further queried as to whether each should have a demand exchange reaction added.

Generally, the system will represent these reactions as irreversible and specify the reactant as a substrate with a stoichiometric coefficient of unity. With these specifications, if the reaction is active it leads to the net production of the reactant by the network model due to potential production demands. Examples of processes that can be represented as a demand exchange reaction in a network model data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

The process of constructing a data structure of network reaction components can include a step 450 of creating one or more aggregate demand exchange reactions, which specify an aggregate reactant demand flux. Aggregate demand exchange reactions are demand exchange reactions that utilize multiple reactants in defined stoichiometric ratios. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate. Thus, an aggregate reactant demand flux can define a phenotypic output for growth. Other phenotypic outputs that can be defined by an aggregate reactant demand flux include, for example, biomass production, energy production, redox equivalent production, catabolite production, biomass precursors, polypeptide production, amino acid production, purine production, pyrimidine production, lipid production, fatty acid production, cofactor production, production of a cell wall component or transport of a metabolite.

Step 450 of a computer implemented process, in which aggregate demand exchange reactions are constructed, can be carried out in an exchange reaction browser. A routine can be implemented in which the reactants in the reaction database are automatically displayed on a graphical user interface. A user can review the contents of the display and identify reactants to be included in an aggregate demand exchange reaction. Biomass demand exchange reactions can be sequentially added to the aggregate reaction and biomass constituents can be added to the aggregate reaction. The user can be queried as to whether additional reactants should be added to the reaction. If the response is in the affirmative, additional reactants can be added. Alternatively, if the response is negative, the computer implemented process can specify stoichiometric coefficients for all reaction participants. The user can then be queried to add additional aggregate exchange reactions. The user can repeat the process from the step of adding additional biomass demand exchange reactions. The routine can be repeated until a desired number of aggregate demand exchange reactions have been added.

Therefore, the invention provides a computer implemented process for constructing a scalable output network model of a bioparticle. The process includes the computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components; (c) modifying the data set to enumerate a biochemical demand on the specified network model, and (d) transforming the modified data set into a mathematical description of reactant fluxes defining the network model of connectivity and flow, wherein the enumerated biochemical demand corresponds to an aggregate reactant demand flux defining a phenotypic output of the network model of a bioparticle.

Once intra-system and exchange reactions have been added to a data structure of network reaction components, the process can move to step 460 in which testing is performed to identify network gaps or other macro requirement deficiencies. This primarily includes testing to locate gaps in the network or "dead-ends" in which a reactant can be produced but not consumed or where a reactant can be consumed but not produced. The determination of these gaps can be readily calculated through the appropriate queries of a reaction index and need not require the use of simulation strategies, however, simulation analyses are a possible approach to locating such metabolites. Gaps in a reaction network model can be identified by examining each of the reactants in the model to determine if they can be consumed and produced by the reactions therein. Gap analysis is accomplished using an algorithm that determines for each reactant if it occurs only once as a reactant or occurs multiple times as only a substrate or product when all the reactions are irreversible. If either of these criteria is satisfied then the reactant is displayed to a graphical user interface as a macro requirement deficiency. The user is then queried as to whether the gap should be accepted. The user can then decide to add or remove a reaction component from the network to eliminate the macro requirement deficiency, thereby incorporating an ameliorating network reaction component. Alternatively, the user can leave the macro requirement deficiency in the network if it is determined to have an insignificant effect on a simulation that is to be run using the network model or if the effects of the deficiency are to be determined in a simulation.

An ameliorating network reaction component that is capable of augmenting competence of the connectivity and flow of a network model can be identified by a user that interacts with the network model in a computer implemented process, as set forth above. A computer implemented process can also identify the ameliorating network reaction component automatically. Thus, an algorithm that identifies a macro requirement deficiency can further query a user to select, from a list of candidate reaction components, one or more reaction components that satisfy the deficiency. In the case where a macro requirement deficiency results in a reactant that is produced but not consumed, reactions from the universal reaction database that consume the reactant can be suggested as candidate ameliorating network reaction components. Alternatively, in the case where the macro requirement deficiency results in a reactant that is consumed but not produced, reactions from the universal reaction database that produce the reactant can be suggested as candidate ameliorating network reaction components.

Alternatively, the computer implemented process can incorporate the ameliorating network reaction component automatically. Automatic incorporation can be achieved by an iterative process in which a candidate reaction component is tested in the network model, a gap analysis is performed and if the candidate reaction component augments competence of the connectivity and flow of the network model it is included or if the candidate reaction component does not augment competence of the connectivity and flow of the network model another candidate reaction is tested. The iterative process can be repeated until at least one reaction that augments competence of the connectivity and flow of the network model is identified. In the case that more than one reaction is able to augment competence of the connectivity and flow of the network model, a user can be queried to make a selection or the selection can be made automatically based on criteria such as the confidence with which the reactions occur in other network models or the presence of an ORF in a gene database that is annotated to putatively encode one of the reactions.

Thus, a process of the invention can include a step of incorporating an identified reaction component satisfying a macro requirement deficiency in structural architecture of a network model, wherein the incorporation supplements the connectivity and flow of the network model. For example, a process of the invention can include the steps of (a) determining the occurrence of a network reaction component satisfying a macro requirement deficiency in structural architecture of the network model, and (b) incorporating an identified network reaction component satisfying the macro requirement deficiency into the data structure to supplement the connectivity and flow of the network model.

As shown in FIG. 5, the process of constructing a data structure of network reaction components can include a step 470 of introducing confidence levels for reactions included in the data structure. The introduction of confidence levels enhances model specificity and provides the advantage of maintaining quality control and accountability for the content of the model. Accordingly, the reasons why a reaction is added or deleted from a model can be determined by the model developer contemporaneously, at a later date or by other users. Furthermore, a listing of evidence or reasons for including a reaction in a model can be maintained.

A step of annotating the reaction content of a model can be, for example, a dynamic activity that is ongoing throughout the model construction cycle and can be carried out at any stage of model construction. When a reaction is first added, a user such as the model developer can indicate the information levels and provide references. Alternatively, the user can add annotation details following entry of substantially all of the reactions to be included in a versioned model.

In one embodiment, each reaction included in a data structure of network reaction components is annotated to reflect the confidence that the model developer has in the inclusion of the reaction in the model. The level of confidence is a function of the amount and form of supporting data that is available. This data can come in various forms including published literature, documented experimental results, or results of computational analyses.

In the course of constructing a network model describing associations of network reaction components the types of data that will generally be accumulated and evaluated include, for example, biochemical data, genetic data, genomic data, physiological data, and modeling data. Biochemical data includes information related to the experimental characterization of a chemical reaction, often directly indicating which biomolecule is associated with a reaction and the stoichiometry of the reaction or indirectly demonstrating the existence of a reaction occurring within a cellular extract. Genetic data includes information related to the experimental identification and genetic characterization of a gene that encodes a particular biomolecule implicated in carrying out a biochemical event. Genomic data includes information related to the identification of an open reading frame and functional assignment, through computational sequence analysis, that is then linked to a biomolecule that performs a reaction. Physiological data includes information related to overall cellular physiology, fitness characteristics, substrate utilization, and phenotyping results, which provide evidence of the assimilation or dissimilation of a compound used to infer the presence of specific biochemical event including, for example, translocations. Modeling data includes information generated through the course of in silico modeling leading to predictions regarding the status of a reaction such as whether a reaction is needed to satisfy a macro requirement deficiency.

The different forms of data elements that can be incorporated by association into a data structure of network reaction components, such as the data elements described above, can be ranked in terms of their importance toward determining the confidence level that will be assigned to a reaction. An exemplary ranking of highest information content to the lowest is as follows: biochemical, genetic, genomic, physiological, and modeling evidence.

Within each type of data element or data set there are further hierarchies that can be established which can determine the overall quality of the data leading to an estimate that a particular form of data may provide no, low, medium, or high level of confidence. Thus, confidence level can be determined from a hierarchical classification. Whether or not a reaction is included in a network model can be determined based on the relative confidence level in the hierarchy. For example, collectively hierarchical information levels can be used to heuristically determine an overall confidence level for a reaction in the model. A similar confidence scale could be used for other model content beyond just reactions.

Depending upon whether or not information was gathered for each of the five relevant information types and, if information was gathered, the level of significance that the data holds with regard to the reaction, a score of no, low, medium, or high significance can be assigned. Additional annotation information in the form of textual notes can be attached to each reaction assignment as well as a list of relevant references gathered. Collectively these annotations, attached references, and the level of evidence associated with each of the data sources constitute the reaction rating details.

A process of the invention can include a step of executing a heuristic logic decision algorithm that determines the level of confidence with which a network reaction component is included in a particular model. An overall reaction confidence level for the inclusion of a particular reaction in a data structure can be determined with a heuristic algorithm that evaluates the scores for information acquired in each of the five categories set forth above. In one embodiment, the overall confidence levels can range on a scale from one to five wherein Level 1 means the reaction is speculative with no evidence, Level 2 means the reaction is supported by minimal evidence, Level 3 means the reaction is supported by a fair amount of evidence, Level 4 means the reaction is highly probable with ample evidence and Level 5 means the reaction is certain to occur and has been validated. It is understood that these levels are exemplary and that a larger or smaller number of levels can be included to suit a particular application of the invention. An exemplary heuristic algorithm for determining confidence levels is described in Example II.

These rating levels are provided as outputs such that they can be viewed by a model user or acted upon by a computational process when assessing the reaction content of a model. Thus, the confidence levels provide an annotation from which a model user can rapidly assess the confidence in a reaction assignment or identify groups of reactions listed at a particular confidence level. The user can be given access to investigate the reaction rating details if there is a need to further examine a particular reaction. In another embodiment, the level of confidence can provide a criteria for automatically determining inclusion or exclusion of a network reaction component in a network model. For example, a user can determine a threshold value such that reactions assigned greater confidence compared to the threshold value are automatically included in a network model while those reactions for which a lesser confidence level has been assigned are excluded from the model.

The process of constructing a data structure of network reaction components can include a step 480 in which a presimulation validation test is performed to determine if sufficient components of the network model are in place to allow simulation. A model validation report can be displayed to provide a general overview of the content of the model. The report can be reviewed before using the model for simulation and versioning. Examples of information that can be included in a validation report are ORFs that have been unevaluated for inclusion or exclusion from a model, ORFs included in the model that have "hypothetical", "unknown", or "none" included in their functional annotation, extracellular reactants that do not have an input/output exchange reaction included in the model or macro requirement deficiencies in the reaction network. Based on the displayed report a user can determine whether or not to modify an associated network model.

A computer implemented process of the invention can further include a step of calculating a phenotypic output of a network model from its mathematical description. The phenotypic output can be calculated from the mathematical description using methods known in the art for flux balance analysis as described, for example, in Schilling et al., *J. Theor. Biol.* 203:229-248 (2000); Schilling et al., *Biotech. Bioeng.* 71:286-306 (2000); Schilling et al., *Biotech. Prog.* 15:288-295 (1999), and Varma and Palsson, *Biotech. Bioeng.* 12:994-998 (1994). Briefly, a mathematical description such as a matrix or system of linear equations can be solved to calculate the null space that defines the set of steady-state metabolic flux distributions that do not violate the mass, energy, or redox balance constraints. A point in this space represents a flux distribution and hence a phenotypic output for the network. An optimal solution within the set of all solutions can be determined using mathematical optimization methods when provided with a stated objective and a constraint set. The calculation of any solution constitutes a simulation of the model.

The invention provides a computer implemented process for self-optimizing a network model of a bioparticle. The process includes the computer implemented steps of: (a) accessing a database of network gene components including an annotated network set of open reading frames (ORFs) of a bioparticle genome; (b) forming a data structure associating the network gene components with network reaction components, the data structure establishing a data set specifying a network model of connectivity and flow of the network reaction components; (c) transforming the data set into a mathematical description of reactant fluxes defining the network model of connectivity and flow; (d) determining the competence of the connectivity and flow within the network model, the competence indicating underinclusion or overinclusion of network reaction component content of the network model, and (e) identifying an ameliorating network reaction component capable of augmenting the competence of the network model, incorporation of the ameliorating network reaction component into the data structure producing a modified data structure specifying in an optimized network model of the bioparticle.

Referring to FIG. 2, the model construction process can include a step 500 of preliminary simulation testing and model content refinement. In this step the existing model can be subjected to a series of functional tests to determine if it can perform basic requirements such as the ability to produce the required biomass constituents and generate predictions concerning the basic physiological characteristics of the particular organism strain being modeled. Typically, the majority of the simulations used in this stage of construction will be single optimizations, which are set forth in greater detail below. Before a network model is used to examine the ability to use an aggregate demand reaction as an objective function, the model is typically tested to determine that it is capable of generating each of the individual components. As an example, before an aggregate flux to simulate growth is used, the model is examined to determine if all of the amino acids can be generated through the model reactions and inputs. Thus, the preliminary simulation testing involves the examination of the network to produce individual reactants by selecting the appropriate single demand exchange reactions as the objective and optimizing for the production of the reactant under a wide range of possible conditions. If the metabolite cannot be made then changes can be made to the model until a desired phenotypic characteristics such as growth can be simulated.

Following a review of the content of the model and the results of preliminary simulation testing at step 600 a decision can be made as to whether or not to version the network model. If the model is not sufficiently complete to be versioned the process is repeated by returning to step 500 or, if necessary another step in the process. Accordingly, model construction can be carried out in an iterative fashion in which steps of the process are repeated until a desired model is obtained. Once the network model is determined to be sufficiently complete the process proceeds to step 700 where the model is versioned. Iterative construction leads to the continuous improvement and refinement of in silico models.

To make modifications to a model version a new open edition of the model can be created based on the model version that is to be modified. Once a model is versioned, it is generally not edited without creating a new edition. This includes changes to the reactions in the data structure of network reaction components and their associations to biomolecules and genes as well as changes to the reaction properties details such as the confidence level and references.

The invention provides a system for constructing a scalable phenotypic output network model of a bioparticle. The system includes (a) an input data set of network gene components including an annotated network set of open reading frames (ORFs) of a bioparticle genome; (b) executable instructions forming a data structure associating the network gene components with network reaction components, the data structure establishing a data set specifying a network model of connectivity and flow of the network reaction components; (c) executable instructions modifying the data set to enumerate a biochemical demand on the specified network model, and (d) executable instructions mathematically describing from the modified data set reactant fluxes defining the network model of connectivity and flow, wherein the enumerated biochemical demand corresponds to an aggregate reactant demand flux defining a phenotypic output of the network model of the bioparticle.

The invention further provides a system for constructing a scalable phenotypic output network model of a bioparticle. The system includes (a) an input data set of network gene components including an annotated network set of open reading frames (ORFs) of a bioparticle genome; (b) executable instructions forming a data structure associating the network gene components with network reaction components, the data structure establishing a data set specifying a network model of connectivity and flow of the network reaction components; (c) executable instructions determining the occurrence of a reaction component satisfying a macro requirement deficiency in structural architecture of the network model, inclusion of an identified reaction component satisfying the macro requirement deficiency in the data structure supplementing the connectivity and flow of the network model; (d) a heuristic logic decision algorithm determining confidence of the network reaction components within the data structure, and (e) executable instructions mathematically describing from the data set reactant fluxes defining the network model of connectivity and flow, wherein the mathematical description defines a scalable output network model of a bioparticle.

The invention provides a system for constructing a self-optimizing network model of a bioparticle. The system includes (a) an input data set of network gene components including an annotated network set of open reading frames (ORFs) of a bioparticle genome; (b) executable instructions forming a data structure associating the network gene components with network reaction components, the data structure establishing a data set specifying a network model of connectivity and flow of the network reaction components; (c) executable instructions mathematically describing from the data set reactant fluxes defining the network model of connectivity and flow; (d) executable instructions computing competence of the connectivity and flow within the network model, the competence indicating underinclusion or overinclusion of network reaction component content of the network model, and (e) executable instructions augmenting the competence of the connectivity and flow within the network model, the executable instructions specifying inclusion or exclusion of an ameliorating network reaction component, wherein incorporation of the ameliorating network reaction component into the data structure produces a modified data structure specifying an optimized network model of the bioparticle.

A computer system of the invention can include a number of separate modules that contain one or more use-cases having various functions associated with making and using a network model. One or more modules that can be included in the system include, for example, a universal data management module, model construction module, atlas management module, simulation module, data mining, experimental data module, gene sequence analysis module or any combination of these modules. A number of computer implemented processes of the invention are described below with reference to these modules. Those skilled in the art will understand that, although the modules provide particular advantages for organizing and managing information, as set forth below, the steps of a computer implemented process of the invention can be carried out with or without any or all of the modules.

Network gene components can be stored in a gene index and partitioned into data elements and data sets each containing information identifying a particular gene with a name or genomic location and other information including, for example, structural information such as the primary sequence of the gene or annotations describing the structure or function of the gene. The data elements can be stored in such a way that when a network gene component is accessed or included in a data structure, information relevant to the gene is associated, for example, using a hyperlink. Thus, a step of accessing a database of network gene components can include accessing a network gene component and associated information stored in a particular data element.

Information from which a network model is constructed or which can be used to modify an existing network model including, for example, a gene database, reaction database or compound database can be managed using a universal data management module. A universal data management module can include, for example, a use-case to maintain a citation library a use-case to maintain compounds, a use-case to maintain reactions, a use-case to maintain bioparticle-specific data, or a combination of two or more of these use-cases.

A use-case to maintain a citation library allows a user to manage references such as books, articles, journals and papers. This use-case can be performed using a third-party tool. The user can associate a reference with any particular reaction added to a model. This use-case interacts with a user by providing the ability to add, delete, or edit any form of reference or citation that the user my wish to include as part of a model for supporting information. The user enters a citation into the system, allowing the citation to be available for selection at any point when the user wishes to annotate any of the model content with a reference.

A use-case to maintain a database such as a compound database, reaction database or bioparticle-specific database allows a user to access and edit data elements stored therein by adding, deleting or editing information relevant to a particular entry. Such use-cases interact with a user by displaying the contents of a database and allowing the user to add a new entry to the database, delete an entry from the database, or modify an existing entry. A modification of a compound database can include, for example, changing the atomic composition of a compound or adding, deleting or editing information such as physical properties listed in an entry for a particular compound. A modification of a reaction database can include, for example, changing the atomic composition of substrates and products, the type of reaction, stoichiometric coefficient for the reaction or other information relevant to the reaction. A modification of a bioparticle-specific database can include, for example, changing names, taxonomic information, description of characteristic features or information regarding areas of practical application. A use-case for maintaining a database also provides a means to select a compound or reaction from a database, for example, using a command, query or index function that associates a selected compound or reaction to a network model data structure.

A model construction module can be included in a computer system of the invention. The methods of the invention for constructing or generating a network model can be performed in a model construction module. This module provides use-cases for managing information regarding reaction content, properties of a biomolecule or set of biomolecules that catalyze a reaction, and nucleic acids encoding the biomolecules. The model construction module can be used for any stage of model construction and modification from initial assembly, to iterative model building, preliminary testing and versioning. A model construction module can include, for example, a use-case to download a gene index, a use-case to maintain a gene index, a use-case to maintain model content, a use-case to evaluate a gene index, a use-case to maintain a reaction index, a use-case for model reconstruction, a use-case to maintain exchange reactions, a use-case to validate model structure and content, a use-case to gather model test data, a use-case to perform model testing, a use-case to version a model, a use-case to assign reactions to a region, or a combination of two or more of these use-cases.

Figure 7:
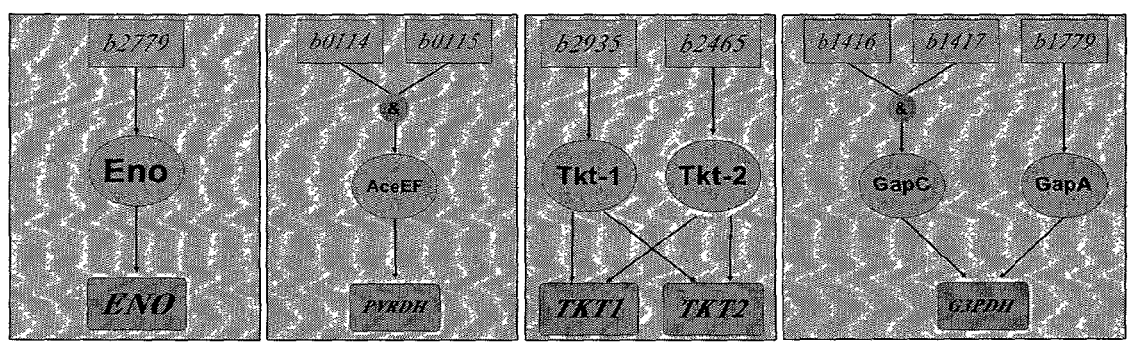
FIG. 7 shows association diagrams displaying ORF-protein-reaction associations.

A use-case to maintain model content allows a user to access and modify the content of model editions for a particular bioparticle or organism strain. This use-case interacts with a user by providing simultaneous access to a network model data structure, databases of relevant information and an association diagram. An association diagram is a display of associations between genes, the biomolecules they encode and reactions that are catalyzed or carried out by the biomolecules within a network model data structure. Exemplary association diagrams are shown in FIG. 7.

An association diagram is updated in response to commands sent by a user to add, remove or otherwise modify the content of a network model data structure. Thus, the association diagram provides a convenient visualization tool for evaluating the effect of making changes at the gene, biomolecule or reaction level in a network model data structure. Take for example, a biomolecule catalyst having multiple subunits, where all of the subunits are required for activity and where each subunit is expressed from a different gene. Visual evaluation of the gene-biomolecule-reaction associations during model construction can allow a user to readily identify the full complement of genes required to perform a particular reaction. Thus, once any one of the genes is selected from the gene index for inclusion in a data structure the user can rapidly identify the full set of genes required to perform the reaction. Furthermore, because simultaneous access is provided to multiple databases, the identified information can be displayed to a user and the user can modify a data structure based on evaluation of the displayed information.

A use-case to maintain model content can also include commands to access and edit properties of a model edition such as its name, description and notes. The content of the model edition which can be viewed and modified includes the gene index, protein index, reaction index and associated references, exchange reactions, and network gaps. This use-case also provides algorithms to create a new model edition and change the properties of the edition such as its name, description and notes.

A gene index can be managed using a model construction module. A use-case to download a gene index allows a user to load into a computer system of the invention a gene index that has been generated from external third party software or downloaded from an external database. A gene index can be downloaded as a text file or in a spreadsheet and converted to a desired format using a suitable script.

A use-case to maintain a gene index allows a user to access the data stored in a gene index and to edit the content of the data. This use-case interacts with a user by displaying the contents of a gene index and providing a means to, for example, modify the annotation and functional assignments made to individual open reading frames or genes within a genome. A gene can be added to a gene index or deleted from a gene index using this use-case.

A use-case to evaluate a gene index allows a user to evaluate the gene index for a particular organism strain to determine the genes to be included in a model edition. This use-case interacts with the user by displaying the contents of a gene index such that each gene or ORF can be evaluated for inclusion in a model edition. The user can send commands to eliminate a gene or ORF from the model or include a gene or ORF in the model. This use-case further prompts the user to indicate associations between genes, biomolecules and reactions.

A use-case to maintain a reaction index allows a user to manage the reactions that are included in a model edition. This use-case interacts with the user by displaying the contents of a reaction index and providing a means to add a reaction to the reaction index, delete a reaction from the reaction index; add, remove or view a reference from a citation library associated with a reaction; assign a reaction to a subsystem; add a confidence level to a reaction, or annotate an entry for a reaction.

A use-case for model reconstruction allows a user to determine the locations in a network model where a macro requirement deficiency or gap in the pathway structure occurs. This use-case interacts with the user by providing the ability to launch the gap analysis algorithm to locate reactants that are only consumed or produced in the network. The system then displays to the user a list of such metabolites along with information on whether they are only consumed or produced. The user can review and evaluate these macro requirement deficiencies and decide whether or not to take any action to eliminate the gap by addition or removal of reactions from the network. The user can iteratively add or delete reactions and rerun the gap analysis algorithm to determine if the gap still exists. In addition the use-case can display candidate reactions that are potentially capable of satisfying an identified macro requirement deficiency. An exemplary process for identifying a macro requirement deficiency and adding a reaction component to satisfy the deficiency is provided in Example III.

A use-case to maintain exchange reactions allows a user to manage the exchange reactions associated with a model edition. This use-case interacts with the user by providing access to a reaction index and allowing the user to identify reactions as an input exchange reaction, output exchange reaction or demand exchange reaction. In addition, a user can create, delete or modify an aggregate demand reaction with this use-case.

Intra-system reactions can be managed with a use-case for maintaining model content while exchange reactions are managed by a separate use-case. Intra-system reaction components represent true biochemical reactions that occur in a bioparticle and are potentially associated with the genes in the bioparticle. Therefore, these reactions are subject to the assignment of associations between genes, proteins, and reactions. These reactions are typically atomically and electrically balanced. Additionally, confidence levels are only assigned for these reactions and not for exchange reactions.

An algorithm can be included in a use-case for maintaining exchange reaction browser that automatically locates extracellular metabolites that occur in the reactions that are included in a network model. Extracellular metabolites identified by such an algorithm or any other means can be used for the creation of input or output exchange reactions. In addition, a use-case for maintaining exchange reactions can include an algorithm to locate biomass compounds or other biochemical demands and present them for the possible inclusion of biomass demand exchange reactions. The exchange reactions can be displayed such that a user can evaluate and select reactions to be included in a network model. Thus, the exchange reaction browser provides a means for a user to provide commands to exclude a reaction from a network model or to manually include a reaction that is not already present in the universal reaction database. A reaction added to the network model will automatically be added to the reaction database and the reactants will be added to the compound database.

A use-case to validate model structure and content allows a user to determine whether the structure and content of a model edition meet certain desired specifications before being versioned. This involves the completion of a number of basic structural analyses and the performance of some basic simulations to qualify a model as being valid. This use-case interacts with the user by performing a series of validation tests or queries on the contents of the model and reporting the results back to the user. The user can then view these results and if there are no significant problems identified, the model can be used for simulations and be versioned if desired.

A use-case to perform model testing allows a user to refine the content of a model. In this stage the existing model is subjected to a series of functional testing to determine if it can perform basic requirements such as the ability to produce the required biomass constituents and generate predictions concerning the basic physiological characteristics of the particular organism strain being modeled. A user interacts with this use-case by running simulations on the model. Based on the results of these simulations the user can make changes to the content of the model. Generally, the simulations used in this stage of construction are single optimizations.

A use-case to version a model allows a user to version an open edition of a model. This use-case interacts with a user by saving an open edition of a network model as a versioned edition in response to commands given by the user. A versioned edition of a network model is saved such that no further changes can be made to the model version. A user assigned version number is given to each of the versions of a strain specific model.

A use-case to assign or associate reactions relative to other components within a network model allows a user to identify a reaction as participating in a particular subset of reactions in a network such as in a particular metabolic pathway. The reactions in a network structure or reaction database can be subdivided, for example, according to biochemical or biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000). The use of subsystems can be advantageous for a number of analysis methods, such as extreme pathway analysis, and can make the management of model content easier. This use-case interacts with a user by displaying the contents of a network model data structure and allowing the user to select a reaction and assign the selected reaction to a subsystem.

A use-case to maintain constraint templates allows a user to maintain representative sets of data elements which define particular common intraparticle or environmental conditions. An example is a constraint template to represent aerobic growth conditions on glucose. A user interacts with this use-case by selecting a constraint template to be used as the baseline set of constraints used to run a simulation. The constraint template may be derived from a previous simulation as well. This saves the user the time required to re-enter all of the constraints placed in a new simulation that was used for the same model in a previous simulation.

Network model content also can be viewed or represented with maps that indicate the connectivity of reactions or fluxes that are present in the network. The maps can be output in a variety of different formats including, for example, two-, three- or multi-dimensional maps, diagrams and atlases. Thus, the invention provides an algorithm for displaying a map of the reactions included in all or part of a network model. A user can design a map by selecting reactions to be displayed on a map. Reactions are typically displayed with each of the reactants shown as nodes and the reactions connecting these reactants shown as arrows. The user can then arrange these reactions in a familiar layout on the map or can select to have the map layout automatically generated based on well established algorithms for auto-layout of graphs. Alternatively, an inverse map can also be designed wherein each of the reactions is indicated by a node while the metabolites are represented by arrows connecting the two nodes. An inverse map is a different way to view a metabolic reaction network that can offer advantages for the visualization of network function.

A map can be further enhanced to show the flux of network components, biochemical demands, or aggregate demand through the reactions of a network based on the results of one or more simulation. Direction of flux can be represented by arrows or apparent directional movement of an image between reactants. The amount of flux through reactions of a network can be represented in a map, for example, by the relative width of reaction arrows where a gradient of arrow widths is correlated with the amount of flux, a color gradient correlating colors in a spectrum with the relative amount of flux or the rate at which apparent directional movements of an image occur between reactants.

Also provided is a means for displaying a map that associates reactions with the biomolecules that carry out the reactions or the genes that encode the biomolecules. A map can further associate reactions, biomolecules and genes.

An atlas management module can be included in a computer system of the invention and used to manage network maps and to organize them into a collection referred to as an atlas. An atlas is a collection of maps that can cover reactions spanning one or more organism. An atlas management module can contain a use-case to manage atlases and maps, a use-case to design a map, and a use-case to view and test a map.

A use-case to manage atlases and maps allows a user to organize maps into atlases and allows the user to create or delete maps and atlases. This use-case interacts with a user by displaying a list of maps such that the user can add, delete or modify the collection of maps that are in a particular atlas. In addition, a user can interact with this use-case by copying an atlas, or map for efficient generation of a new map.

A use-case to manage atlases and maps provides access to an atlas of maps contained in separate elements or folders within an atlas. Each bioparticle or organism strain can be correlated with a default map or set of maps so that when simulations are performed in a particular model, an appropriate map is first displayed. However, maps themselves need not be linked to models. Accordingly, a computer system of the invention provides a means to load any map and view any simulation result on the map, regardless of the organism(s) from which the map was generated. This functionality allows comparison of multiple simulation results from the same or different models on the same map. Color scales can be used to represent different parameter values obtained from different simulations when displayed on the same map.

A use-case to design a map allows a user to design maps of network models. These maps provide a convenient visual tool for evaluating the content of a model in terms of the reactions included in the model and how they are connected to one another. This is a drawing and design tool that allows a user to design maps that represent network models at any of a variety of levels of detail from maps of individual pathways such as purine biosynthesis, to larger regions such as amino acid metabolism, and even substantially complete system maps of cellular metabolism.

The design use-case interacts with a user by displaying a list of reactions included in a network model data structure and providing a canvas for graphic manipulation of map content. In response to a command from a user to include a reaction in a map, the use-case will automatically add the reaction to an appropriate location according to the connectivity of the network model data structure. The user can manipulate the map by altering the location of substrates and products and arrows connecting them will be redrawn consistent with the new location on the map and the connectivity of the network model data structure. Common data elements representing the same metabolite can be merged such that locations in the map where a particular metabolite occurs are connected or otherwise correlated or common elements can be kept separate on the map. Additionally, this use-case allows a user to send a command to render one or more reactions that are present in a map as either visible or invisible.

The design use-case can provide a user with analysis capabilities to compare reactions placed on a map with reactions that occur in a particular model or region within a model. Visual features of the maps can include connectivity lines, options to handle secondary metabolites, hyperlinks to other maps, placeholders for numerical simulation results, or annotations. Additional analysis features can be included on a map such as the ability to select a metabolite of interest and simultaneously view all of the reactions in which the metabolite participates. Analysis tools such as the visual features of the maps assist the user in determining the reactions which need to be placed in the map by providing a view of the connectivity of reactions in the network while allowing access to information databases that are useful in evaluating the properties of a particular reaction in the network.

The maps can be used to display results from simulations and empirical data allowing for comparisons between simulations and experiments. For example, empirically determined results of gene expression, protein expression, protein-protein interactions or reaction rates can be compared to an in silico predicted flux distribution.

Simulations can be performed and managed with a simulation module. This module contains use-cases for different types of simulations including, for example, single optimization, deletion analysis, robustness analysis, phase plane analysis or time-course analysis. A simulation module can include, for example, a use-case to load or create a project, a use-case to manage simulations, a use-case to define optimization constraints, a use-case to perform a single optimization, a use-case to view single optimization results, a use-case to perform a deletion analysis, a use-case to view deletion analysis results, a use-case to perform robustness analysis, a use-case to view the results of robustness analysis, a use-case to perform phase plane analysis, a use-case to view results of phase plane analysis, a use-case to perform time-course analysis, a use-case to view results of time-course analysis, a use-case to compare simulation results, a use-case to compare single optimization and experimental results, a use-case to export simulation results or a combination of two or more of these use-cases.

Simulations can be managed using use-cases to load/create, manage and export simulations respectively. A use-case to load/create a project allows a user to create scientific projects and assign them to a program. Each project can contain simulation studies and additional information that are related to a particular bioparticle or related to many bioparticles. Simulation studies contain the details of individual simulations and experiments. A use-case to load/create projects interacts with the user by displaying a list of available projects from which one or more can be selected and opened by the user. A user can organize and annotate simulation results or experimental data using a use-case to manage simulations. This use-case interacts with the user by allowing the user to edit the name of a project, alter the program to which it belongs or annotate the project or program. A use-case to export simulation results can be used to convert the results to a file format, such as a text delimited file that is readable by a third-party data analysis tool.

The system can include a use-case to define optimization constraints. To perform any simulation that requires a LP problem to be solved, the user must specify the constraints (upper and lower bounds) placed on all the reactions in the network and provide an objective function. These constraints define the conditions that are being simulated, such as growth phenotype under aerobic or anaerobic conditions or with glucose or without glucose. This use-case interacts with the user by providing a list of reactions and associated constraints from which a user can view and modify constraint values. Often times there are common constraint sets that the user will continuously use. So as not to require the user to repetitively enter common constraint sets, the system can store predefined constraint sets for particular models that are defined as templates from which a user can select and load one that is desired. Thus, this use-case provides a user with the option to select and load a predefined constraint template or select a constraint set from a previous simulation to use as the starting conditions, which can then be modified and used immediately or saved for future use.

The system can include use-cases to perform any of a number of optimizations. A use-case to perform a single optimization is used to calculate a single flux distribution demonstrating how metabolic resources are routed as determined from the solution to one LP problem. A use-case to perform a deletion analysis is used to calculate the consequences of deleting at least one gene, at least one biomolecule, or at least one reaction and running multiple LPs for each deletion case. A use-case to perform a robustness analysis is used to assess the effects of reducing the allowed activity through a particular metabolic reaction leading to a series of LP problems solved at each of the activity levels within a range. A use-case to perform a phase plane analysis is used to calculate the range of characteristic functions that a network can display as a function of variations in the activity of multiple reactions wherein an LP problem is solved for every combination of parameters. A use-case to perform a time-course analysis is used to analyze the transient shifts that occur in a network over a time period wherein an LP problem is solved at each time point.

The use-cases for the various simulation types include features that allow access to linear programming algorithms and selection of parameters and data to be analyzed by the linear programming algorithms. These features include, for example, menus to load a network model, set constraints on all reactions and select an objective function. A simulation type use-case can have a user interface that includes a main series of panels containing all of the intra-system reactions, input or output exchange reactions, demand exchange reactions, and temporary reactions that have been selected for a particular simulation. Upper and lower bound constraints on reactions can be specified by a user, for example, by changing the constraints displayed in a panel on the user interface. Additionally, the user can select any reaction to be set as an objective function (such as a reaction representing cellular growth, ATP production, or a particular enzymatic reaction).

Results from each of the simulations can be viewed by a use-case of the simulation module. This use-case enables the user to view result data for a single optimization. Once a simulation has been run the solution can be output to a graphical user interface in any of a variety of acceptable formats for displaying simulation results including, for example, a table format or on a map. For any linear programming problem there are two sets of solutions, the primal solution and dual solution. Both the primal solution consisting of the flux values of all the reactions and the dual solution containing the reduced costs for the reactions and the shadow prices of the metabolites can be displayed.

A use-case for comparing simulation results is also provided and can be used to simultaneously view tables or graphs from multiple simulations. A use-case is also provided for comparing simulation results to empirical results using similar tabular or graphical outputs.

A robustness analysis can be performed by selecting a particular reaction or set of reactions for which the allowable flux level is reduced and running a simulation with the flux for the reaction(s) reduced using the use-case for performing a robustness analysis. From this use-case a user can select one or more reactions and then specify a set of constraints on the reaction(s) or, in the case where incremental changes in constraints are to be analyzed, a step size increment by which the constraints will be changed can be set. The results of the simulation can be output to the graphical user interface in a tabular or graphical form using the use-case for viewing results of a robustness analysis.

A phase plane analysis can be performed by calculating phase planes based on user defined parameters for particular reaction variables and value ranges. Here again the user specifies underlying constraint conditions and an objective value from the use-case for performing the simulation. The system runs all of the required single optimizations for one simulation and the results are presented using the viewing use-case in, for example, a tabular format or in a graphical representation. Following the simulations a shadow price analysis is performed to identify the different phases within the parameter space along with the isoclines for particular reactions specified by the user. As in all of the simulation type use-cases a particular point (or single optimization) can be selected and the system will generate the detailed solution of the corresponding single optimization for further analysis.

Another simulation type is the time-course analysis which is performed to simulate transient cellular responses. In the use-case for performing time-course analysis the user selects the baseline constraints and initial conditions from which to begin the simulation. The changes in extracellular reactant concentrations are calculated as a function of the uptake/secretion rate of the reactant, an initial concentration, and the time increment specified by the user. The results can be viewed in a table or on graph charting the changes to the parameters in the analysis as a function of time using the use-case for viewing time-course analysis results.

A data mining module can be included which provides the ability to evaluate the content of the models that have been developed. A wealth of knowledge can be derived from simple queries of the model content that do not necessarily rely on the simulation capability. A data mining module is available to manage all of these non-simulation related analyses. This includes the ability to ask questions concerning the reactions, proteins, and genes in various models. The focus can be placed on one model in particular or on comparisons between many models. Text based or map based comparisons and result analysis are available. Metabolite connectivity studies can be performed as well.

A data mining module provides a number of use-cases to view data stored in various data bases, models or results files. A use-case to view an atlas allows a user to study network models by browsing through a set of network diagrams or maps. Similarly, a use-case to view model content allows a user to evaluate the content of the models using features such as browsing gene, protein, and reaction related information in a tabular form, viewing model content on reaction maps or viewing gene-protein-reaction associations in a graphical association diagram. A reaction data base or compound database can be evaluated using use-case to view each.

A use-case can be included to perform a general content search of models. It includes the ability to ask questions concerning the reactions, proteins, and genes with the option to search within one model or across all models. Models can also be evaluated using a use-case to compare model content which allows a user to produce comparisons between many models using text-based or map-based comparisons and result analysis.

Connectivity of reactants in a model can be evaluated using a use-case provided by the invention. This use-case includes the ability to view reactant occurrences on a map, view the connectivity for a particular reactant or a model in a tabular form or in terms of a connectivity graph.

The genetic content of a bioparticle can be viewed using a use-case of the invention. This use-case includes features such as the ability to browse a gene index, view basic genetic content or view gene-protein-reaction associations.

A number of additional modules also can be included in a computer system of the invention. These modules include, for example, an experimental data module for the integration and analysis of experimental data sets from high throughput experimental technologies such as gene expression arrays, protein expression arrays, protein-protein interaction arrays or metabolite profiling. Within this module experimental data sets can be compared against simulation results and enable the user to take advantage of experimental information for the iterative improvement of the model content and its predictive capabilities. In addition to the experimental data module a gene sequence analysis module can be used to manage the process of annotating genomes to generated updated gene indices that are used to support model construction efforts. A pathway design module can also be introduced to allow for the network models to meet certain production requirements that a metabolic engineer may be seeking to design in a bacteria. This module also allows for the calculation of extreme pathways and related types of calculations which focus on the structural aspects of the metabolic networks that make up individual in silico models.

EXAMPLE I

Associating Genes, Proteins, and Reactions

This example describes construction of a network model and a reaction index for the network model. This example demonstrates interactions of a user with the model content browser to associate the chosen ORFs to protein, and proteins to reactions. This example further demonstrates how this information is modeled from an object perspective and a data schema.

A reaction index was constructed to include reaction components for both gene-associated and non gene-associated reactions. Gene-associated reactions were added to the reaction index as follows. Associations in the reaction index were formed based on known or putative associations of a reaction to the proteins or enzymes which enable or catalyze the reaction and the open reading frames (ORFs) that code for these proteins. The associations were formed to capture the relationship between the reactions and proteins as well as between the proteins and ORFs such that connectivity between the reaction, protein(s) enabling the reaction and ORF(s) encoding the protein.

The associations formed in the reaction index were displayed for review and evaluation by a user. The first panel of FIG. 7 shows a display of the association in which one ORF (b2779) encodes one protein (Eno) which catalyzes one reaction (ENO). Non-linear associations were also formed and displayed so as to capture the logic within the association. The non-linear associations for the PYRDH reaction are shown in the second panel of FIG. 7, where the requirement for both the b0114 and b0115 ORFs to encode the AceEF protein is indicated by the "AND" logic operator. Another non-linear association that was formed and displayed was that shown in the third panel of FIG. 7 where two proteins (Tkt-1 and Tkt-2) encoded by separate genes (b2935 and b2465, respectively) are each capable of enabling the same two reactions (TKT1 and TKT2). The fourth panel of FIG. 7 shows a display of the associations formed for the G3PDH reaction can be catalyzed by either the GapC or GapA protein, the former being encoded by two ORFs (b1416 and b1417) and the latter being encoded by a single ORF (b1779). The "OR" relationship between the GapC and GapA isozymes is displayed by multiple lines to the same reaction.

The displays shown in FIG. 7, by modeling associations, allowed evaluation of the network model and its constituent reaction components at the gene, protein, or reaction level or at a combination of all three levels. In constructing the network model the associations were evaluated to determine the effects of adding or eliminating a reaction component at one level upon reaction components at another level. By viewing the associations shown in the third panel of FIG. 7, it was determined that removal of either the b2935 or b2465 ORF from the network model did not prevent flux through the TKT1 or TKT2 reactions. The association diagram displayed in the fourth panel of FIG. 7 indicated that presence of either the b1779 ORF or the combination of the b1416 and b1417 ORFs will allow flux to occur through the G3PDH reaction. Thus, changes at the genetic level were readily correlated to biochemical activity of associated proteins and their reactions.

In the course of forming associations, for each reaction, the identity of proteins required or capable of performing the reaction was determined. For each protein, the number of subunits required for activity of the protein was determined. For each subunit, the number of ORFs that encode the subunit was determined. During iterative model construction, associations were formed and based upon display of the associations reaction components were evaluated for inclusion in the model.

Figure 8:
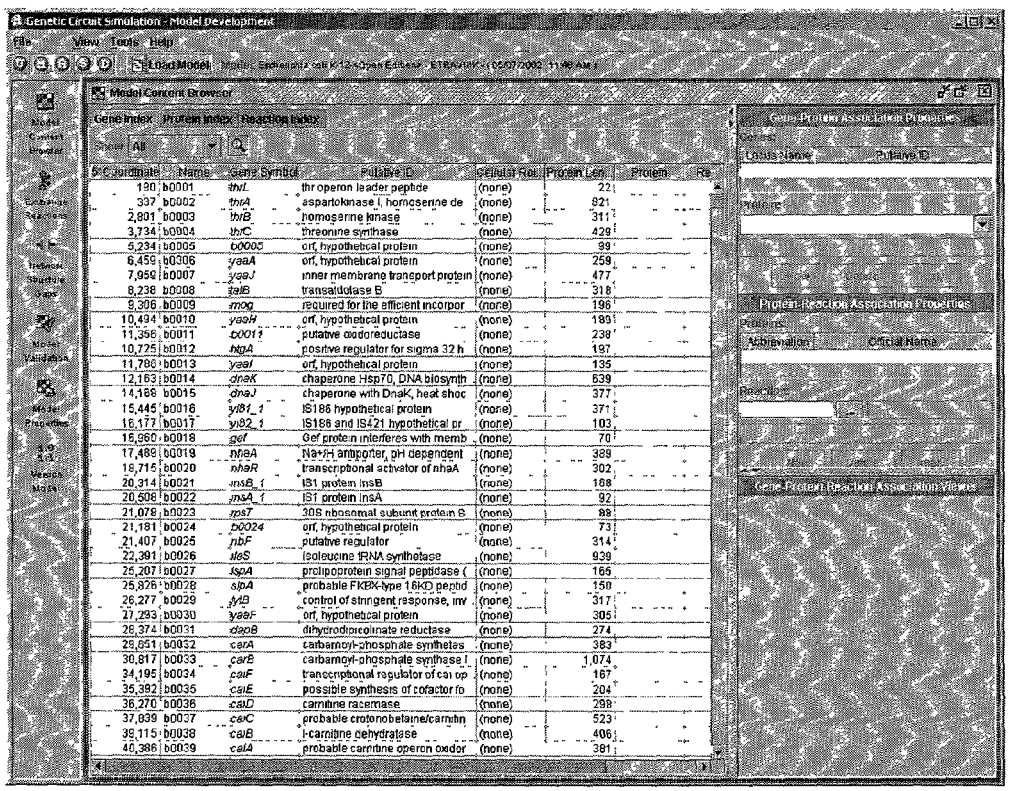
FIG. 8 shows the Model Construction main window for a system of the invention.

The gene-protein-reaction associations were formed in the Model Content Browser during the course of constructing the in silico network model. The Model Content Browser was accessed from the Model Construction main window by selecting the "Model Content Browser" button from the vertical toolbar shown in FIG. 8. The system opened the Model Content Browser window and displayed the gene index for the organism linked to the loaded model edition.

Figure 9:
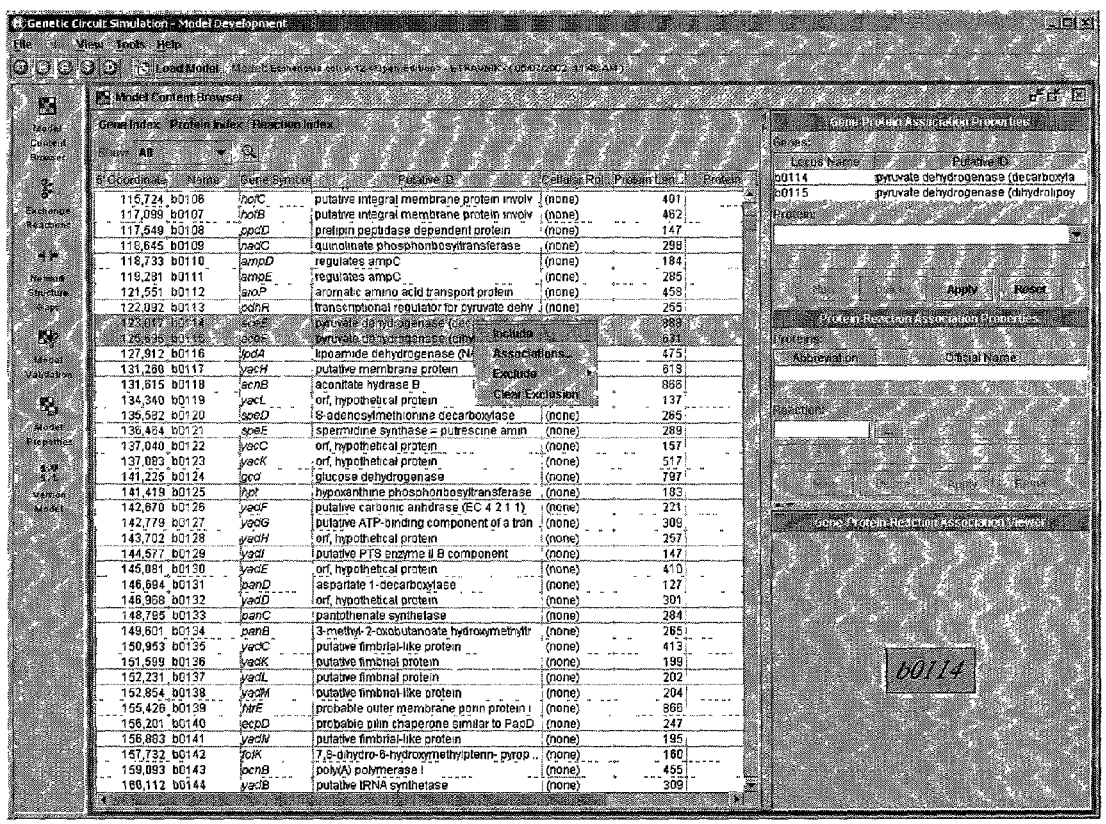
FIG. 9 shows a model construction window with a display of a gene index for a bioparticle.

The process of adding a gene-associated reaction to a model was divided into the following two steps. First, ORF-protein associations were formed. Second, protein-reaction Associations were formed. in the first step, one or more ORFs that should be associated with a reaction were identified. The gene index for the bioparticle was displayed as shown in FIG. 9. The user navigated through the index using the slider bars that flank the index display. Once identified an appropriate gene was selected by activating the option "include" from a pop-up menu, as shown for the b0114 and b0115 ORFs in FIG. 9. The selected ORFs were automatically added to the GENE-Protein-Association Properties panel shown in the upper right portion of the screen shown in FIG. 9.

Figure 10:
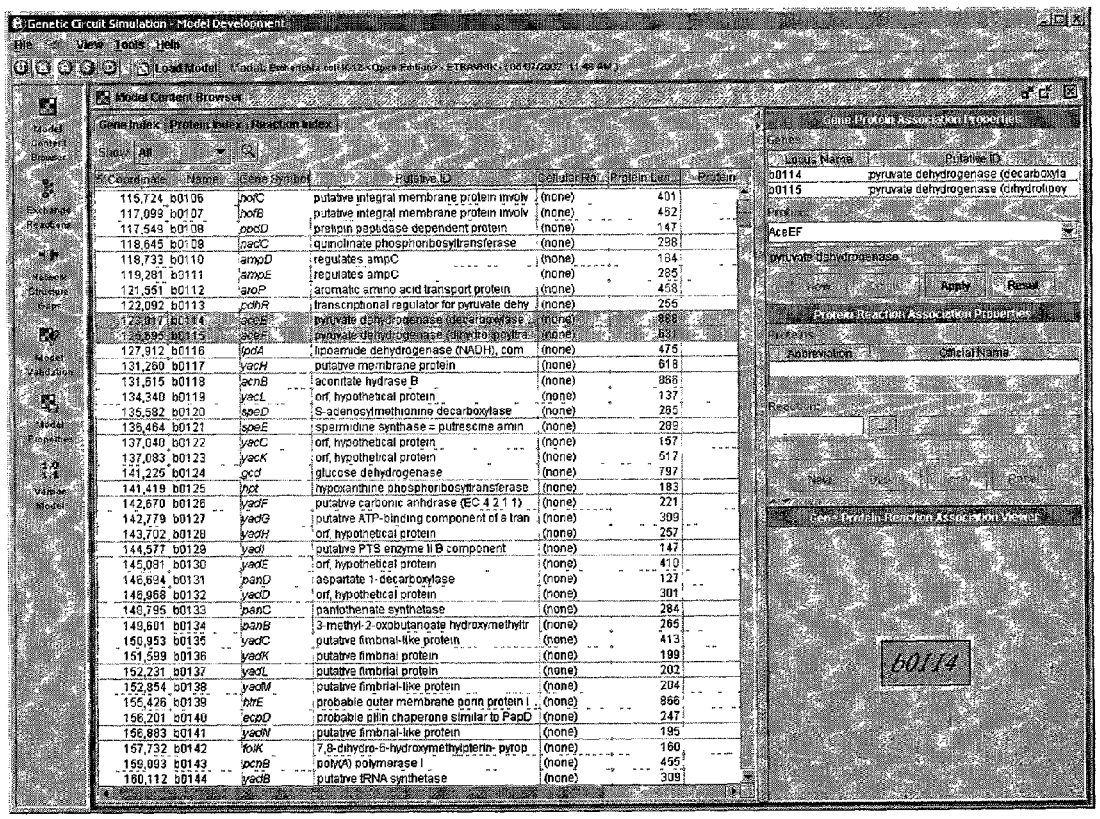
FIG. 10 shows a model construction window with in which the AceEF protein is entered into the "Protein" entry field, thereby being associated to the b0114 and b0115 ORFs.

After selecting the b0114 and b0115 ORFs, an association was formed with the protein they encode. As shown in the upper right portion of the screen shown in FIG. 10, the AceEF protein was entered into the "Protein" entry field, thereby being associated to the b0114 and b0115 ORFs. The protein was selected from a drop-down list for the "Protein" entry field. If desired the protein's abbreviation can be manually typed into the entry field. The system sent an automatic query to determine if the protein already existed in the system. Because the AceEF protein did exist the protein's name was populated in the field below the "Protein" entry field (see FIG. 10). In cases where the protein does not exist, then the system enables an entry field where the user can enter the protein's full name.

Once the ORF-protein association was correctly entered into the appropriate fields by the user, the apply button was clicked, in order to form the ORF-Protein association in the network model. The system responded by creating the appropriate database records and displayed the created associations visually in a graphical association viewer as shown in the lower right corner of the screen of FIG. 11.

The information describing the association was stored in a series of relational database tables. The following database records were created for the (b0114 and b0115)—AceEF association of FIG. 11. A peptide record was created containing the amino acid sequence of the polypeptide. In this case, the amino acid sequence was translated from the b0114 and b0115 ORFs. The peptide record was linked to the gene records for the aceE and aceF ORFs. Also created was a PeptideProteinAssociation record which represented the "AND" association of ORFs "b0114" and "b0115" to protein "AceEF". Further two PepPepProteinAssociation records were created to link ORFs "b0114" and "b0115" to the "AND" association record. These records entered as set forth above with respect to FIG. 11 was stored in the proper database according to the object model shown in FIGS. 3 and 4.

Figure 11:
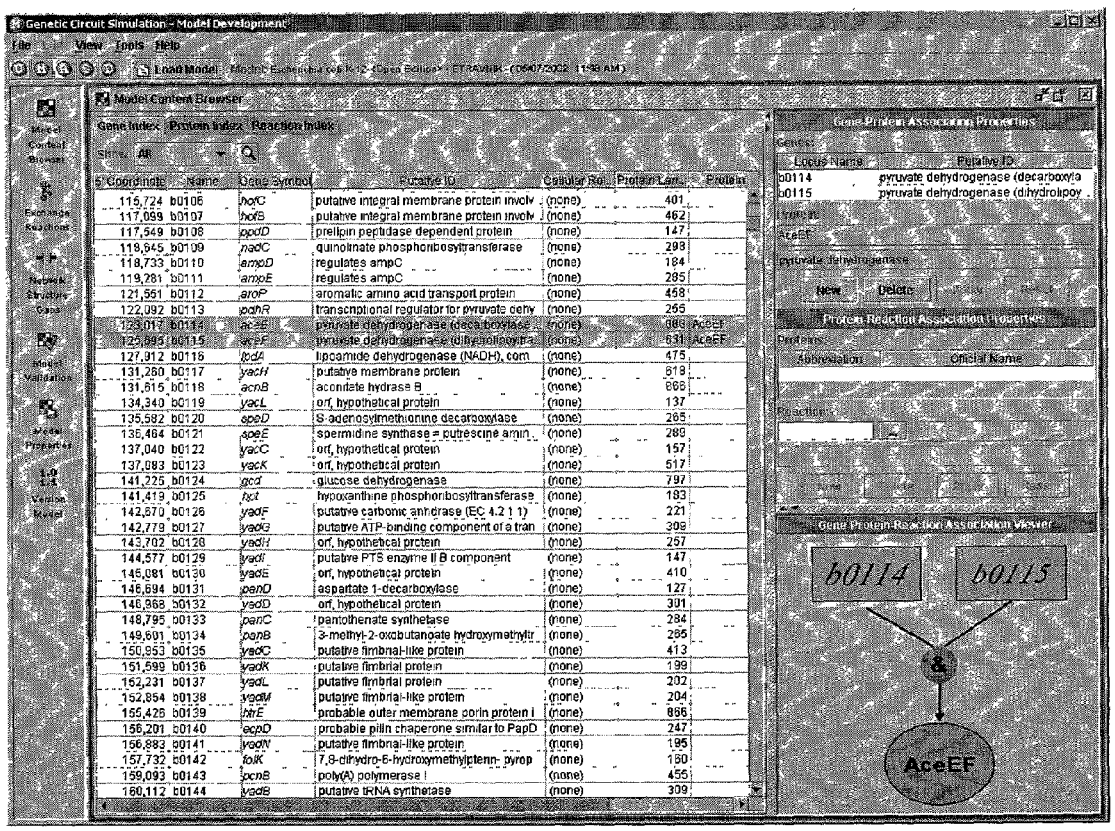
FIG. 11 shows a model construction window in which gene-protein associations for the AceEF protein are displayed visually in a graphical association viewer and the requirement for two ORFs to encode the protein is represented by an "AND" association.
Figure 12:
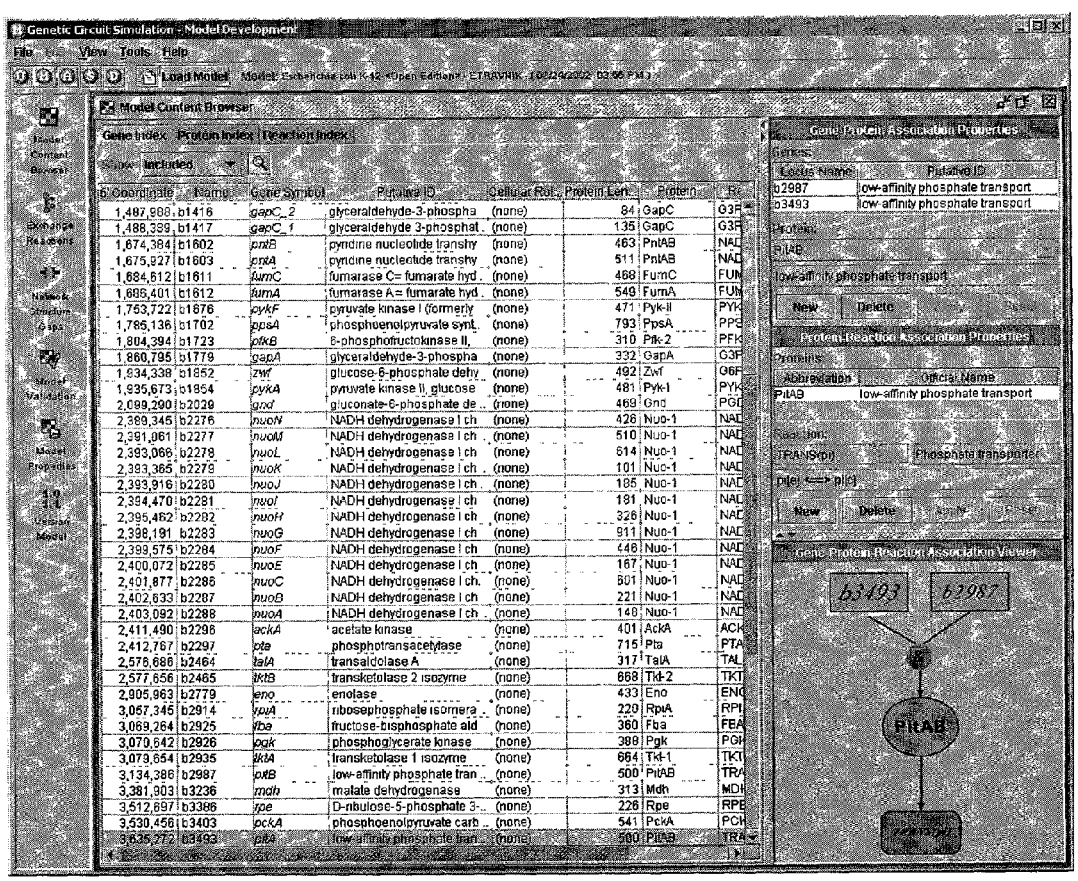
FIG. 12 shows a model construction window in which gene-protein-reaction associations for the TRANS (pi) reaction are displayed visually in a graphical association viewer and the requirement for two ORFs to encode the protein is represented by an "AND" association.

As set forth above in relation to FIG. 11, multiple genes had to be associated with one protein in an "AND" relationship. The "AND" relationship was established automatically by the system upon the user entering the relationship in the "Gene Protein Association Properties" panel and sending the "apply" command. As shown in FIGS. 11 and 12, the graphical viewer represents this type of association with an "&" symbol. An AND relationship between multiple genes and a protein reflects the quaternary structure of the protein including multiple subunits.

Figure 13:
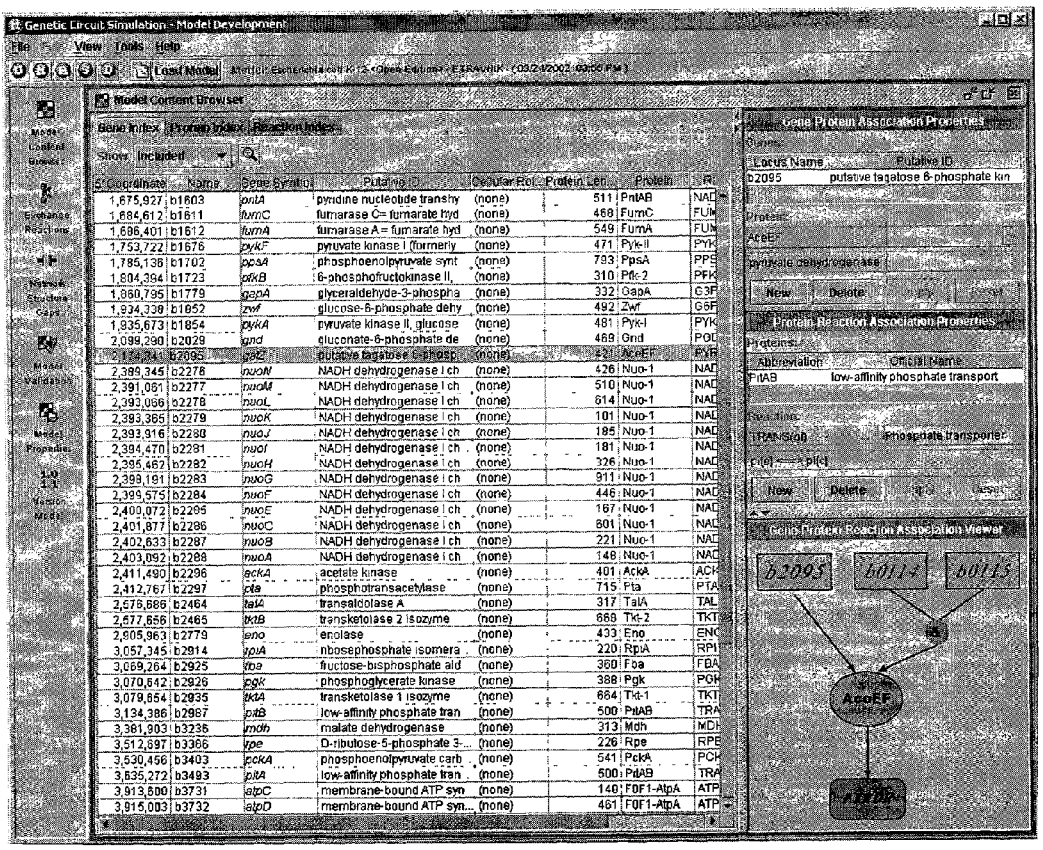
FIG. 13 shows a model construction window in which gene-protein-reaction associations for the PYRDH reaction are displayed and different isozymes that catalyze the reactions are represented by drawing multiple lines between the ORFs and the protein.

There are two isozymes of the AceEF protein both capable of performing the PYRDH reaction. The first isozyme is encoded by the b0114 and b0115 genes. The second isozyme is encoded by the b2095 ORF. The relationship of the isozymes to the reaction was captured with an "OR" logic operator. As shown in FIG. 13, the graphical association viewer represents an "OR" association by drawing multiple lines between the ORFs and the protein. The "OR" association is established when the user associates ORFs separately with the same protein.

Figure 14:
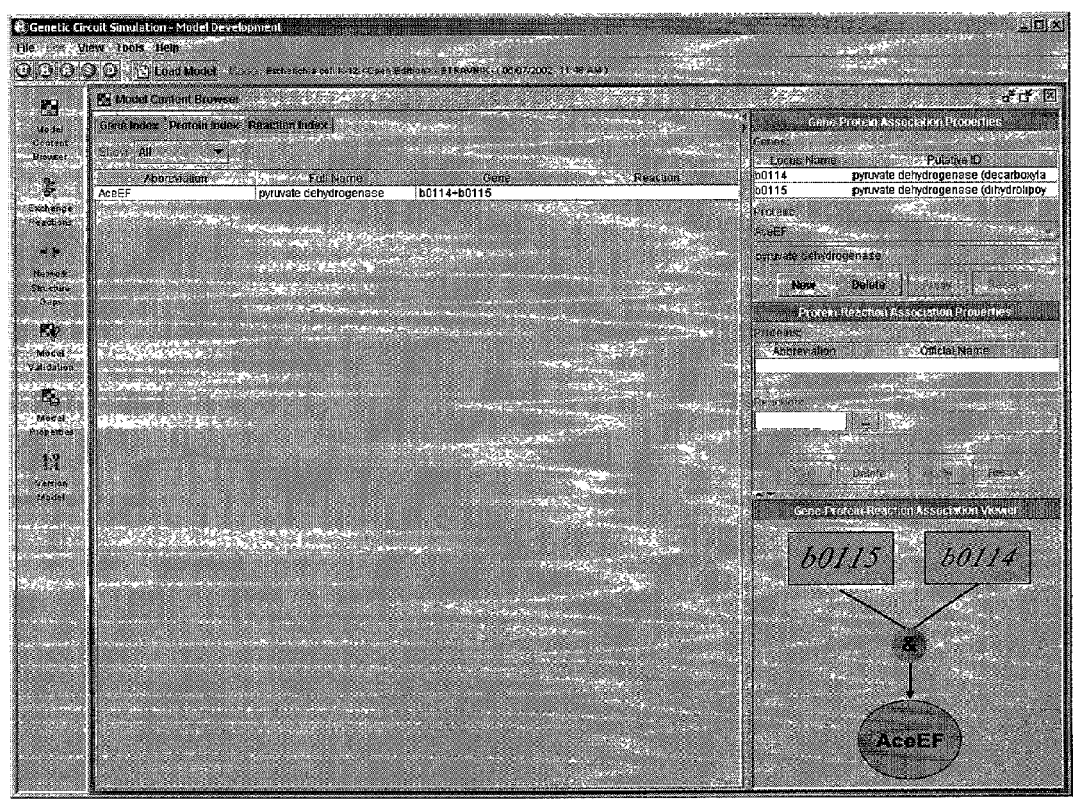
FIG. 14 shows a model construction window in which a protein that is associated with a model is displayed in a table.
Figure 15:
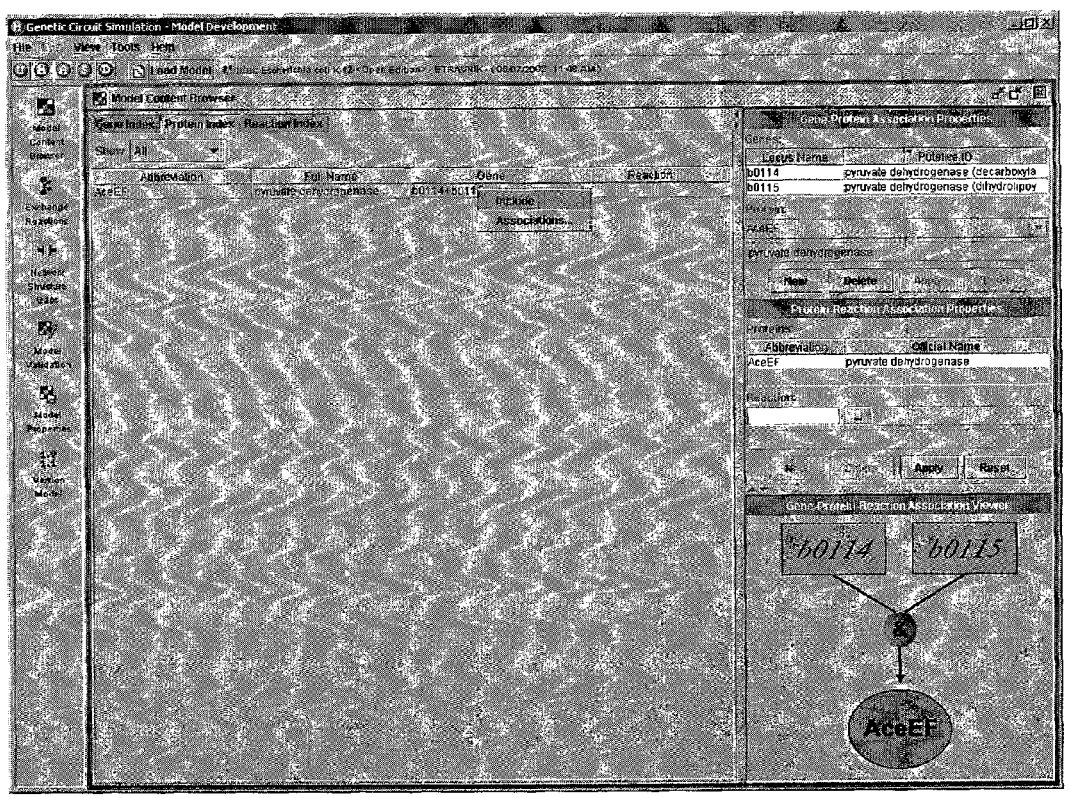
FIG. 15 shows a model construction window in which a protein that is associated with a model and displayed in a table is selected for inclusion in a model.

Next associations were formed between proteins and reactions. The Protein Index view was accessed by clicking on the "Protein Index" tab in the Model Content Browser. The system displayed all proteins that are associated with the model in a table as shown in FIG. 14. The appropriate protein, in this case AceEF, was selected from the protein index via the "Include" option from a pop-up menu as shown in FIG. 15. In response the system populated the selected protein in the Protein-Reaction Association Properties panel on the right side of the screen.

Figure 16:
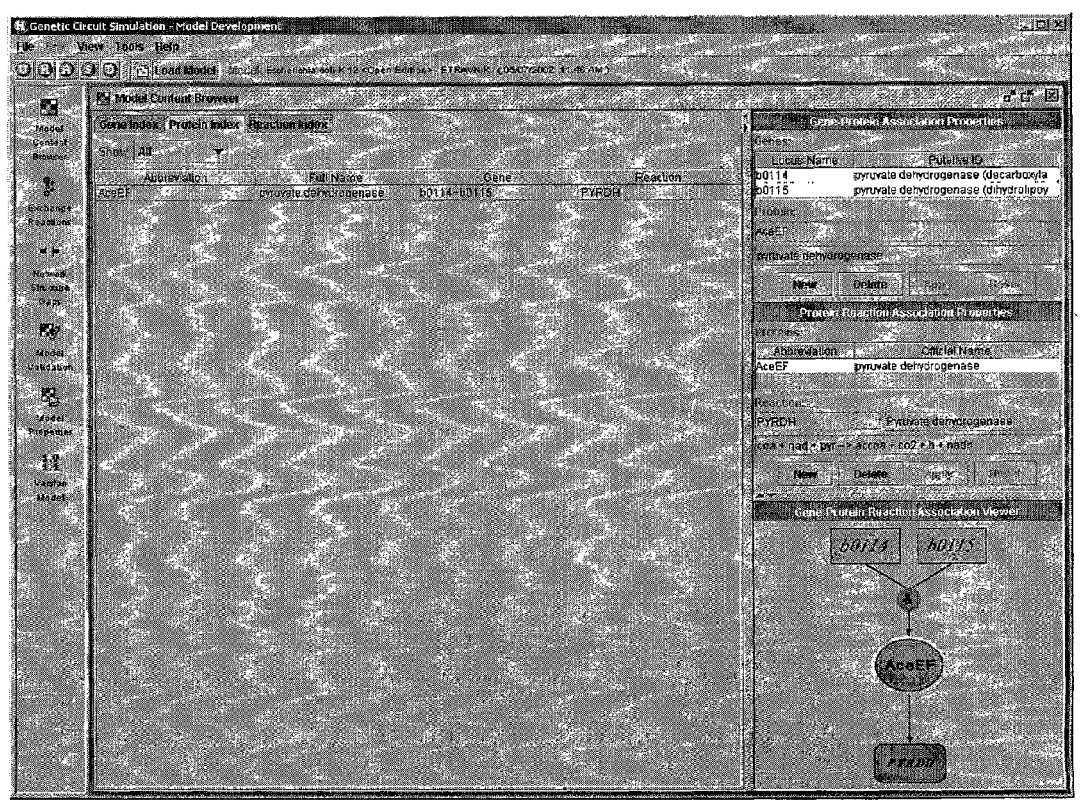
FIG. 16 shows a model construction window in which ORF-protein-reaction associations are visually displayed in a graphical association viewer.

A reaction associated with the aceEF protein was entered into the "reaction" field. In this case the system found the reaction based on the abbreviation entered and populated the full name and equation in the appropriate fields. If the user does not know the reaction's abbreviation, the "..." button can be selected to open a Reaction Browser window where reactions can be looked up from the reaction database based on any of a number of various criteria. Once the association was correctly entered the "apply" button was clicked to form the Protein-Reaction association in the network model. In response, the system then created the appropriate database records and displayed the created association(s) visually in a graphical association viewer located in the lower right corner of the screen shown in FIG. 16.

The system created the following database records for associations formed as described above in relation to FIG. 16. A ModelReaction record was created to link the chemical reaction to the model. A ProteinReactionAssociation record was created to link the protein "AceEF" to the model reaction. A ProtProtReactionAssociation record was created to link the ProteinReactionAssociation to protein "AceEF".

Protein-reaction "AND" and "OR" associations were established and displayed essentially as set forth above in regard to ORF-protein associations. A display of a protein-reaction "AND" association is shown in the graphical viewer in the lower right hand corner of the screen shown in FIG. 17. A display of a protein-reaction "OR" association is shown in the graphical viewer in the lower right hand corner of the screen shown in FIG. 18.

Figure 17:
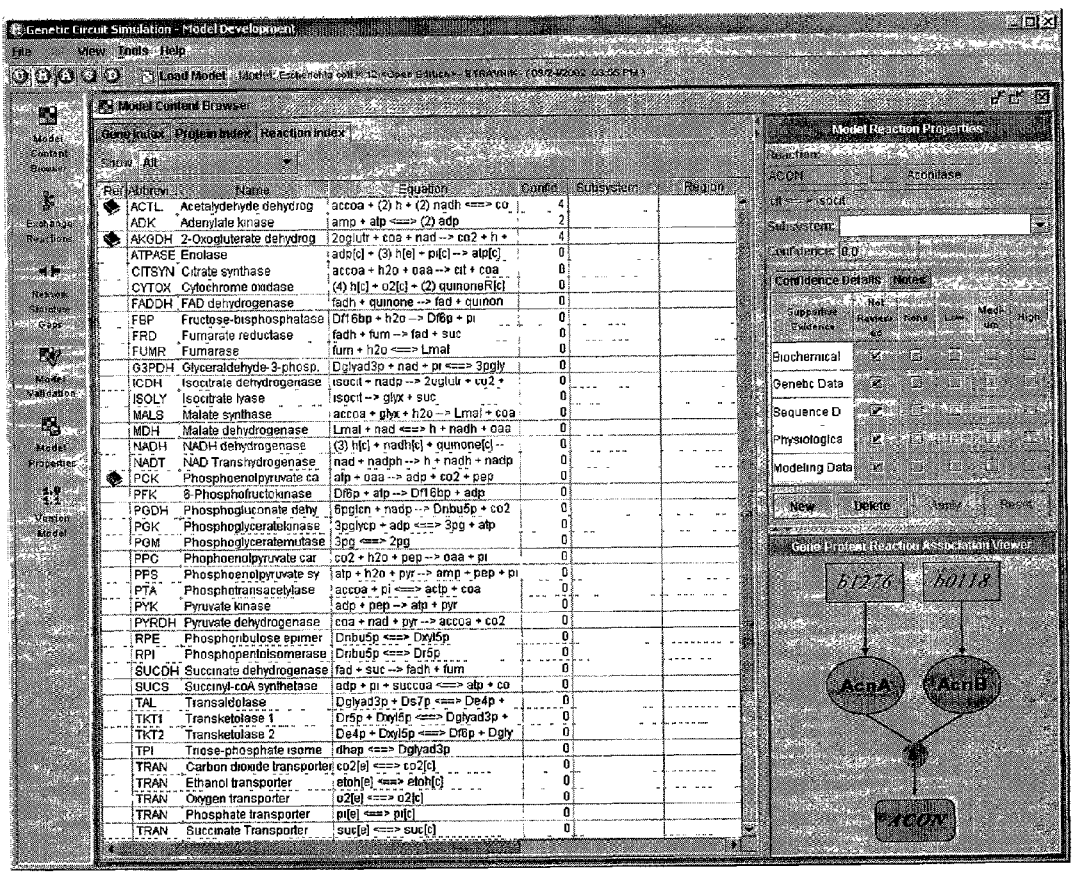
FIG. 17 shows a model construction window in which a protein-reaction "AND" association is displayed in a graphical viewer.
Figure 18:
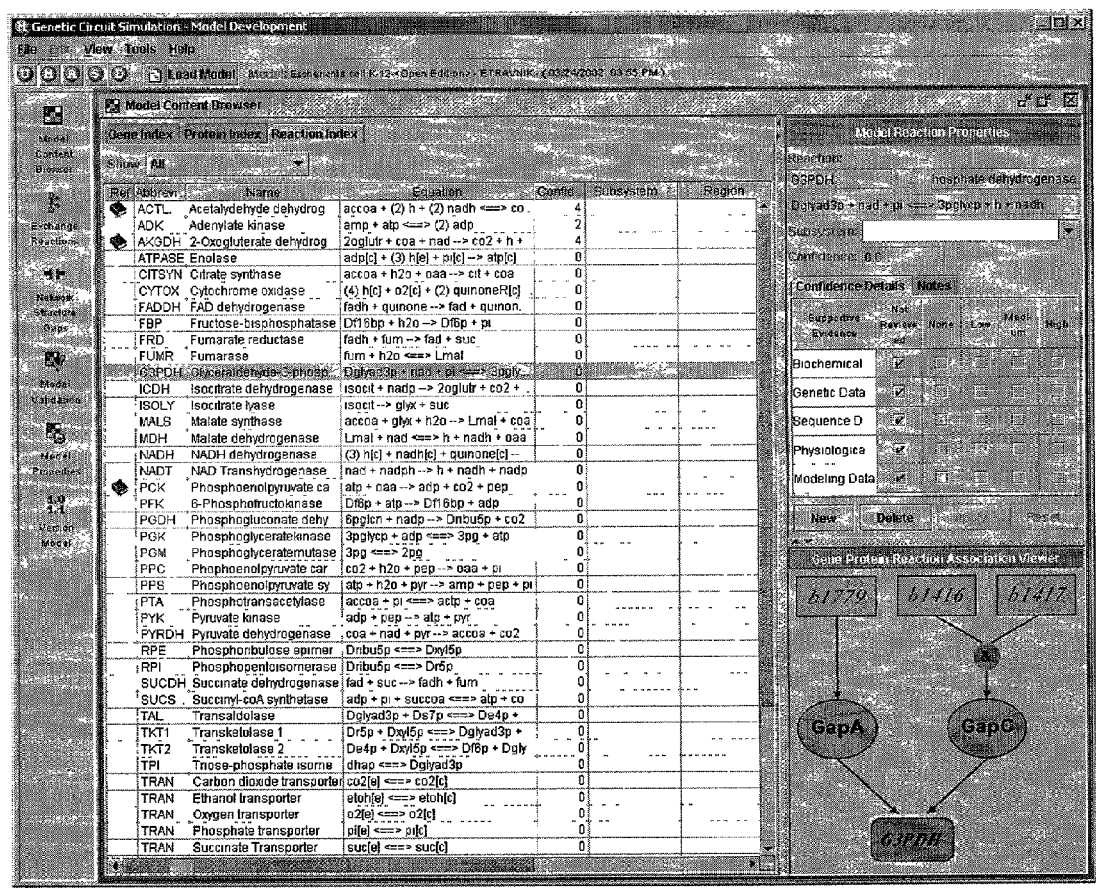
FIG. 18 shows a model construction window in which a protein-reaction "OR" association is displayed in a graphical viewer.

As shown in FIG. 17, where references describing a particular reaction are available and have been entered into the reference database, a link is provided to the reference by a "book icon" in the left hand column. For the reaction list shown on the display of FIG. 17, the ACTL, AKGDH and PCK reactions have links to references.

FIG. 17 also shows a display in which the model reaction properties viewer is opened. In this viewer is shown information related to the confidence rating of the selected reaction. An overall confidence score is provided as well as a table showing the confidence details for five different categories. Confidence details and confidence scores are described in Example II.

As shown in FIGS. 3 and 4, the following classes participate in the creation of Gene-Protein Associations:
(1) Peptide
(2) PeptideProteinAssociation and
(3) Protein.

The following classes participate in the creation of Protein-Reaction Associations:
(1) Protein
(2) ProteinReactionAssociation and
(3) ModelReaction.

The following tables participate in the creation of Gene-Protein Associations:
(1) Peptide
(2) PeptideProteinAssociation
(3) PepPepProteinAssociation and
(4) Protein.

The following tables participate in the creation of Protein-Reaction Associations:
(1) Protein
(2) ProteinReactionAssociation
(3) ProtProtReactionAssociation and
(4) ModelReaction.

EXAMPLE II

Heuristic Algorithm for Confidence Level

This example demonstrates a heuristic algorithm for determining overall confidence for inclusion of a reaction component in a particular network model based upon the level of information acquired in each of five categories.

The confidence levels range on a scale from zero to four with four being the highest rating level. A simple five level scale is adequate to distinguish between reactions with low confidence versus those with high confidence. The algorithm takes the level of significance assigned to each information category and filters them into a quantitative confidence level. The five levels will provide a basic indication of the confidence that the model content developer has in a reaction and the associated protein(s) and ORF(s) being included in a model. The meaning of the five levels is provided below Level 0—the reaction has no calculated confidence
Level 1—the reaction is supported by minimal evidence or even no evidence
Level 2—the reaction is supported by a fair amount of evidence
Level 3—the reaction is highly probable with ample evidence
Level 4—the reaction is certain to occur and has been validated The algorithm is based on the following equation:

$$CV = \sum_{i=1}^{5} InfoType_i * InfoLevel_i$$

where CV is the confidence value that will be used to determine the confidence level, $InfoType_i$ refers to a preset numerical value established for each of the five information types (biochemical, genetic, genomic, physiological, modeling), and $InfoLevel_i$ refers to the preset numerical value for the information level that is associated with the specific information type.

The following values were used for the preset numerical values for the information type and level:

| InfoType | |
|---|---|
| Biochemical | 10 |
| Genetic | 8 |
| Genomic | 5 |
| Physiological | 3 |
| Modeling | 1 |
| Infolevel | |
| Not evaluated | 0 |
| None | 0.1 |
| Low | 1 |
| Medium | 2 |
| High | 3 |

Table 1 provides the range of confidence values that will correspond to the confidence levels to be prescribed to each of the reactions.

TABLE 1

| Confidence Value Range | | Confidence |
|---|---|---|
| Lower Value | Upper Value | Level |
| 0 | 0 | 0 |
| 0.1 | 8 | 1 |
| 8.1 | 16 | 2 |
| 16.1 | 22 | 3 |
| 22.1 | 81 | 4 |

This framework for calculating the confidence rating allows for future alterations to the preset numerical values and ranges associated with each of the different information levels and types based on experiences gathered from implementing the confidence rating system described above.

EXAMPLE III

Identification and Satisfaction of a Macro Requirement Deficiency

This example describes analysis of a network model to identify a gap.

The user selects the "Run Gap Analysis" button to activate the network analysis. In response, the system activates the network analysis and identifies the presence of gaps defined as either metabolites that occur only once as a reactant or metabolites that occur multiple times as only a substrate or product with all the reactions being irreversible.

These situations will cause the associated reactions never to be utilized in the model simulations. For each gap, the system displays the name of the compound, the compartment in which the compound occurs, a description that indicates if the compound is consumed only or produced only, a checkbox that enables users to indicate which gaps have been reviewed. All gaps are sorted by compound abbreviation.

In the following two examples, A and B occur only once as a reactant. A and B represent gaps if the reaction is reversible or irreversible.

In the following example, B occurs multiple times as only a product (B is produced only) and all reactions it participates in are irreversible. B represents a gap.

In the following example, B occurs multiple times as only a substrate (B is consumed only) and all reactions it participates in are irreversible. B represents a gap.

In the following example, B occurs multiple times as only a product (assuming that the second reaction was expressed as C<->B and not as B<->C) but one reaction is reversible. B does not represent a gap.

Throughout this application various publications have been referenced within parentheses. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A computer implemented process for constructing a scalable output metabolic network model of a bioparticle, comprising the computer implemented steps of:
   (a) accessing a database of network gene components comprising an annotated network set of open reading frames (ORFs) of a bioparticle genome;
   (b) forming a data structure comprising network gene components of said database and metabolic reactions of said metabolic network model and associating said network gene components with said metabolic reactions, wherein said associations are formed with logic operators indicating linear, non-linear and both linear and non-linear associations between said network gene components and said metabolic reactions, said data structure establishing a data set specifying a metabolic network model of connectivity and flow of said metabolic reactions,
   (c) executing commands in a suitably programmed computer to transform said data set into a mathematical description of reactant fluxes defining said metabolic network model of connectivity and flow, wherein said metabolic network model of connectivity and flow indicates the quantitative amount of flux through said metabolic reactions under a given set of conditions and wherein said mathematical description defines a scalable output metabolic network model of a bioparticle, and
   (d) providing an output to a user of said scalable output metabolic network model.

2. The process of claim 1, wherein forming said data structure further comprises:
   (a) selecting an ORF from said annotated network set encoding a gene product having a network reaction function;
   (b) forming a data structure comprising said selected gene product, said data structure associating network gene components and network reaction components comprising cognate ORFs, encoded gene products, network reactions and reaction constituents, and
   (c) repeating steps (a) and (b) selecting another ORF from said annotated network set until substantially all of said network gene components of said annotated network set have been surveyed for encoding a gene product having a network reaction function to produce a data structure establishing a data set specifying a network model of connectivity and flow.

3. The process of claim 2, further comprising:
   (a) determining the occurrence of a constituent gene product for said selected encoded gene product;
   (b) determining the occurrence of an additional gene product participating in said network reaction;
   (c) determining the occurrence of an alternative network reaction exhibited by a surveyed gene product;
   (d) incorporating identified constituent gene products, participating gene products or alternative network reaction into said data structure.

4. The process of claim 1, further comprising incorporating a network reaction that is not gene-encoded and corresponding metabolic reaction constituents of said reaction that is not gene-encoded into said data structure.

5. The process of claim 1, further comprising elemental balancing on at least one network reaction.

6. The process of claim 1, further comprising charge balancing on at least one network reaction.

7. The process of claim 1, further comprising incorporating an exchange reaction for reaction component external to said network model and corresponding reaction constituents for said external reaction into said data structure.

8. The process of claim 7, wherein said reaction component external to said network model comprises a metabolite or a biochemical demand constituent.

9. The process of claim 8, wherein said biochemical demand further comprises an aggregate reactant demand flux defining a phenotypic output for growth.

10. The process of claim 9, wherein said phenotypic output for growth comprises biomass production.

11. The process of claim 8, wherein said biochemical demand further comprises an aggregate reactant demand flux defining a phenotypic output selected from the group consisting of energy production, redox equivalent production, catabolite production, biomass precursors, polypeptide production, amino acid production, purine production, pyrimidine production, lipid production, fatty acid production, cofactor production, production of a cell wall component and transport of a metabolite.

12. The process of claim 1, wherein said data structure comprises reactants, products and stoichiometric coefficients.

13. The process of claim 1, wherein said mathematical description comprises linear equations and inequalities.

14. The process of claim 13, wherein said mathematical description comprises a stoichiometric matrix.

15. The process of claim 13, wherein said mathematical description comprises differential equations.

16. The process of claim 1, further comprising calculating a phenotypic output of said network model from said mathematical description.

17. A system for constructing a scalable output metabolic network model of a bioparticle, comprising a processor and computer-implemented instructions stored therein which cause said processor to perform the steps of:

(a) providing an input data set of network gene components comprising an annotated network set of open reading frames (ORFs) of a bioparticle genome;
(b) forming a data structure comprising said network gene components and metabolic reactions of said metabolic network model and associating said network gene components with said metabolic reactions, wherein said associations are formed with logic operators indicating linear, non-linear and both linear and non-linear associations between said network gene components and said metabolic reactions, said data structure establishing a data set specifying a metabolic network model of connectivity and flow of said metabolic reactions;
(c) determining the occurrence of a metabolic reaction component satisfying a macro requirement deficiency in structural architecture of said metabolic network model, inclusion of an identified metabolic reaction component satisfying said macro requirement deficiency in said data structure supplementing said connectivity and flow of said metabolic network model;
(d) providing a heuristic logic decision algorithm determining a confidence level of said metabolic network reaction components within said data structure, and
(e) providing an output to a user of a mathematical description generated from said data set reactant fluxes defining said metabolic network model of connectivity and flow, wherein said metabolic network model of connectivity and flow indicates the quantitative amount of flux through said reactions under a given set of conditions and wherein said mathematical description defines a scalable output network model of a bioparticle.

18. The process of claim 1, wherein said data structure further comprises reaction components and wherein said associations in said data structure associate a reaction to a reaction component or reaction components that carry out the reaction and the gene component or gene components that encode said reaction component or reaction components.

19. The process of claim 1, wherein at least one of said associations has one gene component and one reaction; at least one of said associations has multiple gene components and one reaction; and at least one of said associations has multiple gene components and multiple reactions.

20. The process of claim 1, wherein at least one of said associations has one gene component, one reaction component and one reaction; at least one of said associations has multiple gene components, one reaction component and one reaction; at least one of said associations has multiple gene components, multiple reaction components and multiple reactions; and at least one of said associations has multiple gene components associated with a first reaction component and one gene component associated with a second reaction component and both first and second reaction components associated with a reaction.

21. The computer implemented process of claim 1, wherein said data set specifying a network model of connectivity and flow indicates the quantitative amount of flux.

22. The system of claim 17, wherein said data set specifying a network model of connectivity and flow indicates the quantitative amount of flux.

23. A computer implemented process for constructing a scalable output metabolic network model of a bioparticle, comprising the computer implemented steps of:
(a) accessing a relational database comprising network gene components, metabolic reaction components and metabolic reactions;
(b) forming a data structure comprising gene component-reaction component-reaction associations for said network gene components, metabolic reaction components and metabolic reactions,
  each of said gene components being associated to each of said metabolic reaction components through linking:
    one or more records each comprising an amino acid sequence to one or more records each comprising an open reading frame (ORF) encoding said amino acid sequence, and
    one or more association records linking said one or more records each comprising an amino acid sequence or said one or more records each comprising an encoding ORF sequence to one or more association records representing a
  Boolean logic operator linked to a record comprising said metabolic reaction component or to a record comprising said metabolic reaction component;
  each of said metabolic reaction components being associated to each of said metabolic reactions through:
    one or more association records linking one or more records each comprising a metabolic reaction to said metabolic network model;
    one or more association records linking one or more records each comprising a metabolic reaction component to said one or more records each comprising a metabolic reaction, and
    one or more association records linking one or more association records representing a Boolean logic operator to a record comprising said metabolic reaction component, said data structure establishing a data set specifying a metabolic network model of connectivity and flow of said metabolic network reaction components;
(c) executing commands in a suitably programmed computer to transform said data set into a mathematical description of metabolic reactant fluxes defining said metabolic network model of connectivity and flow, wherein said metabolic network model of connectivity and flow indicates the amount of flux or the rate of flux through said metabolic network reaction components under a given set of conditions and wherein said mathematical description defines a scalable output metabolic network model of a bioparticle, and
(d) providing a visual output to a user of said scalable output metabolic network model.

* * * * *